(12) United States Patent
Calabrese

(10) Patent No.: US 10,570,166 B2
(45) Date of Patent: *Feb. 25, 2020

(54) SPINOSYN DERIVATIVES AS INSECTICIDES

(71) Applicant: AGRIMETIS, LLC, Lutherville, MD (US)

(72) Inventor: Andrew Calabrese, Lutherville, MD (US)

(73) Assignee: AgriMetis, LLC, Lutherville, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 15/757,204

(22) PCT Filed: Sep. 1, 2016

(86) PCT No.: PCT/US2016/049870
§ 371 (c)(1),
(2) Date: Mar. 2, 2018

(87) PCT Pub. No.: WO2017/040763
PCT Pub. Date: Mar. 9, 2017

(65) Prior Publication Data
US 2018/0251487 A1  Sep. 6, 2018

Related U.S. Application Data

(60) Provisional application No. 62/214,083, filed on Sep. 3, 2015, provisional application No. 62/290,676, filed on Feb. 3, 2016, provisional application No. 62/303,015, filed on Mar. 3, 2016, provisional application No. 62/303,078, filed on Mar. 3, 2016, provisional application No. 62/380,664, filed on Aug. 29, 2016.

(51) Int. Cl.
C07H 17/08 (2006.01)
A01N 45/02 (2006.01)
C07H 1/00 (2006.01)

(52) U.S. Cl.
CPC ............. *C07H 17/08* (2013.01); *A01N 45/02* (2013.01); *C07H 1/00* (2013.01)

(58) Field of Classification Search
CPC ................................. C07H 17/08; A01N 45/02
See application file for complete search history.

(56) References Cited

U.S. PATENT DOCUMENTS

| | | |
|---|---|---|
| 6,001,981 A | 12/1999 | DeAmicis et al. |
| 6,063,771 A | 5/2000 | Snyder |
| 6,342,482 B1 | 1/2002 | Snyder |
| 6,919,464 B1 | 7/2005 | Crouse et al. |
| 6,927,210 B1 | 8/2005 | Thompson et al. |
| 7,015,001 B2 | 3/2006 | Baltz et al. |
| 7,709,447 B2 | 5/2010 | Hacket et al. |
| 8,470,381 B2 | 6/2013 | Kritikou |
| 8,536,142 B2 | 9/2013 | Lowe et al. |
| 8,697,661 B2 | 4/2014 | Kritikou |
| 9,253,979 B2 | 2/2016 | Sparks et al. |
| 9,873,639 B1 | 1/2018 | Doccola et al. |
| 9,895,388 B1 | 2/2018 | Mettert et al. |
| 2012/0172322 A1 | 7/2012 | Sparks et al. |
| 2012/0252746 A1 | 10/2012 | Snyder |
| 2013/0172215 A1 | 7/2013 | Palaniappan et al. |
| 2013/0210755 A1 | 8/2013 | Marr et al. |
| 2015/0111743 A1 | 4/2015 | Gomez et al. |

FOREIGN PATENT DOCUMENTS

| | | |
|---|---|---|
| CN | 102977166 A | 3/2013 |
| EP | 1207757 B1 | 2/2005 |
| EP | 2654757 A1 | 10/2013 |
| WO | 97/00265 | 1/1997 |
| WO | 02/077004 A1 | 10/2002 |
| WO | 03070908 | 8/2003 |
| WO | 2017/040763 A1 | 3/2017 |
| WO | 2017/040769 A1 | 3/2017 |
| WO | 2017/040878 A1 | 3/2017 |
| WO | 2017/040882 A1 | 3/2017 |

OTHER PUBLICATIONS

"Derivative", Merriam-Webster OnLine Dictionary, also available at http://www.merriam-webster.com/dictionary/derivative; retrieved Jul. 2009 (Year: 2009).*
Kirst, "The Spinosyn Family of Insecticides: Realizing the Potential of Natural Products Research", The Journal of Antibiotics, vol. 63, No. 3, Feb. 12, 2010, pp. 101-111.
Mergott et al., "Total synthesis of (-) spinosyn A", Proceedings of the National Academy of Sciences, vol. 101, No. 33, http://www.pnas.org/content/101/33/11955.full.pdf, Aug. 17, 2004, pp. 11955-11959.
Methot et al., "Applications of tricoordinated phosphorus compounds in organocatalysis", Database Caplus [Online] Chemical Abstracts Service, Columbus,XP002763249, retrieved from STN Database accession No. 2009:453327 abstract, Science of Synthesis, vol. 42, 2009, pp. 469-501.
PCT/US2016/049870, "International Preliminary Report on Patentability", dated Mar. 15, 2018, 7 pages.
PCT/US2016/049870, "International Search Report and Written Opinion", dated Nov. 3, 2016, 11 pages.
PCT/US2016/049879, "International Preliminary Report on Patentability", dated Mar. 15, 2018, 11 pages.
PCT/US2016/049879, "International Search Report and Written Opinion", dated Jan. 2, 2017, 17 pages.
PCT/US2016/050028, "International Preliminary Report on Patentability", dated Mar. 15, 2018, 7 pages.
PCT/US2016/050028, "International Search Report and Written Opinion", dated Oct. 25, 2016, 12 pages.

(Continued)

*Primary Examiner* — Shaojia A Jiang
*Assistant Examiner* — Bahar Craigo
(74) *Attorney, Agent, or Firm* — Kilpatrick Townsend & Stockton LLP

(57) ABSTRACT

Compositions including derivatives of spinosyns and methods for the production of derivatives of spinosyns are provided. The spinosyn derivatives described herein include spinosyn derivatives functionalized on the C5-C6 double bond of the spinosyn. The method produces spinosyn derivatives that exhibit activity towards insects, arachnids, and nematodes and are useful in the agricultural and animal health markets.

19 Claims, No Drawings

(56) References Cited

OTHER PUBLICATIONS

PCT/US2016/050034, "International Preliminary Report on Patentability", dated Mar. 15, 2018, 7 pages.
PCT/US2016/050034, "International Search Report and Written Opinion", dated Oct. 28, 2016, 10 pages.
U.S. Appl. No. 15/757,317 , "Non-Final Office Action", dated Jun. 10, 2019, 9 pages.
EP16766747.6 , "Office Action", dated Feb. 28, 2019, 5 pages.
EP16767084.3 , "Office Action", dated Feb. 28, 2019, 5 pages.
EP16767424.1 , "Office Action", dated Mar. 1, 2019, 5 pages.
Graupner et al., "Spinosyn G: Proof of Structure by Semisynthesis", The Journal of Organic Chemistry; vol. 70, Issue 6, Mar. 18, 2005, pp. 2154-2160.
PCT/US2016/049879 , "Invitation to Pay Additional Fees and Where Applicable Protest Fee", dated Oct. 31, 2016, 6 pages.
U.S. Appl. No. 15/757,307 , "Non-Final Office Action", dated Nov. 20, 2019, 13 pages.
U.S. Appl. No. 15/757,317 , "Final Office Action", dated Nov. 12, 2019, 9 pages.
AU2016315860 , "First Examination Report", dated Oct. 23, 2019, 3 pages.
AU2016317848 , "First Examination Report", dated Oct. 25, 2019, 3 pages.

\* cited by examiner

SPINOSYN DERIVATIVES AS INSECTICIDES

CROSS-REFERENCE TO RELATED APPLICATIONS

This application is the U.S. national phase of International Application No. PCT/US2016/049870 filed on Sep. 1, 2016, and published on Mar. 9, 2017 as International Publication No. WO 2017/040763 A1, which application claims priority to and the benefit of U.S. Provisional Patent Application No. 62/214,083 filed Sep. 3, 2015; U.S. Provisional Patent Application No. 62/290,676 filed Feb. 3, 2016; U.S. Provisional Patent Application No. 62/303,015 filed Mar. 3, 2016; U.S. Provisional Patent Application No. 62/303,078 filed Mar. 3, 2016; and U.S. Provisional Patent Application No. 62/380,664 filed Aug. 29, 2016, the contents of all of which are incorporated herein by reference in their entireties.

FIELD

Described herein are spinosyn derivatives for use as agrichemicals.

BACKGROUND

Spinosyn refers to a large family of compounds produced from the fermentation of soil actinomycetes species of *Saccharopolyspora*. The individual components from the fermentation broth were subsequently given the generic name of spinosyn to connect these compounds with their producing microorganism, *Saccharopolyspora spinose*. Members of the spinosyn family share a core structure having a polyketide-derived tetracyclic macrolide appended with two saccharides. There are many naturally occurring variants, which exhibit potent insecticidal activities against many commercially significant species that cause extensive damage to crops and other plants. Some of these variants also exhibit activity against important external parasites of livestock, companion animals and humans.

Fermentation of *S. spinosa* produces a natural mixture containing spinosyn A as the major component and spinosyn D as the minor component and named spinosad. The structure of spinosyn A was determined by NMR, MS, and X-ray analyses and comprises a tetracyclic polyketide aglycone to which is attached a neutral saccharide substituent (2,3,4-tri-O-methyl-α-L-rhamnosyl) on the C-9 hydroxyl group and an aminosugar moiety (β-D-forosaminyl) on the C-17 hydroxyl group. This spinosyn tetracyclic ring system composed of a cis-anti-trans-5,6,5-tricyclic moiety fused to a 12-membered lactone is a unique ring system.

The second most abundant fermentation component is spinosyn D, which is 6-methyl-spinosyn A. Spinosyn D is likely formed by incorporation of propionate instead of acetate at the appropriate stage during polyketide assembly.

Numerous structurally related compounds from various spinosyn fermentations have now been isolated and identified. Their structures fall into several general categories of single-type changes in the aglycone or saccharides of spinosyn A.

Spinosyns have a unique mechanism of action (MOA) involving disruption of nicotinic acetylcholine receptors. When compared with many other insecticides, spinosyns generally show greater selectivity toward target insects and lesser activity against many beneficial predators. Structure-activity relationships (SARs) have been extensively studied, leading to development of a semisynthetic second-generation derivative, spinetoram (Kirst (2010) *J. Antibiotics* 63:101-111).

Studies to date have concluded that the mechanism(s) by which spinosyn exerts its insecticidal action is different from those of any other known agents, and thus cross-resistance between spinosyn and other agents was initially absent or low. However, as well known for other insecticides, continued usage is likely to exert selective pressures on insects and to eventually provoke resistance.

The unique and highly complex core structure of the spinosyns has provided challenging opportunities for synthesis. Additionally, with the increase of insect resistance, new spinosyn compounds and methods for their synthesis are needed.

SUMMARY

Spinosyn compounds and methods for making and using the spinosyn compounds are provided. The spinosyn compounds described herein exhibit activity towards insects, arachnids, and nematodes and are useful in the agricultural and animal health markets. The spinosyn compounds described herein exhibit activity comparable to or greater than the spinosyn-type natural products, often with an improved resistance profile over the natural products.

A spinosyn compound as described herein includes a compound of the following formula:

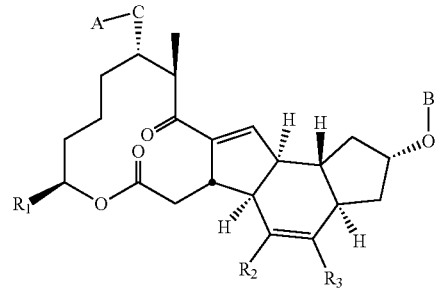

or a salt thereof, wherein A is selected from the group consisting of substituted or unsubstituted carbonyl, substituted or unsubstituted cycloalkyl, substituted or unsubstituted heterocycloalkyl, substituted or unsubstituted aryl, and substituted or unsubstituted heteroaryl; B is selected from the group consisting of substituted or unsubstituted cycloalkyl, substituted or unsubstituted heterocycloalkyl, substituted or unsubstituted aryl, and substituted or unsubstituted heteroaryl; C is O or NH; $R^1$ is substituted or unsubstituted alkyl, substituted or unsubstituted aryl; $R^2$ and $R^3$ are each independently selected from hydrogen, halogen, substituted or unsubstituted amino, substituted or unsubstituted alkoxy, substituted or unsubstituted aryloxy, substituted or unsubstituted alkyl, substituted or unsubstituted cycloalkyl, substituted or unsubstituted heterocycloalkyl, substituted or unsubstituted aryl, and substituted or unsubstituted heteroaryl, where $R^2$ and $R^3$ cannot both be hydrogen.

In some examples, A comprises forosamine or a forosamine derivative, such as [(2R,5S,6R)-6-methyl-5-(methylamino)oxan-2-yl]oxy-, B comprises rhamnose or a rhamnose derivative, such as 3,4,5-trimethoxyrhamnose or 4-ethoxy-3,5-dimethoxyrhamnose, C comprises oxygen, $R^1$ comprises ethyl, $R^2$ comprises halogen, substituted or unsubstituted phenyl, or substituted or unsubstituted phenyl triazole, wherein the substituted phenyl may have one or more substitutions including but not limited to halogen (e.g., chlorine, fluorine), alkyl (e.g., methyl, ethyl), halo alkyl (e.g., trifluoromethyl), alkoxy (e.g., methoxy, ethoxy), haloalkoxy (e.g. trifluoromethoxy), or ester (e.g., methyl ester), and wherein the substituted phenyl triazole may have one or more substitutions including but not limited to halogen (e.g., chlorine, fluorine), alkyl (e.g., methyl), alkoxy (e.g., methoxy), phenyl, and amino, and $R^3$ comprises hydrogen. In some examples, A comprises forosamine or a forosamine derivative, such as [(2R,5S,6R)-6-methyl-5-(methylamino)oxan-2-yl]oxy-, B comprises rhamnose or a rhamnose derivative, such as 3,4,5-trimethoxyrhamnose or 4-ethoxy-3,5-dimethoxyrhamnose, C comprises oxygen, $R^1$ comprises ethyl, $R^2$ comprises hydrogen and $R^3$ comprises substituted or unsubstituted phenyl, or substituted or unsubstituted phenyl triazole, wherein the substituted phenyl may have substitutions including but not limited to halogen (e.g., chlorine, fluorine), alkyl (e.g., methyl, ethyl), halo alkyl (e.g., trifluoromethyl), alkoxy (e.g., methoxy, ethoxy), haloalkoxy (e.g. trifluoromethoxy), or ester (e.g., methyl ester) and the substituted phenyl triazole may have substitutions on the phenyl ring including but not limited to halogen (e.g., chlorine, fluorine), alkyl (e.g., methyl), alkoxy (e.g., methoxy), phenyl, and amino. In some examples, A comprises forosamine or a forosamine derivative, such as [(2R,5S,6R)-6-methyl-5-(methylamino)oxan-2-yl]oxy-, B comprises rhamnose or a rhamnose derivative, such as 3,4,5-trimethoxyrhamnose or 4-ethoxy-3,5-dimethoxyrhamnose, C comprises oxygen, $R^1$ comprises ethyl, $R^2$ comprises hydrogen, and $R^3$ comprises a substituted or unsubstituted phenyl triazole. Optionally, the phenyl group of the substituted phenyl triazole is substituted with a halogen (e.g., chlorine, fluorine), alkyl (e.g., methyl), alkoxy (e.g., methoxy), phenyl, or amino moiety. Optionally, A comprises forosamine. Optionally, B comprises rhamnose or a rhamnose derivative, such as 3,4,5-trimethoxyrhamnose or 4-ethoxy-3,5-dimethoxyrhamnose.

In some examples, A is forosamine, B is 3,4,5-trimethoxyrhamnose, C is O, $R^1$ is ethyl, $R^2$ is chlorine and $R^3$ is hydrogen. In some examples, A is forosamine, B is 3,4,5-trimethoxyrhamnose, C is O, $R^1$ is ethyl, $R^2$ is hydrogen and $R^3$ is chlorine. Optionally, the spinosyn compound is (2S,5bS,9S,13S,14R,16aR,16bR)-5-chloro-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy})-1H,2H,3H,3aH,5aH,5bH,6H,7H,9H,10H,11H,12H,13H,14H,15H,16aH,16bH-as-indaceno[3,2-d]oxacyclododecane-7,15-dione, or (2S,5bS,9S,13S,14R,16aS,16bS)-4-chloro-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,3aH,5aH,5bH,6H,7H,9H, 10H, 11H,12H,13H, 14H, 15H, 16aH, 16bH-as-indaceno[3,2-d]oxacyclododecane-7,15-dione, respectively.

In some examples, A is forosamine, B is 3,4,5-trimethoxyrhamnose, C is O, $R^1$ is ethyl, $R^2$ is hydrogen, and $R^3$ is 4-methoxyphenyl. In some examples, A is forosamine, B is 3,4,5-trimethoxyrhamnose, C is O, $R^1$ is ethyl, $R^2$ is 4-methoxyphenyl, and $R^3$ is hydrogen. Optionally, the spinosyn compound is (2S,5bS,9S,13S,14R,16aR,16bR)-13-{[(2R,5S,6R)-5-(dimethylamino)-6-methyloxan-2-yl]oxy}-9-ethyl-5-(4-methoxyphenyl)-14-methyl-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione, or (2S,5bS,9S,13S,14R,16aS,16bS)-13-{[(2R,5S,6R)-5-(dimethylamino)-6-methyloxan-2-yl]oxy})-9-ethyl-4-(4-methoxyphenyl)-14-methyl-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione.

In some examples, A is forosamine, B is 3,4,5-trimethoxyrhamnose, C is O, $R^1$ is ethyl, $R^2$ is hydrogen, and $R^3$ is phenyl. In some examples, A is forosamine, B is 3,4,5-trimethoxyrhamnose, C is O, $R^1$ is ethyl, $R^2$ is phenyl, and $R^3$ is hydrogen. Optionally, the spinosyn compound is (2S,5bS,9S,13S,14R,16aS,16bS)-13-{[(2R,5S,6R)-5-(dimethylamino)-6-methyloxan-2-yl]oxy}-9-ethyl-14-methyl-4-phenyl-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione or (2S,5bS,9S,13S,14R,16aR,16bR)-13-{[(2R,5S,6R)-5-(dimethylamino)-6-methyloxan-2-yl]oxy}-9-ethyl-14-methyl-5-phenyl-2-{[(2R,3R,4R,5S,6S)-3,4,5-trimethoxy-6-methyloxan-2-yl]oxy}-1H,2H,3H,3 aH, 5 aH,5bH,6H,7H,9H,10H,11H,12H,13H,14H,15H,16aH,16bH-as-indaceno[3,2-d]oxacyclododecane-7,15-dione.

In some examples, A is forosamine, B is 3,4,5-trimethoxyrhamnose, C is O, $R^1$ is ethyl, $R^3$ is hydrogen, and $R^2$ is 3-chlorophenyl. In some examples, A is forosamine, B is 3,4,5-trimethoxyrhamnose, C is O, $R^1$ is ethyl, $R^2$ is hydrogen, and $R^3$ is 3-chlorophenyl. Optionally, the spinosyn compound is (2S,5bS,9S,13S,14R,16aR,16bR)-5-(3-chlorophenyl)-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,3 aH,5a-H,5bH,6H,7H,9H,10H,11H,12H,13H,14H,15H,16aH,16bH-as-indaceno[3,2-d]oxacyclododecane-7,15-dione or (2S,5bS,9S,13S,14R,16aS,16bS)-4-(3-chlorophenyl)-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione.

In some examples, A is forosamine, B is 3,4,5-trimethoxyrhamnose, C is O, $R^1$ is ethyl, $R^2$ is 3-methoxyphenyl, and $R^3$ is hydrogen. In some examples, A is forosamine, B is 3,4,5-trimethoxyrhamnose, C is O, $R^1$ is ethyl, $R^2$ is hydrogen, and $R^3$ is 3-methoxyphenyl. Optionally, the spinosyn compound is (2S,5bS,9S,13S,14R,16aR,16bR)-13-{[(2R,5S,6R)-5-(dimethylamino)-6-methyloxan-2-yl]oxy}-9-ethyl-5-(3-methoxyphenyl)-14-methyl-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione or (2S,5bS,9S,13S, 14R, 16aS,16bS)-13-{[(2R,5S,6R)-5-(dimethylamino)-6-methyloxan-2-yl]oxy}-9-ethyl-4-(3-methoxyphenyl)-14-methyl-2-{[(2R,3R,4R,5S,6S)-3,4,5-trimethoxy-6-methyloxan-2-yl]oxy}-1H,2H,3H,3 aH, 5 aH,5bH,6H,7H,9H, 10H, 11H, 12H, 13H, 14H, 15H, 16aH, 16bH-as-indaceno[3,2-d]oxacyclododecane-7,15-dione.

In some examples, A is forosamine, B is 3,4,5-trimethoxyrhamnose, C is O, $R^1$ is ethyl, $R^2$ is 3-fluorophenyl, and $R^3$ is hydrogen. In some examples, A is forosamine, B is 3,4,5-trimethoxyrhamnose, C is O, $R^1$ is ethyl, $R^2$ is hydrogen, and $R^3$ is 3-fluorophenyl. Optionally, the spinosyn compound is (2S,5bS,9S,13S,14R,16aR,16bR)-5-(3-fluorophenyl)-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,3 aH,5aH,5bH,6H,7H,9H,10H,11H,12H,13H,14H,15H,16aH, 16bH-as-indaceno[3,2-d]oxacyclododecane-7,15-dione or (2S,5bS,9S,13S, 14R, 16aR,16bR)-4-(3-fluorophenyl)-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione.

In some examples, A is forosamine, B is 3,4,5-trimethoxyrhamnose, C is O, $R^1$ is ethyl, $R^3$ is hydrogen, and $R^2$ is 4-chlorophenyl. In some examples, A is forosamine, B is 3,4,5-trimethoxyrhamnose, C is O, $R^1$ is ethyl, $R^2$ is hydrogen, and $R^3$ is 4-chlorophenyl. Optionally, the spinosyn compound is (2S,5bS,9S,13S,14R,16aS,16bS)-4-(4-chlorophenyl)-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione or (2S,5bS,9S,13S,14R,16aR,16bR)-5-(4-chlorophenyl)-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,3 aH, 5aH,5bH,6H,7H,9H,10H,11H,12H,13H,14H,15H,16aH,16bH-as-indaceno[3,2-d]oxacyclodecane-7,15-dione.

In some examples, A is forosamine, B is 3,4,5-trimethoxyrhamnose, C is O, $R^1$ is ethyl, $R^3$ is hydrogen, and $R^2$ is 4-(trifluoromethoxy)phenyl. In some examples, A is forosamine, B is 3,4,5-trimethoxyrhamnose, C is O, $R^1$ is ethyl, $R^3$ is 4-(trifluoromethoxy)phenyl, and $R^2$ is hydrogen. Optionally, the spinosyn compound is (2S,5bS,9S,13S, 14R, 16aR, 16bR)-13-{[(2R,5S,6R)-5-(dimethylamino)-6-methyloxan-2-yl]oxy}-9-ethyl-14-methyl-5-[4-(trifluoromethoxy)phenyl]-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione or (2S,5bS,9S,13S,14R,16aR,16bR)-13-{[(2R,5S,6R)-5-(dimethylamino)-6-methyloxan-2-yl]oxy}-9-ethyl-4-[4-(trifluoromethoxy)phenyl]-14-methyl-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione.

In some examples, A is forosamine, B is rhamnose 3,4,5-trimethoxyrhamnose, C is O, $R^1$ is ethyl, $R^2$ is 4-(trifluoromethyl)phenyl, and $R^3$ is hydrogen. In some examples, A is forosamine, B is 3,4,5-trimethoxyrhamnose, C is O, $R^1$ is ethyl, $R^2$ is hydrogen, and $R^3$ is 4-(trifluoromethyl)phenyl. Optionally, the spinosyn compound is (2S,5bS,9S,13S,14R,16aR,16bR)-13-{[(2R,5S,6R)-5-(dimethylamino)-6-methyloxan-2-yl]oxy}-9-ethyl-14-methyl-5-[4-(trifluoromethyl)phenyl]-2-{[(2R,3R,4R,5S,6S)-3,4,5-trimethoxy-6-methyloxan-2-yl]oxy}-1H,2H,3H,3 aH,5aH,5bH,6H,7H,9H, 10H, 11H,12H,13H, 14H, 15H, 16aH, 16bH-as-indaceno[3,2-d]oxacyclododecane-7,15-dione or (2S,5bS,9S,13S,14R,16aS,16bS)-4-(4-(trifluoromethyl)phenyl)-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,3aH,5aH,5bH,6H,7H,9H, 10H, 11H, 12H, 13H,14H, 15H, 16aH, 16bH-as-indaceno[3,2-d]oxacyclododecane-7,15-dione.

In some examples, A is forosamine, B is 3,4,5-trimethoxyrhamnose, C is O, $R^1$ is ethyl, $R^2$ is 4-ethylphenyl, and $R^3$ is hydrogen. In some examples, A is forosamine, B is 3,4,5-trimethoxyrhamnose, C is O, $R^1$ is ethyl, $R^2$ is hydrogen, and $R^3$ is 4-ethylphenyl. Optionally, the spinosyn compound is (2S,5bS,9S,13S,14R,16aR,16bR)-13-{[(2R,5S,6R)-5-(dimethylamino)-6-methyloxan-2-yl]oxy}-9-ethyl-5-(4-ethylphenyl)-14-methyl-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione, or (2S,5bS,9S,13S,14R,16aS,16bS)-4-(4-ethylphenyl)-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione.

In some examples, A is forosamine, B is 3,4,5-trimethoxyrhamnose, C is O, $R^1$ is ethyl, $R^2$ is methyl benzoate, and $R^3$ is hydrogen. In some examples, A is forosamine, B is 3,4,5-trimethoxyrhamnose, C is O, $R^1$ is ethyl, $R^2$ is hydrogen, and $R^3$ is methyl benzoate. Optionally, the spinosyn compound is methyl 4-[(2S,5bS,9S,13S,14R,16aR,16bR)-13-{[(2R,5S,6R)-5-(dimethylamino)-6-methyloxan-2-yl]oxy}-9-ethyl-14-methyl-7,15-dioxo-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecan-5-yl]benzoate.

In some examples, A is forosamine, B is 3,4,5-trimethoxyrhamnose, C is O, $R^1$ is ethyl, $R^2$ is a 4-fluorophenyl trizaole, and $R^3$ is hydrogen. In some examples, A is forosamine, B is 3,4,5-trimethoxyrhamnose, C is O, $R^1$ is ethyl, $R^2$ is hydrogen, and $R^3$ is a 4-fluorophenyl triazole. Optionally, the spinosyn compound is (2S,3aR,5aR,5bS,9S,13S,14R,16aS,16bS)-13-{[(2R,5S,6R)-5-(dimethylamino)-6-methyloxan-2-yl]oxy}-9-ethyl-4-[4-(4-fluorophenyl)-1H-1,2,3-triazol-1-yl]-14-methyl-2-{[(2R,3R,4R,5S,6S)-3,4,5-trimethoxy-6-methyloxan-2-yl]oxy}-1H,2H,3H,3 aH,5aH,5bH, 6H,7H,9H,10H,11H,12H,13H,14H,15H,16aH,16bH-as-indaceno[3,2-d]oxacyclododecane-7,15-dione.

In some examples, A is forosamine, B is 3,4,5-trimethoxyrhamnose, C is O, $R^1$ is ethyl, $R^2$ is 4-methoxyphenyl trizaole, and $R^3$ is hydrogen. In some examples, A is forosamine, B is 3,4,5-trimethoxyrhamnose, C is O, $R^1$ is ethyl, $R^2$ is hydrogen, and $R^3$ is 4-methoxyphenyl triazole. Optionally, the spinosyn compound is (2S,3aR,5aR,5bS,9S,13S,14R,16aS,16bS)-13-{[(2R,5S,6R)-5-(dimethylamino)-6-methyloxan-2-yl]oxy}-9-ethyl-4-[4-(4-methoxyphenyl)-1H-1,2,3-triazol-1-yl]-14-methyl-2-{[(2R,3R,4R,5S,6S)-3,4,5-trimethoxy-6-methyloxan-2-yl]oxy}-1H,2H,3H,3 aH,5aH,5bH, 6H,7H,9H,10H,11H,12H,13H,14H,15H,16aH,16bH-as-indaceno[3,2-d]oxacyclododecane-7,15-dione.

In some examples, A is forosamine, B is 3,4,5-trimethoxyrhamnose, C is O, $R^1$ is ethyl, $R^2$ is phenyl trizaole, and $R^3$ is hydrogen. In some examples, A is forosamine, B is 3,4,5-trimethoxyrhamnose, C is O, $R^1$ is ethyl, $R^2$ is hydrogen, and $R^3$ is phenyl trizaole. Optionally, the spinosyn compound is (2S,3aR,5aR,5bS,9S,13S,14R,16aS,16bS)-13-{[(2R,5S,6R)-5-(dimethylamino)-6-methyloxan-2-yl]oxy}-9-ethyl-14-methyl-4-(4-phenyl-1H-1,2,3-triazol-1-yl)-2-{[(2R,3R,4R,5S,6S)-3,4,5-trimethoxy-6-methyloxan-2-yl]oxy}-1H,2H,3H,3 aH,5aH,5bH,6H,7H,9H,10H,11H,12H,13H,14H,15H,16aH,16bH-as-indaceno[3,2-d]oxacyclododecane-7,15-dione.

In some examples, A is forosamine, B is 3,4,5-trimethoxyrhamnose, C is O, $R^1$ is ethyl, $R^2$ is 3-methylphenyl trizaole, and $R^3$ is hydrogen. In some examples, A is forosamine, B is 3,4,5-trimethoxyrhamnose, C is O, $R^1$ is ethyl, $R^2$ is hydrogen, and $R^3$ is 3-methylphenyl triazole. Optionally, the spinosyn compound is (2S,3aR,5aR,5bS,9S,13S,14R,16aS,16bS)-13-{[(2R,5S,6R)-5-(dimethylamino)-6-methyloxan- 2-yl]oxy}-9-ethyl-14-methyl-4-[4-(3-methylphenyl)-1H-1,2,3-triazol-1-yl]-2-{[(2R,3R,4R,5S,6S)-3,4,5-trimethoxy-6-methyloxan-2-yl]oxy}-1H,2H,3H,3aH, 5aH,5bH,6H,7H,9H, 10H,11H,12H,13H,14H,15H,16aH,16bH-as-indaceno[3,2-d]oxacyclo dodecane-7,15-dion.

In some examples, A is [(2R,5S,6R)-6-methyl-5-(methylamino)oxan-2-yl]oxy-, B is 3,4,5-trimethoxyrhamnose, C is O, $R^1$ is ethyl, $R^3$ is hydrogen, and $R^2$ is 3-methylphenyl trizaole. In some examples, A is [(2R,5S,6R)-6-methyl-5-(methylamino)oxan-2-yl]oxy-, B is 3,4,5-trimethoxyrhamnose, C is O, $R^1$ is ethyl, $R^2$ is hydrogen, and $R^3$ is 3-methylphenyl triazole. Optionally, the spinosyn compound is (2S,3aR,5aR,5bS,9S,13S,14R,16aS,16bS)-13-{[(2R,5S,6R)-5-(dimethylamino)-6-methyloxan-2-yl]oxy}-9-ethyl-14-methyl-4-[4-(3-methylphenyl)-1H-1,2,3-triazol-1-yl]-2-{[(2R,3R,4R,5S,6S)-3,4,5-trimethoxy-6-methyloxan-2-yl]oxy}-1H,2H,3H,3aH, 5aH,5bH,6H,7H,9H,10H,11H,12H,13H,14H,15H,16aH,16bH-as-indaceno[3,2-d]oxacyclo dodecane-7,15-dion.

In some examples, A is [(2R,5S,6R)-6-methyl-5-(methylamino)oxan-2-yl]oxy-, B is 3,4,5-trimethoxyrhamnose, C is O, $R^1$ is ethyl, $R^2$ is 3-methoxyphenyl trizaole, and $R^3$ is hydrogen. In some examples, A is [(2R,5S,6R)-6-methyl-5-(methylamino)oxan-2-yl]oxy-, B is 3,4,5-trimethoxyrhamnose, C is O, $R^1$ is ethyl, $R^2$ is hydrogen, and $R^3$ is 3-methoxyphenyl triazole. Optionally, the spinosyn compound is (2S,3aR,5aR,5bS,9S,13S,14R,16aS,16bS)-9-ethyl-4-[4-(4-methoxyphenyl)-1H-1,2,3-triazol-1-yl]-14-methyl-13-{[(2R,5S,6R)-6-methyl-5-(methylamino)oxan-2-yloxy})-2-{[(2R,3R,4R,5S,6S)-3,4,5-trimethoxy-6-methyloxan-2-yl]oxy}-1H,2H,3H,3 aH, 5aH,5bH, 6H,7H,9H,10H,11H,12H,13H,14H,15H,16aH,16bH-as-indaceno[3,2-d]oxacyclododecane-7,15-dione.

In some examples, A is forosamine, B is 3,4,5-trimethoxyrhamnose, C is O, $R^1$ is ethyl, $R^2$ is 1,1'-biphenyl trizaole, and $R^3$ is hydrogen. In some examples, A is forosamine, B is 3,4,5-trimethoxyrhamnose, C is O, $R^1$ is ethyl, $R^2$ is hydrogen, and $R^3$ is 1,1'-biphenyl triazole. Optionally, the spinosyn compound is (2S,3aR,5aR,5bS,9S,13S,14R,16aS,16bS)-4-(4-{[1,1'-biphenyl]-4-yl}-1H-1,2,3-triazol-1-yl)-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,3aH,5aH, 5bH,6H,7H,9H,10H,11H,12H,13H,14H,15H,16aH,16bH-as-indaceno[3,2-d]oxacyclododecane-7,15-dione.

In some examples, A is forosamine, B is 3,4,5-trimethoxyrhamnose, C is O, $R^1$ is ethyl, $R^2$ is 3-aminophenyl trizaole, and $R^3$ is hydrogen. In some examples, A is forosamine, B is 3,4,5-trimethoxyrhamnose, C is O, $R^1$ is ethyl, $R^2$ is hydrogen, and $R^3$ is 3-aminophenyl triazole. Optionally, the spinosyn compound is (2S,3aR,5aR,5bS,9S,13S,14R,16aS,16bS)-4-[4-(3-aminophenyl)-1H-1,2,3-triazol-1-yl]-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,3aH,5aH, 5bH,6H,7H, 9H,10H,11H,12H,13H,14H,15H,16aH,16bH-as-indaceno[3,2-d]oxacyclododecane-7,15-dione.

In some examples, A is forosamine, B is 3,4,5-trimethoxyrhamnose, C is O, $R^1$ is ethyl, $R^2$ is 4-aminophenyl trizaole, and $R^3$ is hydrogen. In some examples, A is forosamine, B is 3,4,5-trimethoxyrhamnose, C is O, $R^1$ is ethyl, $R^2$ is hydrogen, and $R^3$ is 4-aminophenyl triazole. Optionally, the spinosyn compound is (2S,3aR,5aR,5bS,9S,13S,14R,16aS,16bS)-4-[4-(4-aminophenyl)-1H-1,2,3-triazol-1-yl]-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,3aH,5aH, 5bH,6H,7H, 9H,10H,11H,12H,13H,14H,15H,16aH,16bH-as-indaceno[3,2-d]oxacyclododecane-7,15-dione.

In some examples, A is forosamine, B is 3,4,5-trimethoxyrhamnose, C is O, $R^1$ is ethyl, $R^2$ is 2-chlorophenyl triazole, $R^3$ is hydrogen. In some examples, A is forosamine, B is 3,4,5-trimethoxyrhamnose, C is O, $R^1$ is ethyl, $R^2$ is hydrogen, and $R^3$ is 2-chlorophenyl trizaole. Optionally, the spinosyn compound is (2S,3aR,5aR,5bS,9S,13S,14R,16aS,16bS)-4-[4-(3-chlorophenyl)-1H-1,2,3-triazol-1-yl]-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,3aH,5aH, 5bH,6H,7H, 9H,10H,11H,12H,13H,14H,15H,16aH,16bH-as-indaceno[3,2-d]oxacyclododecane-7,15-dione.

In some examples, A is forosamine, B is 3,4,5-trimethoxyrhamnose, C is O, $R^1$ is ethyl, $R^2$ is fluorine, and $R^3$ is 4-phenyl trizaole. In some examples, A is forosamine, B is 3,4,5-trimethoxyrhamnose, C is O, $R^1$ is ethyl, $R^3$ is 4-phenyl triazole, and $R^2$ is fluorine. Optionally, the spinosyn compound is (2S,3aR,9S,13S,14R,16aR,16bS)-13-{[(2R,5S,6R)-5-(dimethylamino)-6-methyloxan-2-yl]oxy}-9-ethyl-5-fluoro-14-methyl-4-(4-phenyl-1H-1,2,3-triazol-1-yl)-2-{[(2R,3R,4R,5S,6 S)-3,4,5-trimethoxy-6-methyloxan-2-yl]oxy}-1H,2H,3H,3 aH,5aH,5bH,6H,7H,9H,10H,11H,12H,13H,14H,15H,16aH,16bH-as-indaceno[3,2-d]oxacyclododecane-7,15-dione.

Also described herein are formulations. A formulation as described herein comprises at least one spinosyn compound as described herein and an acceptable carrier. Optionally, the formulation can further comprise at least one additional active ingredient and/or at least one plant or plant product treatment compound. The at least one additional active ingredient can comprise, for example, an insecticide or a miticide (e.g., a contact-acting insecticide or contact-acting miticide).

Further described herein is a method for controlling pests. A method for controlling pests as described herein comprises contacting a pest with an effective amount of a spinosyn compound or a formulation as described herein. Optionally, the pest is an insect, an arachnid, or a nematode.

Also described herein are methods for making a spinosyn compound. A method for making a spinosyn compound comprises reacting the C-13,14 double bond of spinosyn A to form a spinosyn compound according to claim 1, wherein the spinosyn compound forms via a [3+2] cycloaddition product.

The details of one or more embodiments are set forth in the drawings and the description below. Other features, objects, and advantages will be apparent from the description and drawings, and from the claims.

DETAILED DESCRIPTION

Provided herein are spinosyn compounds. The compositions are useful in the agricultural and animal health markets having activity towards pests such as insects, arachnids, nematodes and the like. Methods for making the compounds are also provided.

I. Compounds

A class of spinosyn compounds described herein is represented by Formula I:

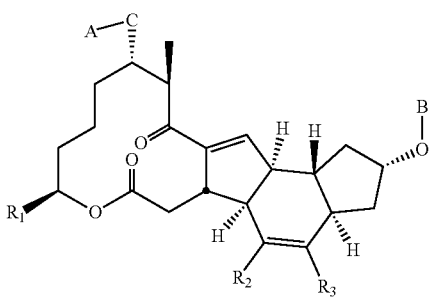

In Formula I, A is selected from the group consisting of substituted or unsubstituted carbonyl, substituted or unsubstituted cycloalkyl, substituted or unsubstituted heterocycloalkyl, substituted or unsubstituted aryl, and substituted or unsubstituted heteroaryl. Optionally, A can be a substituted or unsubstituted saccharide. For example, A can be forosamine or a forosamine derivative, such as [(2R,5S,6R)-6-methyl-5-(methylamino)oxan-2-yl]oxy-.

Additionally, in Formula I, B is selected from the group consisting of substituted or unsubstituted cycloalkyl, substituted or unsubstituted heterocycloalkyl, substituted or unsubstituted aryl, and substituted or unsubstituted heteroaryl. Optionally, B can be a substituted or unsubstituted saccharide. For example, B can be rhamnose or a rhamnose derivative.

Optionally, B can include 3,4,5-trimethoxyrhamnose (tri-O-methyl rhamnose) or 4-ethoxy-3,5-dimethoxyrhamnose.

Further, in Formula I, C is O or NH.

Also, in Formula I, $R^1$ is substituted or unsubstituted alkyl, substituted or unsubstituted aryl. Optionally, $R^1$ is ethyl.

Also in Formula I, $R^2$ and $R^3$ are each independently selected from hydrogen, halogen, substituted or unsubstituted amino, substituted or unsubstituted alkoxy, substituted or unsubstituted aryloxy, substituted or unsubstituted alkyl, substituted or unsubstituted cycloalkyl, substituted or unsubstituted heterocycloalkyl, substituted or unsubstituted aryl, and substituted or unsubstituted heteroaryl, where $R^2$ and $R^3$ cannot both be hydrogen.

In some examples, A comprises forosamine, B comprises rhamnose or a rhamnose derivative, such as 3,4,5-trimethoxyrhamnose or 4-ethoxy-3,5-dimethoxyrhamnose, C comprises oxygen, $R^1$ comprises ethyl, $R^2$ comprises chloro, methoxyphenyl, phenyl, chlorophenyl, fluorophenyl, or trifluoromethoxyphenyl, and $R^3$ comprises hydrogen. In some examples, A comprises forosamine, B comprises rhamnose or a rhamnose derivative, such as 3,4,5-trimethoxyrhamnose or 4-ethoxy-3,5-dimethoxyrhamnose, C comprises oxygen, $R^1$ comprises ethyl, $R^2$ comprises hydrogen and $R^3$ comprises chloro, methoxyphenyl, ethylphenyl, phenyl, chlorophenyl, fluorophenyl, trifluoromethoxyphenyl, or methyl benzoate. In some examples, A comprises forosamine, B comprises rhamnose or a rhamnose derivative, such as 3,4,5-trimethoxyrhamnose or 4-ethoxy-3,5-dimethoxyrhamnose, C comprises oxygen, $R^1$ comprises ethyl, $R^2$ comprises chloro, methoxyphenyl, ethylphenyl, phenyl, chlorophenyl, fluorophenyl, trifluoromethoxyphenyl or methyl benzoate, and $R^3$ comprises hydrogen. In some examples, A comprises forosamine or a forosamine derivative, such as [(2R,5S,6R)-6-methyl-5-(methylamino)oxan-2-yl]oxy-, B comprises rhamnose or a rhamnose derivative, such as 3,4,5-trimethoxyrhamnose or 4-ethoxy-3,5-dimethoxyrhamnose, C comprises oxygen, $R^1$ comprises ethyl, $R^2$ comprises hydrogen, and $R^3$ comprises a triazole. In some examples, A comprises forosamine or a forosamine derivative, such as [(2R,5S,6R)-6-methyl-5-(methylamino)oxan-2-yl]oxy-, B comprises rhamnose or a rhamnose derivative, such as 3,4,5-trimethoxyrhamnose or 4-ethoxy-3,5-dimethoxyrhamnose, C comprises oxygen, $R^1$ comprises ethyl, $R^2$ comprises hydroxy, and $R^3$ comprises a triazole. Optionally, the triazole is substituted with a phenyl, methylphenyl, methoxyphenyl, biphenyl, aminophenyl, or chlorophenyl moiety.

Optionally, A, B, C, and $R^1$ are as described above for Formula I, and $R^2$ is hydrogen and $R^3$ is an unsubstituted or substituted phenyl. In some examples, A is forosamine, B is 3,4,5-trimethoxyrhamnose, C is O, $R^1$ is ethyl, $R^2$ is hydrogen and $R^3$ is an unsubstituted or substituted phenyl. In these examples, Formula I can be represented by Structure I-A:

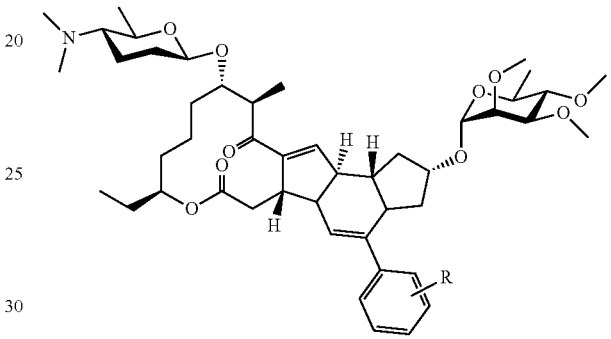

wherein R is selected from hydrogen, alkoxy, alkyl, halogen, halogenated alkoxy, or methyl acetate. Thus, the phenyl group may comprise a methoxyphenyl, ethylphenyl, phenyl, chlorophenyl, fluorophenyl, trifluoromethoxyphenyl or methyl benzoate moiety.

Optionally, A, B, C, and $R^1$ are as described above for Formula I and, $R^2$ is an unsubstituted or substituted phenyl and $R^3$ is hydrogen. In some examples, A is forosamine, B is 3,4,5-trimethoxyrhamnose, C is O, $R^1$ is ethyl, $R^2$ is an unsubstituted or substituted phenyl and $R^3$ is hydrogen. In these examples, Formula I can be represented by Structure I-B:

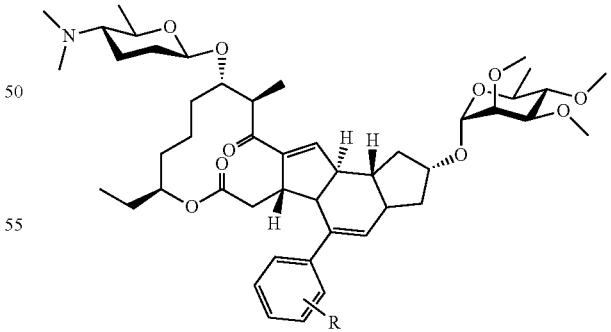

wherein R is selected from hydrogen, alkoxy, alkyl, halogen, halogenated alkoxy, or methyl acetate. Thus, the phenyl group may comprise a methoxyphenyl, ethylphenyl, phenyl, chlorophenyl, fluorophenyl, trifluoromethoxyphenyl or methyl benzoate moiety.

Optionally, A, B, C, and $R^1$ are as described above for Formula I, and $R^2$ is hydrogen and $R^3$ is an unsubstituted or substituted triazole. In some examples, A is forosamine, B is 3,4,5-trimethoxyrhamnose, C is O, $R^1$ is ethyl, $R^2$ is hydrogen and $R^3$ is an unsubstituted or substituted phenyl triazole. In these examples, Formula I can be represented by Structure I-C:

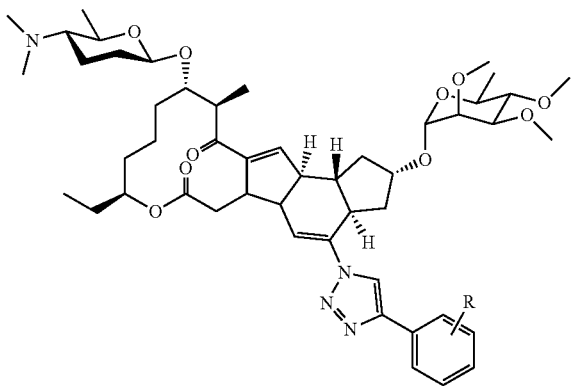

wherein R is selected from alkyl, alkoxy, aryl, amino, or halogen. Thus, triazole may be substituted with phenyl, methylphenyl, methoxyphenyl, aminophenyl, chlorophenyl, or fluorophenyl.

Optionally, A is forosamine, B is 3,4,5-trimethoxyrhamnose, C is O, $R^1$ is ethyl, $R^2$ is hydrogen and $R^3$ is chlorine. The spinosyn compound can be, for example, (2S,5bS,9S,13S,14R,16aS,16bS)-4-chloro-13-{[(2R,5S,6R)-5-(dimethylamino)-6-methyloxan-2-yl]oxy}-9-ethyl-14-methyl-2-{[(2R,3R,4R,5S, 6 S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione.

Optionally, A is forosamine, B is 3,4,5-trimethoxyrhamnose, C is O, $R^1$ is ethyl, $R^2$ is hydrogen and $R^3$ is phenyl. The spinosyn compound can be, for example, (2S, 5bS,9S,13S,14R,16aS,16bS)-13-{[(2R,5S,6R)-5-(dimethylamino)-6-methyloxan-2-yl]oxy}-9-ethyl-14-methyl-4-phenyl-2-{[(2R,3R,4R,5S,6S)-3,4,5-trimethoxy-6-methyloxan-2-yl]oxy}-4-1H,2H,3H,3aH,5aH,5bH,6H,7H,9H,10H,11H,12H,13H,14H,15H,16aH,16bH-as-indaceno[3,2-d]oxacyclododecane-7,15-dione.

Optionally, A is forosamine, B is 3,4,5-trimethoxyrhamnose, C is O, $R^1$ is ethyl, $R^2$ is hydrogen and $R^3$ is 4-methoxyphenyl. The spinosyn compound can be, for example, (2S,5bS,9S,13S, 14R, 16aS,16bS)-13-{[(2R,5S,6R)-5-(dimethylamino)-6-methyloxan-2-yl]oxy}-9-ethyl-4-(4-methoxyphenyl)-14-methyl-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione.

Optionally, A is forosamine, B is 3,4,5-trimethoxyrhamnose, C is O, $R^1$ is ethyl, $R^2$ is hydrogen and $R^3$ is phenyl triazole. The spinosyn compound can be, for example, (2S,3aR,5aR,5bS,9S,13S,14R,16aS,16bS)-13-{[(2R,5S,6R)-5-(dimethylamino)-6methyloxan-2-yl]oxy}-9-ethyl-14-methyl-4-(4-phenyl-1H-1,2,3-triazol-1-yl)-2-{[(2R,3R,4R,5S,6S)-3,4,5-trimethoxy-6-methyloxan-2-yl]oxy})-1H,2H,3H,3aH,5aH,5bH,6H,7H,9H, 10H, 11H, 12H, 13H, 14H, 15H, 16aH, 16bH-as-indaceno[3,2-d]oxacyclododecane-7,15-dione.

Optionally, A is forosamine, B is 3,4,5-trimethoxyrhamnose, C is O, $R^1$ is ethyl, $R^2$ is hydrogen and $R^3$ is methoxyphenyl triazole. The spinosyn compound can be, for example, (2S,3aR,5aR,5bS,9S,13S,14R,16aS,16bS)-9-ethyl-4-[4-(4-methoxyphenyl)-1H-1,2,3-triazol-1-yl]-14-methyl-13-{[(2R,5S,6R)-6-methyl-5-(methylamino)oxan-2-yl]oxy}-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione.

Optionally, A is forosamine, B is 4-ethoxy-3,5-dimethoxyrhamnose, C is O, $R^1$ is ethyl, $R^2$ is hydrogen and $R^3$ is phenyl. The spinosyn compound can be, for example, (2S,5bS,9S,13S, 14R, 16aS,16bS)-13-{[(2R,5S,6R)-5-(dimethylamino)-6-methyloxan-2-yl]oxy}-2-{[(2R,3R,4R,5S,6S)-4-ethoxy-3,5-dimethoxy-6-methyloxan-2-yl]oxy}-9-ethyl-14-methyl-4-phenyl-1H,2H,3H,3aH,5aH,5bH,6H,7H,9H,10H,11H,12H,13H,14H,15H,16aH,16bH-as-indaceno[3,2-d]oxacyclododecane-7,15-dione.

Optionally, A is forosamine, B is 4-ethoxy-3,5-dimethoxyrhamnose, C is O, $R^1$ is ethyl, $R^2$ is hydrogen and $R^3$ is a phenyltriazole. The spinosyn compound can be, for example, (2S,5bS,9S,13S,14R,16aS,16bS)-13-{[(2R,5S,6R)-5-(dimethylamino)-6-methyloxan-2-yl]oxy}-2-{[(2R,3R,4R,5S,6S)-4-ethoxy-3,5-dimethoxy-6-methyloxan-2-yl]oxy}-9-ethyl-14-methyl-4-(4-phenyl-1H-1,2,3-triazol-1-yl)-1H,2H,3H,3aH,5aH,5bH,6H,7H,9H,10H,11H,12H,13H,14H,15H,16aH,16bH-as-indaceno[3,2-d]oxacyclododecane-7,15-dione.

Examples of Formula I include the compounds shown in Table 1. In Table 1 the compound number is shown to the left of the corresponding compound.

TABLE 1

| No. | Structure |
|---|---|
| 1 | 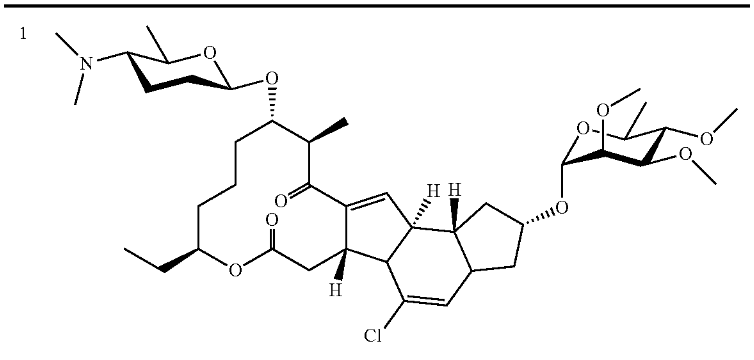 |

TABLE 1-continued

| No. | Structure |
|---|---|
| 2 | 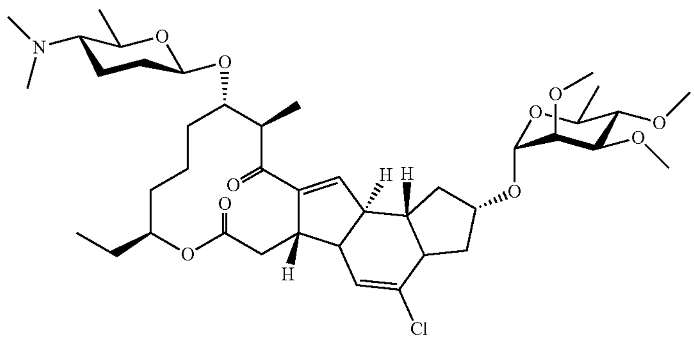 |
| 3 | 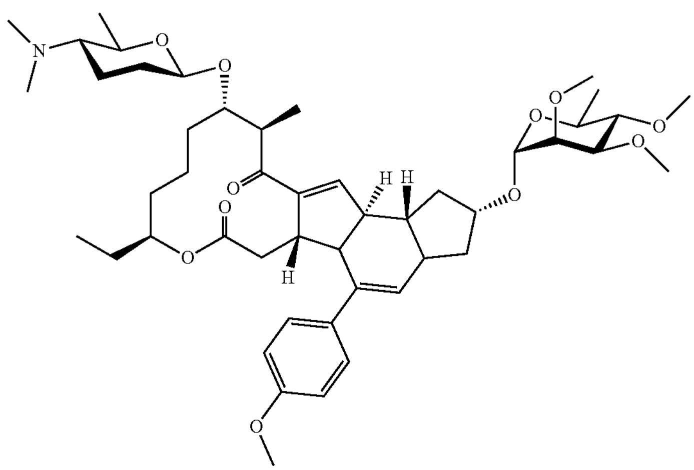 |
| 4 | 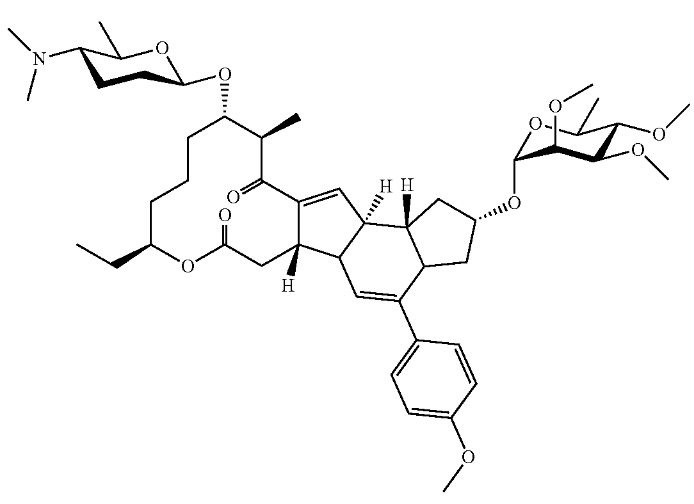 |

TABLE 1-continued

| No. | Structure |
| --- | --- |
| 5 | 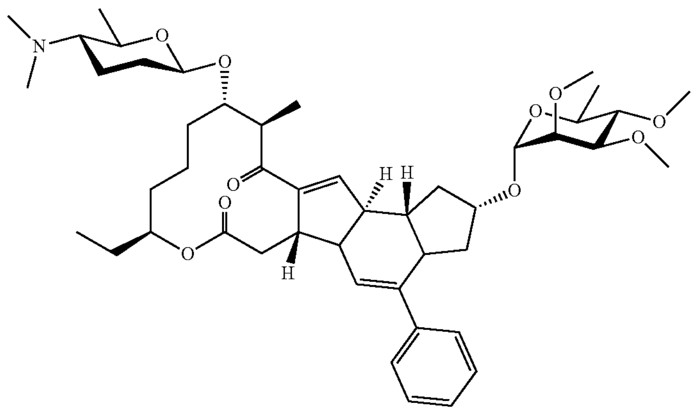 |
| 6 | 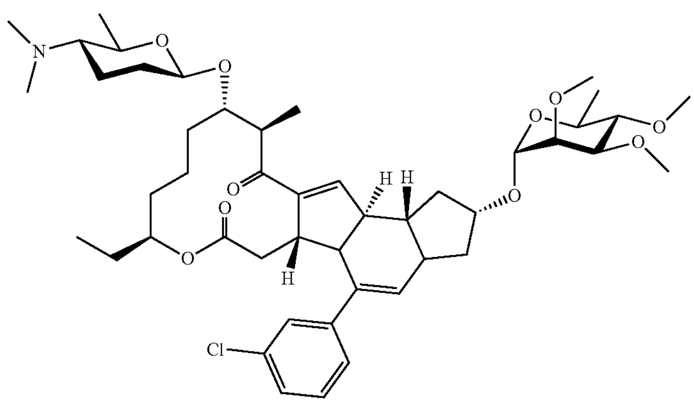 |
| 7 | 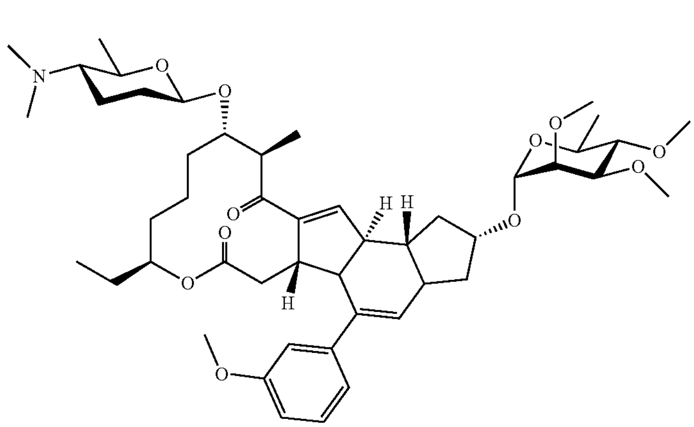 |

TABLE 1-continued

| No. | Structure |
|---|---|
| 8 | 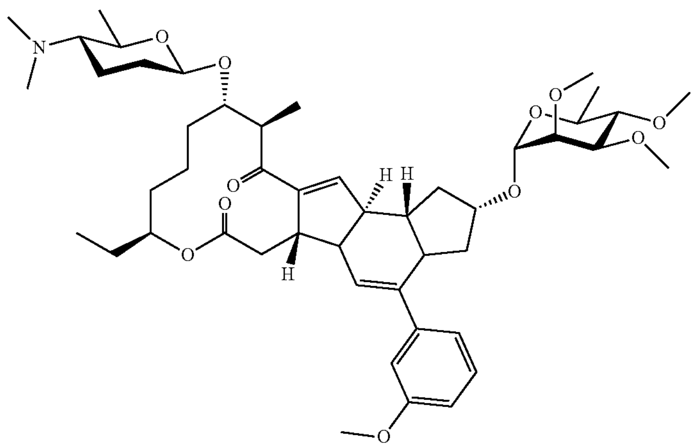 |
| 9 | 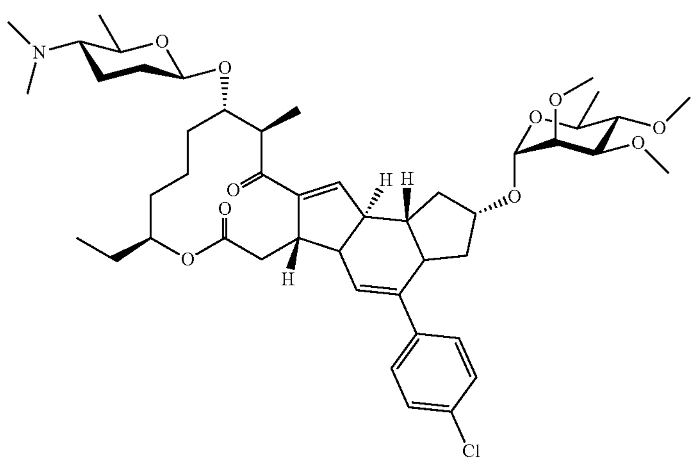 |
| 10 | 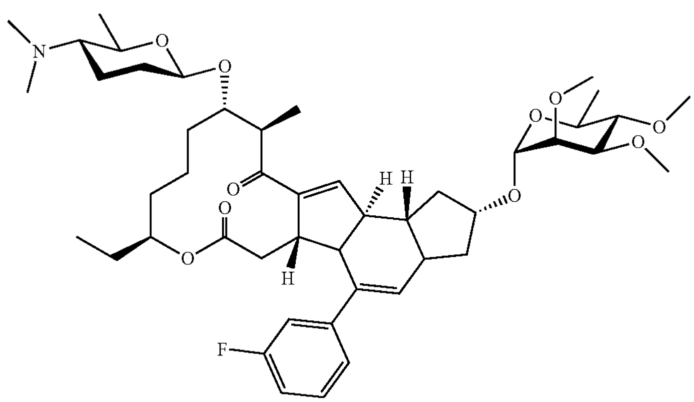 |

TABLE 1-continued

| No. | Structure |
| --- | --- |
| 11 | *(chemical structure with 4-chlorophenyl substituent)* |
| 12 | *(chemical structure with 4-trifluoromethoxyphenyl substituent, F₃CO)* |
| 13 | *(chemical structure with 4-trifluoromethylphenyl substituent, F₃C)* |

TABLE 1-continued

| No. | Structure |
|-----|-----------|
| 14  | 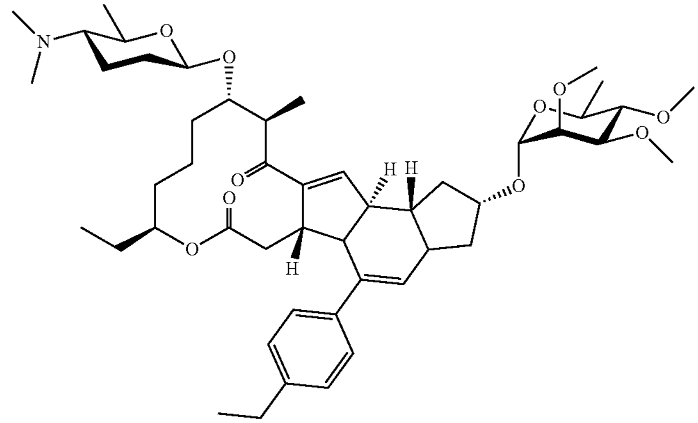          |
| 15  | 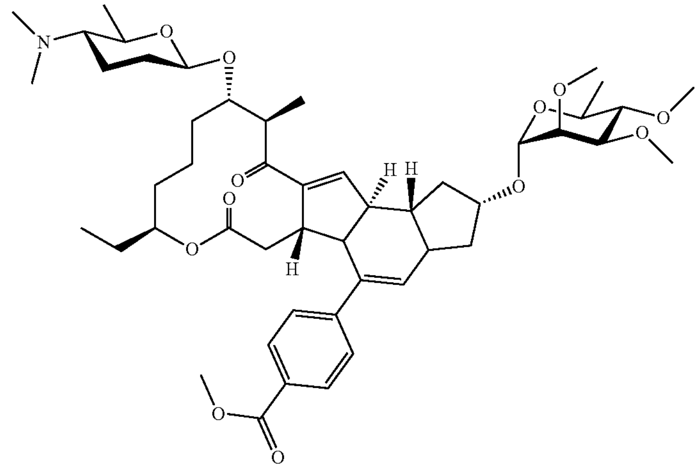          |
| 16  | 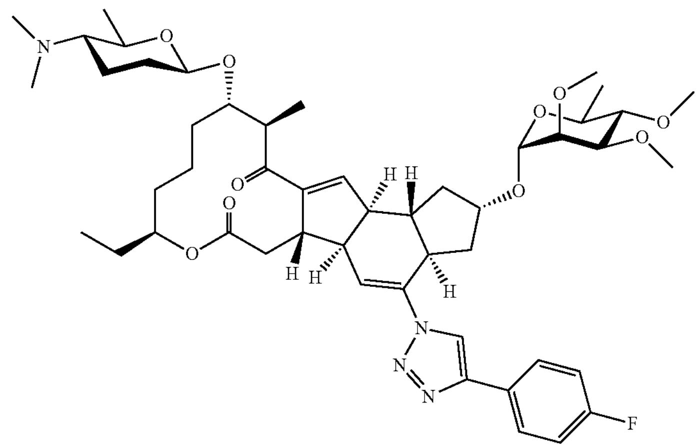          |

TABLE 1-continued

| No. | Structure |
|---|---|
| 17 | 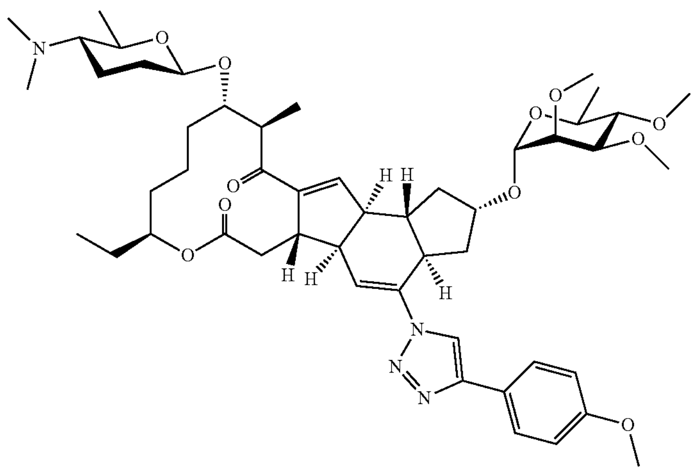 |
| 18 | 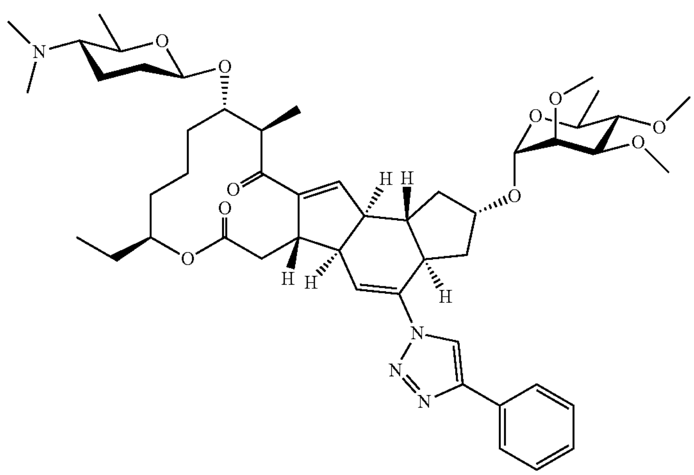 |
| 19 | 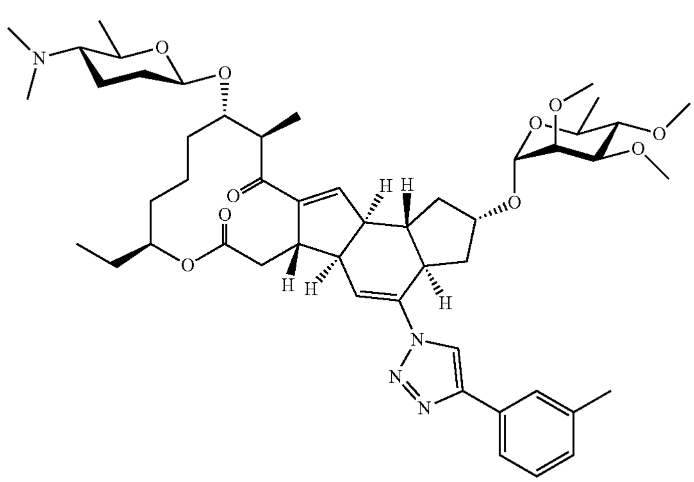 |

TABLE 1-continued

| No. | Structure |
|---|---|
| 20 | 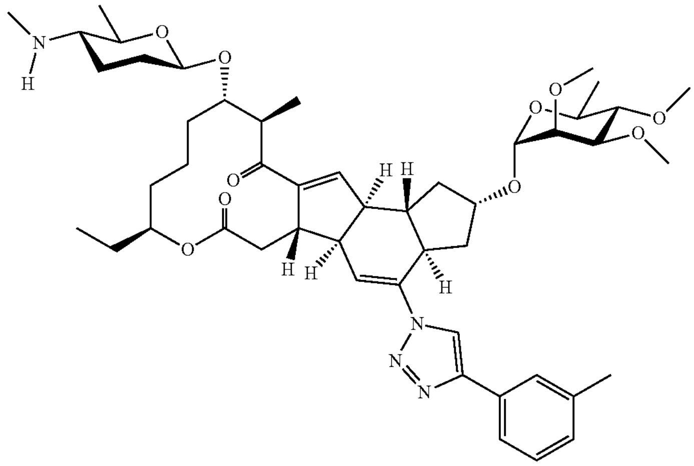 |
| 21 | 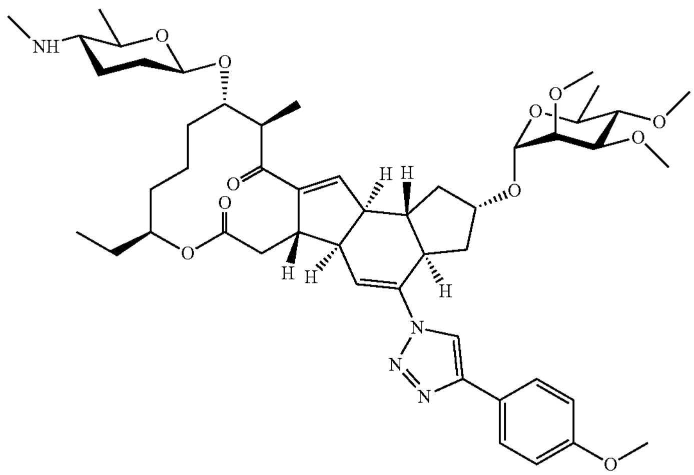 |
| 22 | 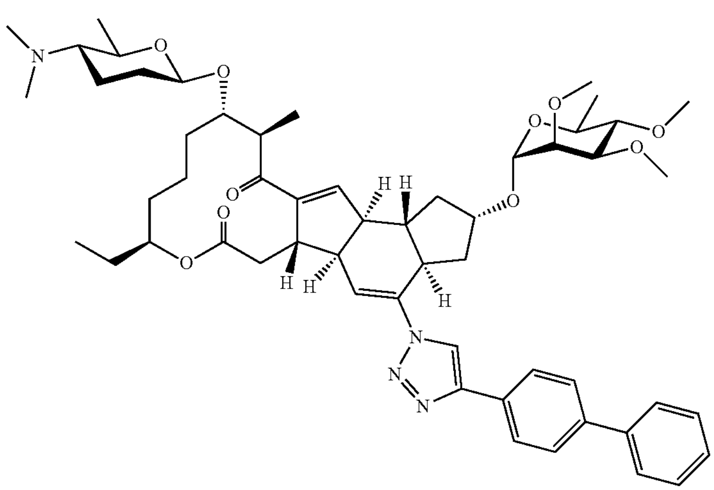 |

TABLE 1-continued

| No. | Structure |
|-----|-----------|
| 23  | 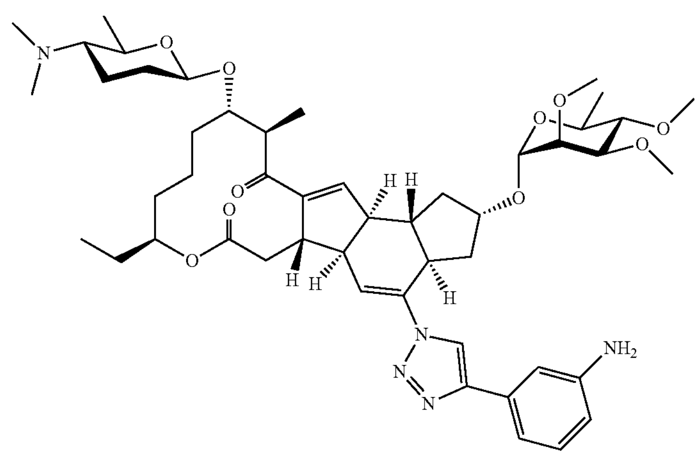          |
| 24  | 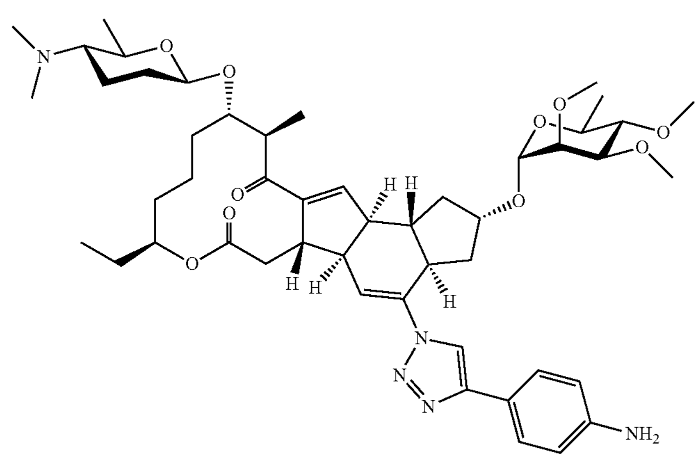          |
| 25  | 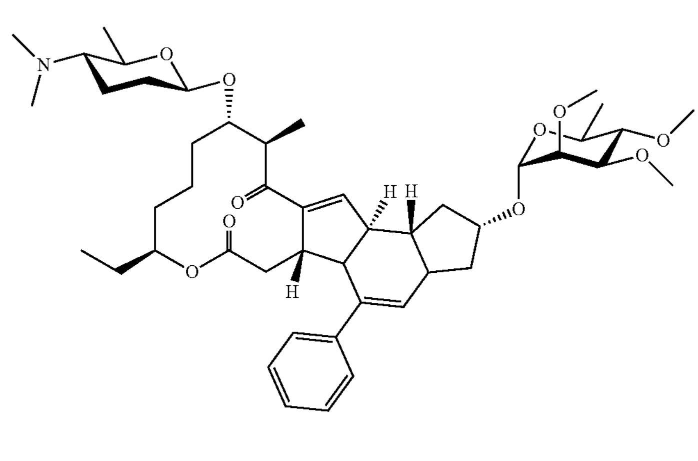          |

TABLE 1-continued
| No. | Structure |
|---|---|
| 26 | 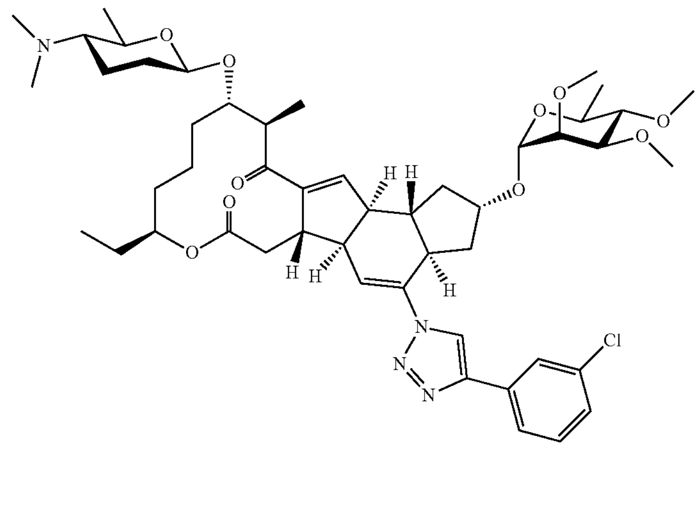 |
| 27 | 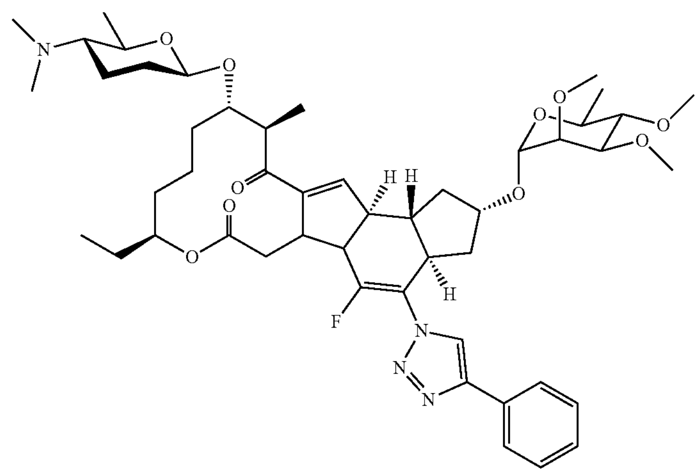 |
In certain embodiments, the compounds of the invention are those shown below.
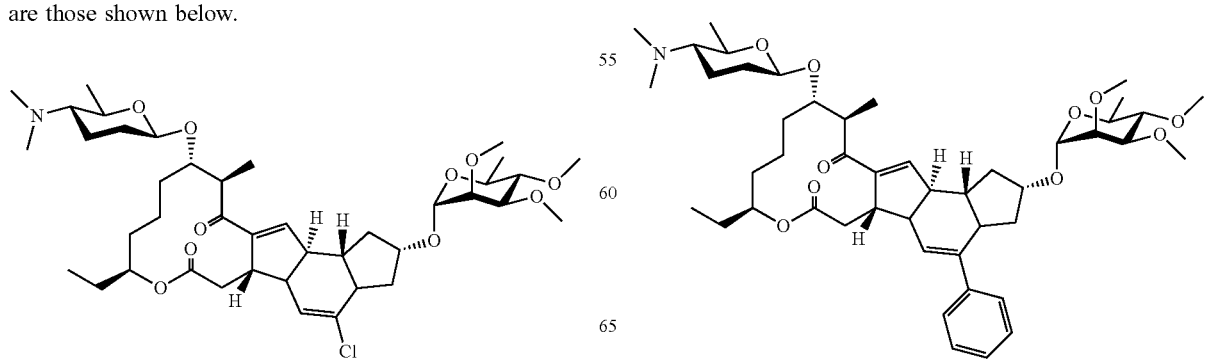

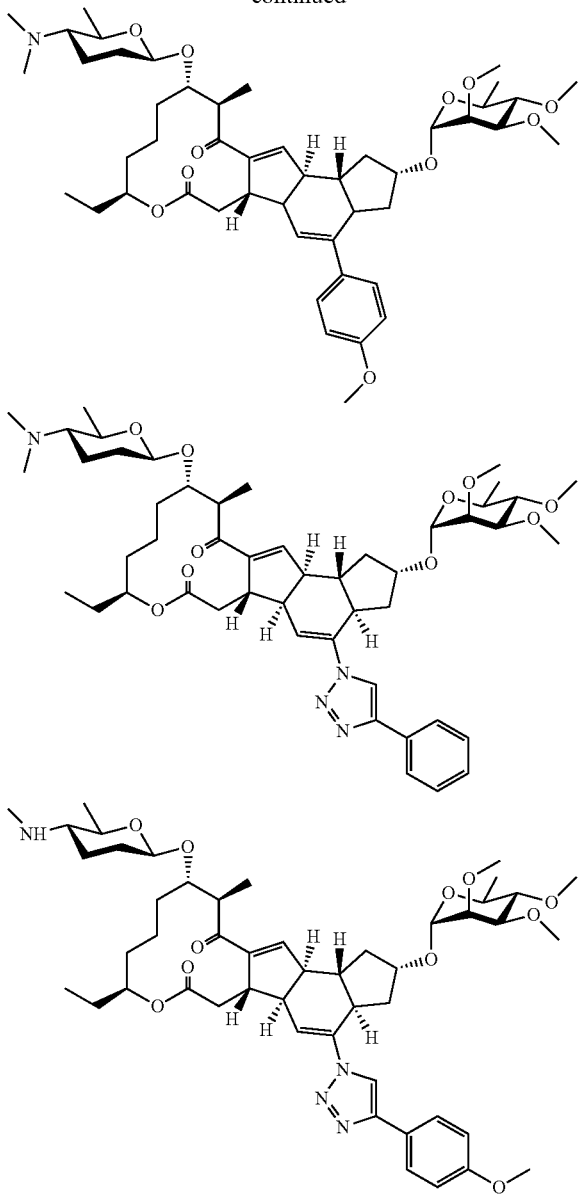

Where substituent groups are specified by their conventional chemical formulae, written from left to right, the structures optionally also encompass the chemically identical substituents, which would result from writing the structure from right to left, e.g., —CH$_2$O— is intended to also optionally recite —OCH$_2$—.

The term "alkyl," by itself or as part of another substituent, means, unless otherwise stated, a straight or branched chain, or cyclic hydrocarbon radical, or combination thereof, which may be fully saturated, mono- or polyunsaturated and can include di-, tri- and multivalent radicals, having the number of carbon atoms designated (i.e., C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to optionally include those derivatives of alkyl defined in more detail below, such as "heteroalkyl." Alkyl groups that are limited to hydrocarbon groups are termed "homoalkyl." Exemplary alkyl groups include the monounsaturated C$_{9-10}$, oleoyl chain or the diunsaturated C$_{9-10, 12-13}$ linoeyl chain.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The terms "aryloxy" and "heteroaryloxy" are used in their conventional sense, and refer to those aryl or heteroaryl groups attached to the remainder of the molecule via an oxygen atom.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, S, Si and B, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to optionally include both substituted and unsubstituted forms of the indicated radical.

The symbol "R" is a general abbreviation that represents a substituent group that is selected from H, substituted or unsubstituted alkyl, substituted or unsubstituted heteroalkyl, substituted or unsubstituted aryl, substituted or unsubstituted heteroaryl, and substituted or unsubstituted heterocycloalkyl groups.

II. Methods of Making the Compounds

The compounds described herein can be prepared in a variety of ways. The compounds can be synthesized using various synthetic methods. At least some of these methods are known in the art of synthetic organic chemistry. The compounds described herein can be prepared from readily available starting materials. Optimum reaction conditions can vary with the particular reactants or solvent used, but such conditions can be determined by one skilled in the art by routine optimization procedures.

Variations on Formula I include the addition, subtraction, or movement of the various constituents as described for each compound. Similarly, when one or more chiral centers are present in a molecule, all possible chiral variants are included. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts, Greene's Protective Groups in Organic Synthesis, 5th. Ed., Wiley & Sons, 2014, which is incorporated herein by reference in its entirety.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry (MS), or by chromatography such as high performance liquid chromatography (HPLC) or thin layer chromatography.

The compounds described herein can be prepared using spinosyn precursor, spinosyn, or spinosyn analogue starting materials, such as those set forth in U.S. Pat. No. 5,362,634. As used herein, spinosyn precursors, spinosyns, or spinosyn analogue starting materials used in the synthetic methods include any tetracyclic spinosyn molecule comprising a polyketide-derived tetracyclic macrolide appended with two saccharides.

The methods of making the compounds described herein can include from one to five chemical steps performed on spinosyns, often without need for purification of thus formed intermediates.

Alternatively, compounds described herein can be made by those skilled in the art using synthetic chemistry transformations known to convert C, C double bonds to cycloalkyl derivatives, either directly or in multiple chemical steps. See, for example, Nishiwaki (Editor) in *Methods and Application of Cycloaddition Reactions in Organic Synthesis* (1$^{st}$ Edition), ISBN-13: 978-1118299883, ISBN-10: 1118299884.

Additional modifications can be made to compounds according to Formula I while retaining the desired activity of the compounds. For example, the saccharide groups optionally present as A and B in the compounds according to Formula I (e.g., forosamine and rhamnose) can be modified by methods in the art and retain pesticidal activity. Forosamine can be replaced by certain nitrogen-containing sugars and non-sugar substituents with retention of some degree of activity. See, Gaisser et al. (2002) *Chem. Comm.* 6:618-619; and Gaisser et al. (2009) *Org. Biomol. Chem.* 7:1705-1708, herein incorporated by reference. Likewise, rhamnose replacement analogs may be produced. See, Creemer et al. (2000) *J. Antibiotics*, 53:171-178; Sparks et al. (2001) *Pest Manag. Sci.*, 57:896-905, herein incorporated by reference. Activity of the spinosyn derivative can be retained after changes in the structure of the rhamnose, especially certain modifications at C-2' and C-3' of the tri-O-methylrhamnose moiety.

Other methods of sugar modification can be made and are well known in the art. See, Kirst et al. (2002) *Curr. Top. Med. Chem.* 2:675-699. In some embodiments, one or more of the saccharide moieties is replaced with another natural or a synthetic sugar. Synthetic sugars include modified sugars. As used herein, a "modified sugar" is covalently functionalized with a "modifying group." Useful modifying groups include, but are not limited to, water-soluble polymers, therapeutic moieties, diagnostic moieties, biomolecules and the like. Addition or removal of any saccharide moieties present on the precursor or substrate is accomplished either chemically or enzymatically.

In some embodiments, chemical deglycosylation can be used by exposure of the spinosyn compounds described herein to the compound trifluoromethanesulfonic acid, or an equivalent compound. This treatment results in the cleavage of most or all sugars except the linking sugar (N-acetylglucosamine or N-acetylgalactosamine), while leaving the remainder of the molecule intact. See, Hakimuddin et al. (1987) *Arch. Biochem. Biophys.* 259:52 and Edge et al. (1981) *Anal. Biochem.* 118:131. Enzymatic cleavage of carbohydrate moieties on peptide variants can be achieved by the use of a variety of endo- and exo-glycosidases as described by Thotakura et al. (1987) *Meth. Enzymol.* 138:350. Chemical addition of glycosyl moieties is carried out by any art-recognized method. See, for example, U.S. Pat. Nos. 5,876,980; 6,030,815; 5,728,554; 5,922,577; and WO 2004/99231.

Synthesis of the compounds of the invention is described below in the Examples. Generally, the methods comprise 1 to 5 chemical steps (semi-synthesis) performed on spinosyns or spinosyn precursors often without the need for purification of the intermediates. As indicated herein, the terms "spinosyn precursors" or "spinosyns" used in the method include any tetracyclic spinosyn molecule comprising a polyketide-derived tetracyclic macrolide appended with two saccharides.

III. Formulations

The compounds described herein or salts thereof can be provided in a formulation or composition. The spinosyn derivatives of the invention may be prepared in compositions for control of pests. The formulations can include other active ingredients and/or plant or plant product treatment compounds. Optionally, the formulation can include a contact-acting insecticide and/or miticide. Exemplary contact-acting insecticides and/or miticides include those derived from fatty acids, fatty acid esters, fatty acid sugar esters, and fatty acid salts, pyrethrum extract, plant oils and their salts, vegetable oils and their salts, essential oils, mineral oils, pyrethrum extract, and combinations thereof. The contact-acting insecticide and/or miticide can also include avermectins. One skilled in the art will appreciate that the resulting spinosyn-containing compositions and formulations disclosed herein are not only pesticidally effective, but also environmentally sound and safe for human use. Further, some of the compositions and formulations can be residual in that they do not leach out of baits or easily wash off of the leaves during rain, and thus can protect against insect and mite pests during and after rainy weather. Optionally, the compositions and formulations can exhibit synergy, and result in better than expected results than just the spinosyn or the insecticide or miticide treatment alone.

Optionally, the present compounds are usefully combined with ectoparasiticides (agents that control arthropod pests that typically attack their hosts on the external ("ecto") surface). The spinosyn compounds are formulated for use as ectoparasiticides in manners known to those skilled in the art. Representative ectoparasiticides include the following: Abamectin, Alphamethrin, Amitraz, Avermectin, Coumaphos, Cycloprothrin, Cyfluthrin, Cyhalothrin, Cypermethrin, Cyromazine, Deltamethrin, Diazinon, Diflubenzuron, Dioxathion, Doramectin, Famphur, Fenthion, Fenvalerate, Flucythrinate, Flumethrin, Hexaflumuron, Ivermectin, Lindane, Lufenuron, Malathion, Methoprene, Metriphonate, Moxidectin, Permethrin, Phosme, Pirimiphos, Propetamphos, Propoxur, Rotenone, Temephos, Tetrachlorvinphos, Trichlorfon, Zetacypermethrin, B.t. Biotoxins and Boric Acid.

Optionally, the present compounds are usefully combined with other ectoparasiticides or with anthelmentics, the latter also known as endoparasiticides ("endo"=internal, controlling internal parasites which are typically platyhelminthes and nemathelminthes). Representative such endoparasiticides include the following: Abamectin, Albendazole, Avermectin, Bunamidine, Coumaphos, Dichlorvos, Doramectin, Epsiprantel, Febantel, Fenbendazole, Flubendazole, Ivermectin, Levamisole, Mebendazole, Milbemycin, Morantel, Moxidectin, Netobimin, Niclosamide, Nitroscanate, Oxfendazole, Oxibendazole, Piperazine, Praziquantel, Pyrantel, Ricombendazole, Tetramisole, Thiabendazole, Clorsulon, Closantel, Diamphenethide, Nitroxynil, Oxyclozanide, Rafoxanide, Triclabendazole.

The formulations described herein can further include, in combination with the spinosyn component, one or more other compounds that have activity against the specific ectoparasite or endoparasite to be controlled, such as, for example, synthetic pyrethroids, natural pyrethins, organophosphates, organochlorines, carbamates, formamidines, avermectins, milbemycins, insect growth regulators (including chitin synthesis inhibitors, juvenile hormone analogs, and juvenile hormones), nitromethylenes, pyridines and pyrazoles. In an exemplary embodiment, the composition can include an additional contact-acting insecticide and/or miticide. The compositions can be utilized as liquid concentrates, Ready-To-Use (RTU) liquid sprays, dusts, or solids, depending upon the needs of the user. In use, the composition can be applied to the pests themselves, in the vicinity of the pests, and/or in the vicinity of plants and plant products that are to be protected.

In general, a formulation will include a compound as described herein and one or more physiologically acceptable adjuvants. Formulations include concentrated versions, in which the present active agent is present in a concentration of from 0.001 to 98.0 percent, with the remaining content being physiologically acceptable carriers. Such formulations, especially those with less than 50 percent of the present compound, can sometimes be used directly, but these formulations can also be diluted with other physiologically acceptable carriers to form more dilute treating formulations. These latter formulations can include the active agent in lesser concentrations of from 0.001 to 0.1 percent.

Compositions are prepared according to the procedures and formulas which are conventional in the agricultural or pest control art. The compositions may be concentrated and dispersed in water or may be used in the form of a dust, bait or granular formulation. The dispersions are typically aqueous suspensions or emulsions prepared from concentrated formulations of the compounds. The water-soluble or water-suspension or emulsifiable formulations are either solids, wettable powders, or liquids, known as emulsifiable concentrates or aqueous suspensions. Wettable powders may be agglomerated or compacted to form water dispersible granules. These granules comprise mixtures of compound, inert carriers and surfactants. The concentration of the compound is typically between about 0.1% to about 90% by weight. The inert carrier is typically attapulgite clays, montmorillonite clays and the diatomaceous earths or purified silicates.

Surfactants comprise typically about 0.5% to about 10% of the wettable powder. Surfactants include sulfonated lignins, condensed napthalene-sulfonates, the napthalene-sulfonates, alkyl-benenesulfonates, alkysulfonates or non-ionic surfactants such as ethylene oxide adducts of alkylphenols or mixtures thereof. Emulsifiable concentrates of the derivatives of the invention typically range from about 50 to about 500 grams of spinosyn derivative per liter of liquid, equivalent to about 10% to about 50%, dissolved in an inert carrier which is a mixture of a water immiscible solvent and emulsifiers. Organic solvents include organics such as xylenes, and petroleum fractions such as high-boiling naphthlenic and olefinic portions of petroleum which include heavy and aromatic naphtha. Other organics may also be used such as terpenic solvents-rosin derivatives, aliphatic ketones such as cyclohexanone and complex alcohols. Emulsifiers for emulsifiable concentrates are typically mixed ionic and/or nonionic surfactants such as those mentioned herein or their equivalents.

Aqueous suspensions may be prepared containing water-insoluble spinosyn derivatives, where the compounds are dispersed in an aqueous vehicle at a concentration typically in the range of between about 5% to about 50% by weight. The suspensions are prepared by finely grinding the compound and vigorously mixing it into a vehicle of water, surfactants, and dispersants. Inert ingredients such as inorganic salts and synthetic or natural gums may also be employed to increase the density and/or viscosity of the aqueous vehicle as is desired.

Precipitated flowables may be prepared by dissolving at least one spinosyn derivative of the invention in a water-miscible solvent and surfactants or surface active polymers. When these formulations are mixed with water, the active spinosyn derivative precipitates with the surfactant controlling the size of the resulting micro-crystalline precipitate. The size of the crystal can be controlled through the selection of specific polymer and surfactant mixtures.

The spinosyn derivatives may also be applied as a granular composition that is applied to the soil. The granular composition typically contains from about 0.5% to about 10% by weight of the derivative. The spinosyn derivative is dispersed in an inert carrier which is typically clay or an equivalent substance. Generally, granular compositions are prepared by dissolving the compounds of the invention in a suitable solvent and applying it to a granular carrier which has been pre-formed to the desirable particle size. The particle size is typically between about 0.5 mm to 3 mm. The granular compositions may also be prepared by forming a dough or paste of the carrier and compound, drying the combined mixture, and crushing the dough or paste to the desired particle size.

The spinosyn derivative may also be combined with an appropriate organic solvent. The organic solvent is typically a bland petroleum oil that is widely used in the agricultural industry. These combinations are typically used as a spray. More typically, the spinosyn compounds are applied as a dispersion in a liquid carrier, where the liquid carrier is water. The compounds may also be applied in the form of an aerosol composition. The compound is dissolved in an inert carrier, which is a pressure-generating propellant mixture. The aerosol composition is packaged in a container, where the mixture is dispersed through an atomizing valve. Propellant mixtures contain either low-boiling halocarbons, which may be mixed with organic solvents or aqueous suspensions pressurized with inert gases or gaseous hydrocarbons.

The compounds may be applied to any locus inhabited by an insect or mite. Such locus typically is cotton, soybean and vegetable crops, fruit and nut trees, grape vines, houses and ornamental plants. The amount of the spinosyn derivative applied to the loci of insects and mites can be determined by those skilled in the art. Generally, the concentrations of from about 10 ppm to about 5,000 ppm provide the desired control. For crops such as soybeans and cotton, the rate of application is about 0.01 to about 1 kg/ha, where the spinosyn derivative is applied in a 5 to 50 gal/A spray formulation.

The composition can be formulated in a liquid concentrate, ready-to-use (RTU) liquid spray, dust, or solid form. The formulation chosen will depend on the use of the product.

The following general treatment methods are preferably suitable for carrying out the seed treatment, or plant propagation material treatment, according to the invention: dry treatments (preferably with addition of adhesion promoters such as, for example, liquid paraffin or talc), and, if appropriate, colorants, slurry treatments (preferably with addition of wetters, dispersants, emulsifiers, adhesives, inert fillers and colorants), aqueous liquid treatments (preferably with addition of emulsifiers, dispersants, thickeners, antifreeze agents, polymers, adhesives and colorants), solvent-based liquid treatments (with addition of solvents and colorants), emulsion treatments (with addition of emulsifiers, solvents and colorants).

The total active spinosyn derivative in the treatment formulations preferably amounts to 0.01% to 80% by weight. For example, the total active spinosyn compound can amount to 0.01% by weight, 0.05% by weight, 0.1% by weight, 0.5% by weight, 1% by weight, 5% by weight, 10% by weight, 20% by weight, 30% by weight, 40% by weight, 50% by weight, 60% by weight, 70% by weight, or 80% by weight. Generally, about 1 to about 300 g of spinosyn derivative are applied to every 100 kg of seed or plant propagation material in the form of a treatment.

Those of skill in the art will understand that the specific dose level and frequency of dosage for any particular subject may be varied and will depend upon a variety of factors, including the activity of the specific compound employed, the metabolic stability and length of action of that compound, the species, age, body weight, general health, sex, and diet of the subject, the mode and time of administration, rate of excretion, drug combination, and severity of the particular condition. The precise dose to be employed in the formulation will also depend on the route of administration, and the seriousness of the infection, and should be decided according to the judgment of the practitioner and each subject's circumstances.

IV. Methods of use

The spinosyn compounds described herein have insecticidal and pesticidal activity against pests, including insects, arachnids and nematodes. Therefore, the compounds and formulations as described herein can be used for controlling, inhibiting, and/or inactivating a pest of interest. The spinosyn compounds and formulations described herein provide a key source of agrichemicals with activities against crop pest species. In some instances, the compounds and formulations can be used in animal health. The spinosyn compounds and formulations described herein can be provided in agricultural and/or pharmaceutical compositions in effective amounts to control or inhibit the pest or condition being treated. The spinosyn compounds and formulations described herein may possess one or more the following characteristics as compared to natural spinosyns: increased potency; reduced risk to non-target species; lower potential for environmental damage; minimal cross-resistance to other pesticides; and may overcome existing pest resistance to currently available spinosyn products.

The compounds and formulations described herein are useful in controlling or containing pests populations. The compounds and formulations exhibit potent and broad-spectrum activity against numerous commercially important insect pests. The spectrum of target insects include many species of Lepidoptera and Diptera along with some members of several other insect orders, including planthoppers, leafhoppers, spider mites and cockroaches. The compounds and formulations have potent and broad activity against many problematic larval species of Lepidoptera. Insecticidal activity is generally observed after administration of the spinosyns by a variety of delivery methods, including contact and oral feeding assays.

One skilled the art will appreciate that the compounds, formulations, and methods disclosed herein can be used to treat a variety of home and garden insect and mite pests such as, by way of non-limiting example, members of the insect order Lepidoptera including Southern armyworm, codling moth, cutworms, clothes moths, Indian meal moth, leaf rollers, corn earworm, cotton bollworm (also called Tomato fruit worm), European corn borer, imported cabbageworm, cabbage looper, pink bollworm, American bolloworm, tomato hornworm, bagworms, Eastern tent caterpillar, sod webworm, diamondback moth, tomato pinworm, grape berry moth, cotton leafworm, beet armyworm, and fall armyworm; members of the order Homoptera including cotton aphid leafhoppers, plant hoppers, pear psylla, scale insects, whiteflies, and spittle bugs; and members of the insect order Diptera including house flies, stable flies, blow flies and mosquitoes; mites; and ants. The compounds and formulations described herein can also be used to treat members of the order Thysanoptera including melon thrips and Western flower thrips; members of the order Coleoptera, including Colorado potato beetles; members of the order Orthoptera; and Leaf miners of the orders Lepidoptera (moths and butterflies), Hymenoptera (leaf mining sawflies), Coleoptera (beetles), and Diptera (true flies). The compounds and formulations can be used to control and/or treat ants, green peach aphids, adult house flies, western tent caterpillar larvae, and two-spotted spider mites. Generally, the spinosyn compounds and formulations described herein can be active against a number of ectoparasites in a number of animals by a variety of routes. The present compounds and formulations can be used to control a wide variety of arthropod pests.

Representative pests which can be controlled by the present compounds and formulations additionally include: Arachnids, *Amblyomma americanum* (Lone-star tick), *Amblyomma maculatum* (Gulf Coast tick), *Argas persicus* (fowl tick), *Boophilus microplus* (cattle tick), *Chorioptes* spp. (mange mite), *Demodex bovis* (cattle follicle mite), *Demodex canis* (dog follicle mite), *Dermacentor andersoni* (Rocky Mountain spotted fever tick), *Dermacentor variabilis* (American dog tick), *Dermanyssus gallinae* (chicken mite), *Ixodes ricinus* (common sheep tick), *Knemidokoptes gallinae* (deplumming mite), *Knemidokoptes mutans* (scaly-leg mite), *Otobius megnini* (ear tick), *Psoroptes equi* (scab mite), *Psoroptes ovis* (scab mite), *Rhipicephalus sanguineus*

(brown dog tick), *Sarcoptes scabiei* (mange mite), Insects—*Aedes* (mosquitoes), *Anopheles* (mosquitoes), *Culex* (mosquitoes), *Culiseta*, *Bovicola bovis* (cattle biting louse), *Callitroga homnivorax* (blowfly), *Chrysops* spp. (deer fly), *Cimex lectularius* (bed bug), *Cochliomyia* spp. (screwworm), *Ctenocephalides canis* (dog flea), *Ctenocephalides felis* (cat flea), *Culicoides* spp. (midges, sandflies, punkies, or no-see-ums), *Damalinia ovis* (sheep biting louse), *Dermatobia* spp. (warble fly), *Gasterophilus haemorrhoidalis* (nose bot fly), *Gasterophilus intestinalis* (common horse bot fly), *Gasterophilus nasalis* (chin fly), *Glossina* spp. (tsetse fly), *Haematobia irritans* (horn fly, buffalo fly), *Haematopinus asini* (horse sucking louse), *Haematopinus eurysternus* (short nosed cattle louse), *Haematopinus ovillus* (body louse), *Haematopinus suis* (hog louse), *Hydrotaea irritans* (head fly), *Hypoderma bovis* (bomb fly), *Hypoderma lineatum* (heel fly), *Linognathus ovillus* (body louse), *Linognathus pedalis* (foot louse), *Linognathus vituli* (long nosed cattle louse), *Lucilia* spp. (maggot fly), *Melophagus ovinus* (sheep ked), *Musca* spp. (house fly, face fly), *Oestrus ovis* (nose bot fly), *Pediculus* spp. (lice), *Phlebotomus* spp. (sandfly), *Phormia regina* (blowfly), *Psorophora* spp. (mosquito), *Pthirus* spp. (lice), *Reduvius* spp. (assassin bug), *Simulium* spp. (black fly), *Solenopotes capillatus* (little blue cattle louse), *Stomoxys calcitrans* (stable fly), *Tabanus* spp. (horse fly), *Tenebrio* spp. (mealworms), *Triatoma* spp. (kissing bugs). Likewise, the spinosyn derivatives are useful against pests including: from the order of the Isopoda, for example, *Oniscus asellus, Armadillidium vulgare, Porcellio scaber*; from the order of the Diplopoda, for example, *Blaniulus guttulatus*; from the order of the Chilopoda, for example, *Geophilus carpophagus, Scutigera* spp; from the order of the Symphyla, for example, *Scutigerella immaculata*; from the order of the Thysanura, for example, *Lepisma saccharina*; from the order of the Collembola, for example, *Onychiurus armatus*; from the order of the Orthoptera, for example, *Blatta orientalis, Periplaneta americana, Leucophaea maderae, Blattella germanica, Acheta domesticus, Gryllotalpa* spp., *Locusta migratoria migratorioides, Melanoplus differentialis, Schistocerca gregaria*; from the order of the Dermaptera, for example, *Forficula auricularia*; from the order of the Isoptera, for example, *Reticulitermes* spp.; from the order of the Anoplura, for example, *Phylloxera vastatrix, Pemphigus* spp., *Pediculus humanus corporis, Haematopinus* spp., *Linognathus* spp; from the order of the Mallophaga, for example, *Trichodectes* spp., *Damalinea* spp.; from the order of the Thysanoptera, for example, *Frankliniella occidentalis, Hercinothrips femoralis, Thrips palmi, Thrips tabaci*; from the order of the Heteroptera, for example, *Eurygaster* spp., *Dysdercus intermedius, Piesma quadrata, Cimex lectularius, Rhodnius prolixus, Triatoma* spp.; from the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp., *Psylla* spp.; from the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Spodoptera exigua, Mamestra brassicae, Panolis flammea, Prodenia litura, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp.; from the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Antho nomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica, Oulema oryzae, Lissorhoptrus oryzophilus*; from the order of the Hymenoptera, for example, *Diprion* spp., *Hoplocampa* spp., *Lasius* spp., *Monomorium pharaonis, Vespa* spp.; from the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Liriomyza* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa*; from the order of the Siphonaptera, for example, *Xenopsylla cheopis, Ceratophyllus* spp.; from the order of the Arachnida, for example, *Scorpio maurus, Latrodectus mactans*; from the order of the Acarina, for example, *Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp.

Insects that can be controlled with the aid of the compounds and formulations described herein include those of the following orders: soil-dwelling insects: Diptera (for example the frit-fly, wheat-bulb fly), Coleoptera (for example *Diabrotica* (wire worm), Lepidoptera (for example dart moth), Blattophtheroidea, Myriopoda. Leaf insects: Aphidina, Coleoptera, Brachycera, Lepidotera, Homoptera, Tysanoptera, Aleurodina, Cicadina, Acasi, Cossina, Heteroptera.

Methods for controlling insect and mite pests as described herein can include providing a formulation that has an effective amount of at least one spinosyn compound as described herein, at least one of an additional insecticide and miticide, and at least one of a solvent or an acceptable carrier, and administering an effective amount of the formulation to control pests. Where the formulation is a liquid, the method can further include administering an effective amount of the formulation such that an effective amount of the formulation contacts pests, plants and plant products, the vicinity of the pests, and/or the vicinity of the plants and plant products. Where the formulation is a dust or a solid, administering an effective amount of the formulation can include placing an effective amount of the composition in a vicinity of pests and/or placing an effective amount of the composition in a vicinity of plants and plant products to be protected.

An effective amount of the spinosyn compound or formulation as described herein is an amount to control or kill the target pest. The use rates vary widely and are highly impacted by the target pest, target pest size and number, host crop and crop age, climate and economic threshold or acceptable damage. In general, a typical use rate is set at about 1 ppm (1 mg a.i./kg of grain). For use on crops, between about 25 and about 200 grams per hectare (0.023 and 0.184 lbs per acre) of active ingredient is used. Turf rates are 88-450 g a.i./ha (0.078-0.4 lb ai/acre). Ornamental rates are 0.046-0.17 lb ai/100 gallons or 55-204 ppm. There is typically a positive temperature correlation that results in better activity with higher temperatures. Performance against some pests, such as leafminers and thrips, are positively impacted by the addition of nominal rates of penetrating surfactants such as crop oils.

All animals are subject to attack by such pests, though the problems are most severe among vertebrate hosts. Accordingly, the spinosyn compounds and formulations described herein can be used on humans, livestock animals, (cattle, sheep, pigs, goats, buffalo, water buffalo, deer, rabbits, chickens, turkeys, ducks, geese, ostriches, and the like), horses and other pleasure animals, mink and other animals grown for their fur, rats, mice, other animals used in laboratory and research settings, companion animals such as dogs and cats, fish, crustacea, and other aquatic animals. In short, the spinosyn compounds and formulations described herein are useful for treatment of the whole range of animals.

Arthropod pests are inhibited or killed on a host animal by contacting the pest with an effective amount of a spinosyn compound as described herein.

Techniques for delivering the compounds and formulations described herein are well known to those skilled in the art. In general, a present formulation comprising at least one spinosyn compound is applied to the exterior surface of an animal, whereby it contacts pests already present on the host as well as those which arrive on the host's body within the efficacy period. Typically, the spinosyn compound is formulated in a liquid formulation which is sprayed onto the animal's surface or poured onto the animal's surface. Another conventional treatment is a "dip", whereby cattle are treated by being substantially immersed in a dilute solution containing the spinosyn compound. For some hosts and pests, the formulation can be a dust, which is sprinkled onto the host, or a shampoo or cream which is employed in bathing the animal. Collars on cats and dogs can also be employed as a way of delivering the derivatives directly to the animal's surface.

The compounds and formulations described herein can also be applied to locations frequented by animals, so that pests are thereby contacted by the compound even as in direct application to the host. Application to pet bedding can be used, as well as application to carpeting. For cattle, dusting bags can be used. These are positioned in a doorway where the cattle inevitably rub against the bag and pests are contacted by the present compound.

Optionally, the present compounds and formulations can be used to control insects and arachnids which are pests in the feces of cattle and other animals. The compounds and formulations can be administered orally and the compounds travel through the intestinal tract and emerge in the feces. Control of pests in the feces indirectly protects the animals from the pests.

The compounds and formulations described herein may be applied to the foliage of a plant which a pest might feed on. Additionally, the compounds may be used orally or topically to control pests on animals.

Oral administration may be carried out using tablets and animal feeds. For some animals, such as certain cats, administration is best accomplished by using an acceptable liquid formulation that is administered directly or added to their food ration. Especially useful methods of orally administering the spinosyn derivatives are by administering it in chewable tablets or treats and animal feeds.

The spinosyn compounds and formulations described herein are also useful for the treatment of animals to control arthropods, i.e., insects and arachnids, which are pests on animals. These arthropod pests typically attack their hosts on the external ("ecto") surface; agents which control such pests are referred to as "ectoparasiticides".

The spinosyn compounds and formulations can be used for treating the soil, for treating seed or plant propagation material, and for drenching and irrigating plants. The following exemplary types of seed and plant propagation material can be treated: maize, cereals (such as, for example, wheat, barley, oats, rye), rice, seed potatoes, cotton, oilseed rape, sunflower, beet (such as, for example, sugar beet), vegetable seed (such as, for example, onion, cabbage, tomato), (fodder) legumes, peanuts, soya, sorghum, and the like.

It is advantageous to apply granules comprising the active compound described herein into or onto the soil. Examples of suitable applications include broadcast, band, furrow and planting-hole application.

It is particularly advantageous to emulsify or dissolve the spinosyns or their salts in water and to use this for irrigating the plants. Examples of suitable applications are spraying onto the soil, drenching, i.e. irrigating the plants with active-compound-containing solutions, and drip irrigation, and also use in hydroponic systems, in particular in the production of vegetables and ornamentals.

Seed treatments are suitable for controlling animal pests, preferably arthropods and nematodes, in particular insects and arachnids, which are found in agriculture and in forests. They are effective against normally-sensitive and resistant species and against all or individual developmental stages.

In some embodiments, the spinosyn compounds and formulations described herein can be used for promoting or accelerating wound healing in a mammal comprising administering at least one spinosyn compound or a physiologically acceptable derivative or salt thereof, to a mammal in need thereof. In this manner, the spinosyn compounds and formulations can be used for the manufacture of a medicament for promoting or accelerating wound healing in animals, including humans (see, for example, U.S. Pat. No. 8,536, 142) or in the treatment of head lice in humans.

As used herein the terms treatment, treat, or treating refer to a method of reducing one or more symptoms of a disease, infection, or condition. Such methods include controlling, inhibiting, and/or inactivating a pest. Thus in the disclosed method, treatment can refer to a 10%, 20%, 30%, 40%, 50%, 60%, 70%, 80%, 90%, or 100% reduction in pests found in crops or animals and/or the severity of one or more symptoms of the disease, infection, or condition associated with such pests. For example, a method for controlling a pest is considered to be a treatment if there is a 10% reduction in one or more pests in a crop or in a subject as compared to a control. Similarly, a method for treating an infection is considered to be a treatment if there is a 10% reduction in one or more symptoms or signs of an infection in a subject as compared to a control. As used herein, control refers to the untreated condition. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a complete elimination of pests, or a cure or complete ablation of the disease, infection, condition, or symptoms of the disease, infection, or condition.

As used herein, subject means both mammals and non-mammals. Mammals include, for example, humans; non-human primates, e.g., apes and monkeys; cattle; horses; sheep; rats; mice; pigs; and goats. Non-mammals include, for example, fish and birds.

Non-limiting embodiments include:

1. A spinosyn compound of the following formula:

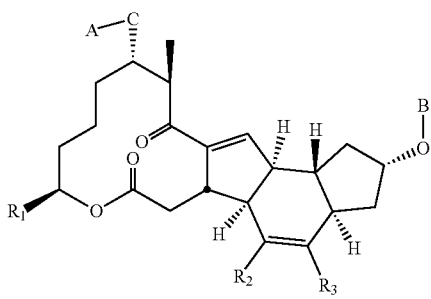

or a salt thereof, wherein A is selected from the group consisting of substituted or unsubstituted carbonyl, substituted or unsubstituted cycloalkyl, substituted or unsubstituted heterocycloalkyl, substituted or unsubstituted aryl, and substituted or unsubstituted heteroaryl; B is selected from the group consisting of substituted or unsubstituted cycloalkyl, substituted or unsubstituted heterocycloalkyl, substituted or unsubstituted aryl, and substituted or unsubstituted heteroaryl; C is O or NH; $R^1$ is selected from the group consisting of substituted or unsubstituted alkyl, substituted or unsubstituted aryl; and $R^2$ and $R^3$ are each independently selected from the group consisting of hydrogen, halogen, substituted or unsubstituted amino, substituted or unsubstituted alkoxy, substituted or unsubstituted aryloxy, substituted or unsubstituted alkyl, substituted or unsubstituted cycloalkyl, substituted or unsubstituted heterocycloalkyl, substituted or unsubstituted aryl, and substituted or unsubstituted heteroaryl, wherein $R^2$ and $R^3$ cannot both be hydrogen.

2. The embodiment of paragraph 1, wherein A comprises forosamine or a forosamine derivative, such as [(2R, 5S,6R)-6-methyl-5-(methylamino)oxan-2-yl]oxy-.

3. The embodiment of paragraph 1, wherein B comprises rhamnose or a rhamnose derivative, such as 3,4,5-trimethoxyrhamnose or 4-ethoxy-3,5-dimethoxyrhamnose.

4. The embodiment of any of paragraphs 1-3, wherein A comprises forosamine; B comprises rhamnose or a rhamnose derivative, such as 3,4,5-trimethoxyrhamnose or 4-ethoxy-3,5-dimethoxyrhamnose; C comprises oxygen; $R^1$ comprises ethyl; $R^2$ and $R^3$ are each independently selected the group consisting of hydrogen, halogen, substituted or unsubstituted phenyl, or substituted or unsubstituted phenyl triazole, wherein the substituted phenyl may have one or more substitutions including but not limited to halogen (e.g., chlorine, fluorine), alkyl (e.g., methyl, ethyl), halo alkyl (e.g., trifluoromethyl), alkoxy (e.g., methoxy, ethoxy), haloalkoxy (e.g. trifluoromethoxy), or ester (e.g., methyl ester), wherein the substituted phenyl triazole may have one or more substitutions including but not limited to halogen (e.g., chlorine, fluorine), alkyl (e.g., methyl), alkoxy (e.g., methoxy), phenyl, and amino, and wherein $R^2$ and $R^3$ are not both hydrogen.

5. The embodiment of any of paragraphs 1-4, wherein $R^2$ is hydrogen and $R^3$ is an unsubstituted or substituted phenyl.

6. The embodiment of paragraphs 1-4 and 5, wherein the substituted phenyl group is selected from the group consisting of methoxyphenyl, ethylphenyl, phenyl, chlorophenyl, fluorophenyl, trifluoromethoxyphenyl or methyl benzoate moiety.

7. The embodiment of any of paragraphs 1-6, wherein Formula I can be represented by Structure I-A:

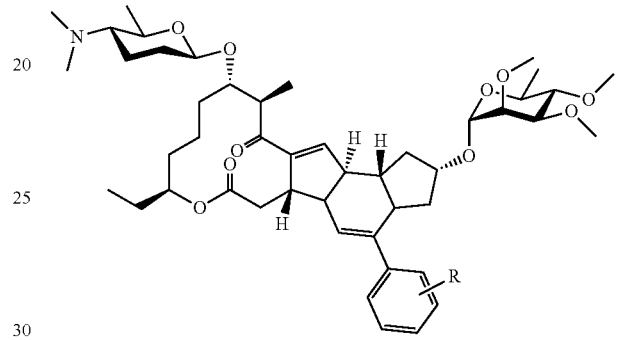

wherein R is selected from hydrogen, methoxy, ethoxy, chloro, fluoro, trifluoromethoxy, or methyl acetate.

8. The embodiment of any of paragraphs 1-4, wherein $R^2$ is an unsubstituted or substituted phenyl and $R^3$ is hydrogen.

9. The embodiment of any of paragraphs 1-4 and 8, wherein the substituted phenyl group is selected from the group consisting of methoxyphenyl, ethylphenyl, phenyl, chlorophenyl, fluorophenyl, trifluoromethoxyphenyl or methyl benzoate moiety.

10. The embodiment of any of paragraphs 1-4 and 8-9, wherein Formula I can be represented by Structure I-B:

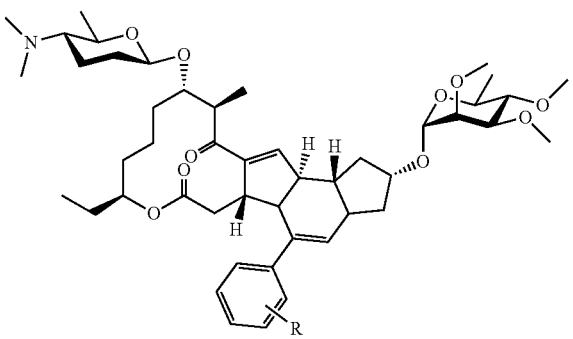

wherein R is selected from hydrogen, methoxy, ethoxy, chloro, fluoro, trifluoromethoxy, or methyl acetate.

11. The embodiment of any of paragraphs 1-4 wherein $R^2$ is hydrogen and $R^3$ is an unsubstituted or substituted triazole.

12. The embodiment of any of paragraphs 1-4 and 11, wherein the substituted triazole is a substituted or unsubstituted phenyl triazole.

13. The embodiment of paragraph 12, wherein the phenyl group of the substituted phenyl triazole may be substituted with alkyl (e.g. methyl), alkoxy (e.g. methoxy), aryl (e.g. phenyl), amino, or halogen (e.g. chloro or fluoro).

14. The embodiment of any of paragraphs 1-4 and 11-13 wherein Formula I can be represented by Structure I-C:

wherein R is selected from alkyl (e.g. methyl), alkoxy (e.g. methoxy), aryl (e.g. phenyl), amino, or halogen (e.g. chloro or fluoro).

15. The embodiment of any of the preceeding paragraphs wherein the spinosyn compound is one of the compounds shown in Table 1.

16. The embodiment of any of paragraphs 1-4, wherein the spinosyn compound is (2S,5bS,9S,13S, 14R, 16aS, 16bS)-4-chloro-13-{[(2R,5S,6R)-5-(dimethylamino)-6-methyloxan-2-yl]oxy}-9-ethyl-4-methyl-2-{[(2R,3R,4R,5S,6S)-3,4,5-trimethoxy-6-methyloxan-2-yl]oxy})-1H,2H,3H,3aH,5aH,5bH,6H,7H,9H,10H,11H,12H,13H,14H,15H,16aH,16bH-as-indaceno[3,2-d]oxacyclododecane-7,15-dione.

17. The embodiment of any of paragraphs 1-7, wherein the spinosyn compound is (2S,5bS,9S,13S, 14R, 16aS, 16bS)-13-{[(2R,5S,6R)-5-(dimethylamino)-6-methyloxan-2-yl]oxy}-9-ethyl-14-methyl-4-phenyl-2-{[(2R,3R,4R,5S,6S)-3,4,5-trimethoxy-6-methyloxan-2-yl]oxy})-1H,2H,3H,3aH,5aH,5bH,6H,7H,9H,10H,11H,12H,13H,14H,15H,16aH,16bH-as-indaceno[3,2-d]oxacyclododecane-7,15-dione.

18. The embodiment of any of paragraphs 1-7, wherein the spinosyn compound is (2S,5bS,9S,13S, 14R, 16aS, 16bS)-13-{[(2R,5S,6R)-5-(dimethylamino)-6-methyloxan-2-yl]oxy}-9-ethyl-4-(4-methoxyphenyl)-14-methyl-2-{[(2R,3R,4R,5S,6S)-3,4,5-trimethoxy-6-methyloxan-2-yl]oxy})-1H,2H,3H,3aH,5aH,5bH,6H,7H,9H,10H,11H,12H,13H,14H,15H,16aH,16bH-as-indaceno[3,2-d]oxacyclododecane-7,15-dione.

19. The embodiment of any of paragraphs 1-4 and 11-14, wherein the spinosyn compound is (2S,3aR,5aR,5bS,9S,13S,14R,16aS,16bS)-13-{[(2R,5S,6R)-5-(dimethylamino)-6-methyloxan-2-yl]oxy}-9-ethyl-14-methyl-4-(4-phenyl-1H-1,2,3-triazol-1-yl)-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione.

20. The embodiment of any of paragraphs 1-4 and 11-14, wherein the spinosyn compound is (2S,3aR,5aR,5bS,9S,13S,14R,16aS,16bS)-9-ethyl-4-[4-(4-methoxyphenyl)-1H-1,2,3-triazol-1-yl]-14-methyl-13-{[(2R,5S,6R)-6-methyl-5-(methylamino)oxan-2-yl]oxy})-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione.

21. The embodiment of any of paragraphs 1-7, wherein the spinosyn compound is (2S,5bS,9S,13S, 14R, 16aS, 16bS)-13-{[(2R,5S,6R)-5-(dimethylamino)-6-methyloxan-2-yl]oxy}-2-{[(2R,3R,4R,5S,6S)-4-ethoxy-3,5-dimethoxy-6-methyloxan-2-yl]oxy}-9-ethyl-14-methyl-4-phenyl-1H,2H,3H,3aH,5aH,5bH,6H,7H,9H,10H,11H,12H,13H,14H,15H,16aH,16bH-as-indaceno[3,2-d]oxacyclododecane-7,15-dione.

22. The embodiment of any of paragraphs 1-4 and 11-14, wherein the spinosyn compound is (2S,5b S,9S,13S,14R,16aS,16bS)-13-{[(2R,5S,6R)-5-(dimethylamino)-6-methyloxan-2-yl]oxy}-2-{[(2R,3R,4R,5S,6S)-4-ethoxy-3,5-dimethoxy-6-methyloxan-2-yl]oxy}-9-ethyl-14-methyl-4-(4-phenyl-1H-1,2,3-triazol-1-yl)-1H,2H,3H,3aH,5aH,5bH,6H,7H,9H,10H,11H,12H,13H,14H,15H,16aH,16bH-as-indaceno[3,2-d]oxacyclododecane-7,15-dione.

23. A formulation comprising at least one spinosyn compound of any of the preceeding paragraphs and an acceptable carrier.

24. The embodiment of paragraph 23, further comprising at least one additional active ingredient.

25. The embodiment of any of paragraph 23-24, further comprising at least one plant or plant product treatment compound.

26. The embodiment of any of paragraph 23-25, wherein the additional active ingredient comprises an insecticide or a miticide.

27. The embodiment of any of paragraph 23-26, wherein the insecticide is a contact-acting insecticide.

28. The embodiment of any of paragraph 23-26, wherein the miticide is a contact-acting miticide.

29. A method for controlling pests comprises contacting a pest with an effective amount of a spinosyn compound of any of paragraphs 1-22 or a formulation of any of embodiments 23-28.

30. The embodiment of paragraph 29, wherein the pest is an insect.

31. The embodiment of any of paragraphs 29-30, wherein the pest is an arachnid.

32. The embodiment of paragraphs 29-30, wherein the pest is a nematode.

33. A method for making a spinosyn compound as shown in the Examples and other disclosure herein.

The routes below illustrate general methods of synthesizing compounds of Formula (I) and/or pharmaceutically acceptable salts thereof. The skilled artisan will appreciate that the compounds described herein could be made by methods other than those specifically described herein, by adaptation of the methods described herein and/or by adaptation of methods known in the art. For example, compounds described herein can be made using other spinosyn derivatives (e.g. spinetoram, spinosyn J, or spinosyn L) as starting materials. In general, compounds provided herein may be prepared in a multi-step synthesis, as shown below. All quantities shown are approximate, and are given solely for illustrative purposes.

The examples below are intended to further illustrate certain aspects of the methods and compounds described herein, and are not intended to limit the scope of the claims.

EXPERIMENTAL

Intermediate 1: (1S,2R,6R,8S,10S,11R,15R,16S, 20S)-16-{[(2R,5S,6R)-5-(dimethylamino)-6-methyloxan-2-yl]oxy}-20-ethyl-15-methyl-8-{[(2R,3R,4R,5S,6S)-3,4,5-trimethoxy-6-methyloxan-2-yl]oxy}-4,21-dioxapentacyclo[11.10.0.0$^{2,11}$.0$^{3,5}$.0.0$^{6,10}$]tricos-12-ene-14,22-dione

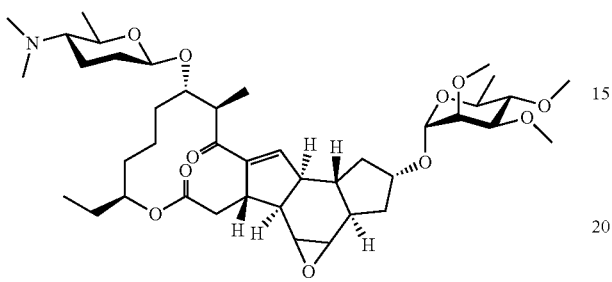

To a solution of Spinosyn A (2.5 g, 3.42 mmol) in dichloromethane (50 mL) at 0° C. was added m-CPBA (1.76 g, 10.26 mmol). The mixture was stirred at r.t. for 3 h. 50 mL aqueous Na$_2$SO$_3$ was added into the mixture. The mixture was stirred at RT for 2 h before it was extracted with dichloromethane (50 mL×2). The organic layer was separated, dried over sodium sulfate, filtered and concentrated. The residue was purified by silica gel column (dichloromethane:methanol 100:1~10:1) to afford the title compound (2.0 g, yield 78%) as a yellow solid.

Intermediate 2: (2S,3aR,5aR,5bS,9S,13S,14R,16aR,16bS)-4-azido-13-{[(2R,5S,6R)-5-(dimethylamino)-6-methyloxan-2-yl]oxy}-9-ethyl-5-hydroxy-14-methyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione

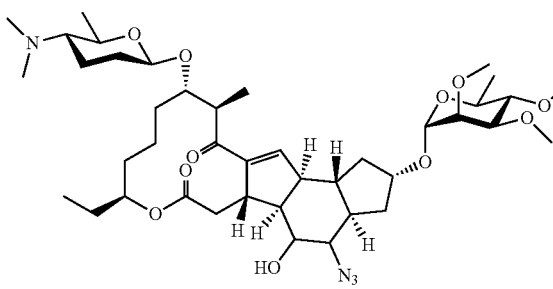

A mixture of Intermediate 1 (7 g, 9.0 mmol) and sodium azide (3.5 g, 54.3 mmol) in DMF (60 mL) was stirred at 60° C. for 2 h. The reaction mixture was cooled to r.t and filtered through kieselguhr. The filtrate was poured into saturated sodium bicarbonate (100 mL). The mixture was extracted with ethyl acetate (3×100 mL). The combined organic layer was dried over sodium sulfate, filtered and concentrated. The residue was purified by flash to afford Intermediate 2 (4.5 g, 63% yield) as a white solid. LCMS: m/z 791.9 [M+H]$^+$.

Examples 1 and 2: (2S,5bS,9S,13S,14R,16aR,16bR)-5-chloro-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione (1), and (2S,5bS,9S,13S,14R,16aS,16bS)-4-chloro-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione (2)

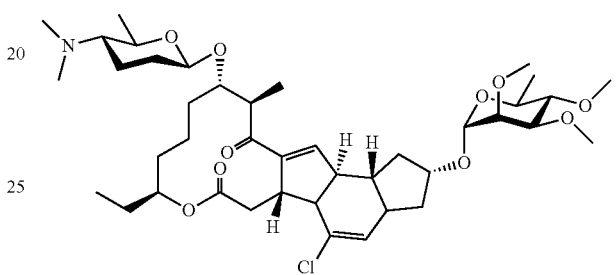

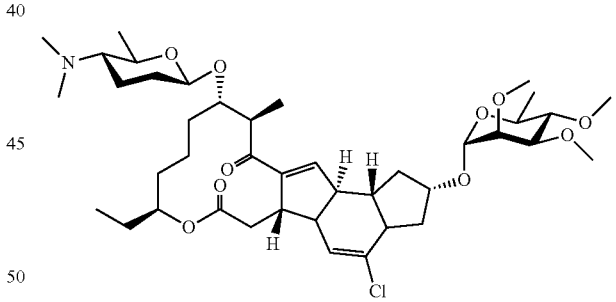

To a solution of Spinosyn A (10.0 g, 13.7 mmol) in dichloromethane (150 mL) was added PhSeCl (3.41 g, 17.8 mmol) under N$_2$ at 0° C., and the mixture was stirred for 30 min, at which point m-CPBA (60%, 5.12 g, 17.8 mmol) in dichloromethane (100 mL) was added. After stirring for 20 min at 0° C., triethylamine (20 mL) was added. After stirring for another 15 min, the reaction mixture was diluted with dichloromethane (200 mL) and washed with 10% aqueous NaHSO$_3$ (100 mL×2), water (100 mL), 5% sodium bicarbonate (100 mL×3), and water (100 mL). The organic layer was dried over anhydrous sodium sulfate, filtered and concentrated. The residue was purified column chromatography and prep-HPLC to afford Example 1 (4.2 g, 40% yield, white solid) and Example 2 (1.57 g, 15% yield, white solid).

Example 1: ¹H NMR (400 MHz, CDCl$_3$): δ 6.73 (s, 1H), 5.98 (s, 1H), 4.83 (d, J=1.6 Hz, 1H), 4.74-4.67 (m, 1H), 4.42-4.40 (m, 1H), 4.35-4.30 (m, 1H), 3.90 (tt, J$_1$=8.4 Hz, J$_2$=2.4 Hz, 1H), 3.66-3.62 (m, 1H), 3.56 (s, 3H), 3.54-3.47 (m, 8H), 3.45 (dd, J$_1$=9.2 Hz, J$_2$=3.2 Hz, 1H), 3.40-3.38 (m, 1H), 3.32-3.26 (m, 1H), 3.14-3.09 (m, 2H), 3.03-2.97 (m, 1H), 2.88 (dd, J$_1$=14.0 Hz, J$_2$=2.8 Hz, 1H), 2.30-2.20 (m, 10H), 1.99-1.72 (m, 4H), 1.60-1.30 (m, 15H), 1.27 (t, J=6.8 Hz, 6H), 1.18 (d, J=6.8 Hz, 3H), 1.00-0.88 (m, 1H), 0.82 (t, J=7.2 Hz, 3H); LCMS: m/z 765.8 [M+H]$^+$;

Example 2: ¹H NMR (400 MHz, CDCl$_3$): δ 6.71 (s, 1H), 5.90 (s, 1H), 4.85 (s, 1H), 4.68-4.66 (m, 1H), 4.43-4.41 (m, 1H), 4.44-4.29 (m, 1H), 3.67-3.44 (m, 17H), 3.29-3.22 (m, 1H), 3.16-3.06 (m, 3H), 2.86-2.81 (m, 1H), 2.87-2.52 (m, 1H), 2.39-2.23 (m, 10H), 2.07-1.34 (m, 16H), 1.29-1.22 (m, 6H), 1.18 (d, J=6.8 Hz, 3H), 0.82 (t, J=7.2 Hz, 3H); LCMS: m/z 766.3 [M+H]$^+$.

Example 3: (2S,5bS,9S,13S,14R,16aR,16bR)-13-{[(2R,5S,6R)-5-(dimethylamino)-6-methyloxan-2-yl]oxy})-9-ethyl-5-(4-methoxyphenyl)-14-methyl-2-{[(2R,3R,4R,5S,6S)-3,4,5-trimethoxy-6-methyl-oxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione

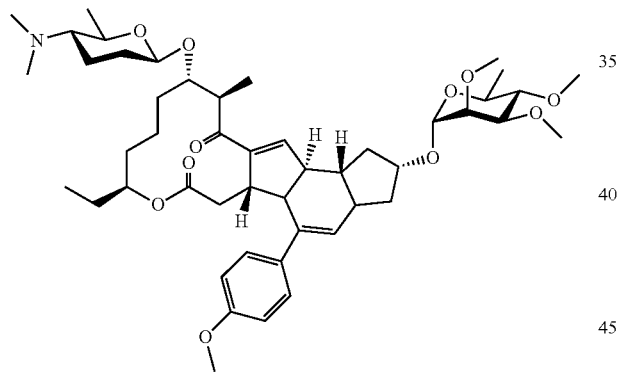

To a solution of Example 1 (383 mg, 0.5 mol) and 4-methoxyphenylboronic acid (152 mg, 1 mmol) in toluene (10 mL) was added Pd(dppf)Cl$_2$ (36 mg, 0.05 mmol) and potassium carbonate (138 mg, 1 mmol). The system was charged with N$_2$ 3 times and stirred at 110° C. for 72 h. The reaction mixture was diluted with water (30 mL) and extracted with ethyl acetate (50 mL×3). The combined organic phase was washed with brine (30 mL), dried over anhydrous sodium sulfate, filtered and concentrated. The residue was purified by prep-HPLC to afford the title compound (40 mg, 9.5% yield) as a white solid. ¹H NMR (400 MHz, Acetone-d$_6$): δ 7.19 (d, J=8.4 Hz, 2H), 7.02 (s, 1H), 6.76 (d, J=8.4 Hz, 2H), 5.64 (s, 1H), 4.72 (s, 1H), 4.53-4.51 (m, 1H), 4.41 (d, J=9.2 Hz, 1H), 4.27-4.22 (m, 1H), 4.09 (t, J=8.4 Hz, 1H), 3.67-3.61 (m, 3H), 3.42-3.18 (m, 16H), 2.93-2.78 (m, 4H), 2.88 (dd, J$_1$=14.0 Hz, J$_2$=2.8 Hz, 1H), 2.37 (s, 6H), 2.28-2.22 (m, 1H), 2.15-2.09 (m, 1H), 1.96 (s, 3H), 1.90-1.86 (m, 2H), 1.74-1.62 (m, 20H), 1.06 (d, J=6.4 Hz, 3H), 0.99 (d, J=6.8 Hz, 2H), 0.93-0.82 (m, 1H), 0.76-0.73 (m, 1H), 0.65 (t, J=7.2 Hz, 3H); LCMS: m/z 837.9 [M−H]$^+$.

Example 4: (2S,5bS,9S,13S,14R,16aS,16bS)-13-{[(2R,5S,6R)-5-(dimethylamino)-6-methyloxan-2-yl]oxy})-9-ethyl-4-(4-methoxyphenyl)-14-methyl-2-{[(2R,3R,4R,5S,6S)-3,4,5-trimethoxy-6-methyl-oxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione

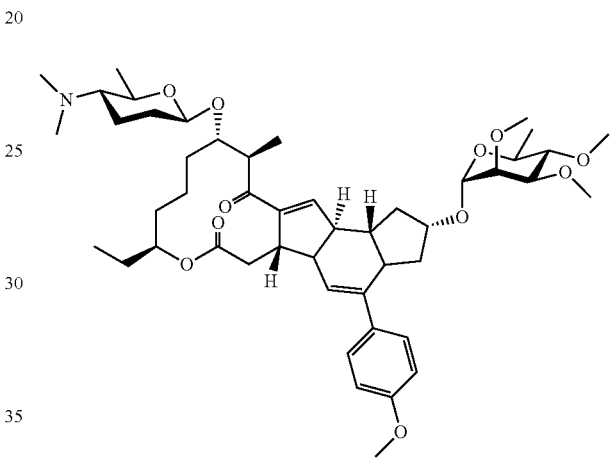

To a solution of Example 2 (383 mg, 0.5 mol) and 4-methoxyphenylboronic acid (152 mg, 1 mmol) in toluene (10 mL) was added Pd(dppf)Cl$_2$ (36 mg, 0.05 mmol) and potassium carbonate (138 mg, 1 mmol). The system was charged with N$_2$ 3 times and stirred at 110° C. for 72 h. The reaction mixture was diluted with water (30 mL) and extracted with ethyl acetate (3×50 mL). The combined organic phase was washed with brine (30 mL), dried over anhydrous sodium sulfate, filtered and concentrated. The residue was purified by prep-HPLC to afford the title compound (50 mg, 11.9% yield) as a white solid. ¹H NMR (400 MHz, Acetone-d$_6$): δ 7.12 (d, J=8.8 Hz, 2H), 6.97 (s, 1H), 6.75 (d, J=8.4 Hz, 2H), 5.79 (t, J=2.4 Hz, 1H), 4.67 (d, J=1.6 Hz, 1H), 4.56-4.52 (m, 1H), 4.35 (d, J=9.2 Hz, 1H), 4.16-4.11 (m, 1H), 3.66 (s, 3H), 3.56 (tt, J$_1$=8.4 Hz, J$_2$=2.4 Hz, 1H), 3.47-3.27 (m, 14H), 3.23-3.19 (m, 1H), 3.01-2.87 (m, 3H), 2.81-2.76 (m, 1H), 2.67-2.58 (m, 3H), 2.43 (dd, J$_1$=14.0 Hz, J$_2$=2.8 Hz, 1H), 2.31-2.24 (m, 1H), 2.09 (s, 3H), 2.02-1.95 (m, 2H), 1.83-1.79 (m, 1H), 1.72-1.64 (m, 2H), 1.47-1.12 (m, 12H), 1.10-1.00 (m, 11H), 0.68 (t, J=7.6 Hz, 3H); LCMS: m/z 837.9 [M−H]$^+$.

Example 5: (2S,5bS,9S,13S,14R,16aS,16bS)-13-
{[(2R,5S,6R)-5-(dimethylamino)-6-methyloxan-2-
yl]oxy}-9-ethyl-14-methyl-4-phenyl-2-{[(2R,3R,4R,
5S,6S)-3,4,5-trimethoxy-6-methyloxan-2-yl]oxy}-
1H,2H,3H,3aH,5aH,5bH,6H,7H,9H,10H,11H,12H,
13H,14H,15H,16aH,16bH-as-indaceno[3,2-d]
oxacyclododecane-7,15-dione

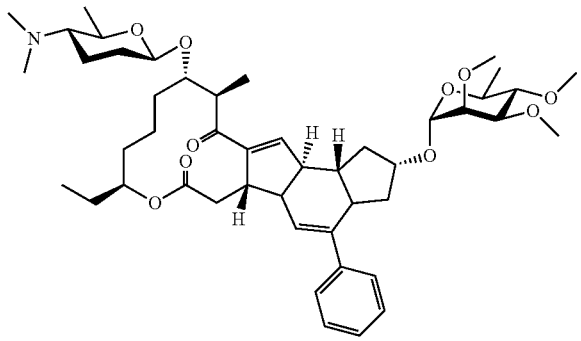

To a solution of Example 2 (383 mg, 0.5 mol) and phenylboronic acid (152 mg, 1 mmol) in toluene (10 mL) was added Pd(dppf)Cl$_2$ (36 mg, 0.05 mmol) and potassium carbonate (138 mg, 1 mmol). The system was charged with N$_2$ 3 times and stirred at 110° C. for 72 h. The reaction mixture was diluted with water (30 mL) and extracted with ethyl acetate (50 mL×3). The combined organic phase was washed with brine (30 mL), dried over anhydrous sodium sulfate, filtered and concentrated. The residue was purified by prep-HPLC to afford the title compound (35 mg, 8.7% yield) as a white solid. $^1$H NMR (400 MHz, Acetone-d$_6$): δ 7.34-7.29 (m, 4H), 7.24-7.21 (m, 1H), 7.11 (s, 1H), 6.00 (t, J=2.8 Hz, 1H), 4.80 (d, J=2.0 Hz, 1H), 4.71-4.64 (m, 1H), 4.48 (d, J=9.2 Hz, 1H), 4.30-4.24 (m, 1H), 3.75-3.69 (m, 1H), 3.60-3.41 (m, 15H), 3.37-3.33 (m, 1H), 3.15-3.08 (m, 2H), 3.02 (t, J=9.6 Hz, 1H), 2.97-2.92 (m, 1H), 2.65-2.56 (m, 1H), 2.45-2.39 (m, 1H), 2.22 (s, 6H), 2.17-2.09 (m, 2H), 1.96-1.93 (m, 1H), 1.85-1.79 (m, 2H), 1.60-1.35 (m, 20H), 0.90-0.87 (m, 1H), 0.81 (t, J=7.6 Hz, 3H); LCMS: m/z 808.4 [M+H]$^+$.

Example 6: (2S,5bS,9S,13S,14R,16aR,16bR)-5-(3-chlorophenyl)-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione

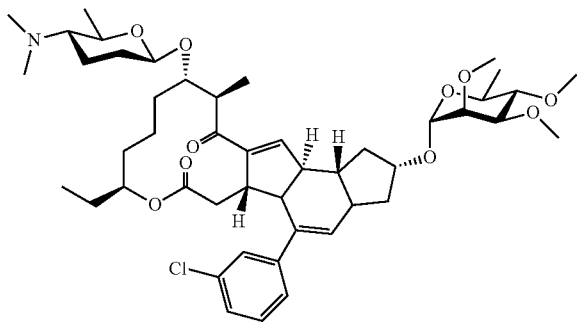

To a solution of Example 1 (383 mg, 0.5 mol) and 3-chlorophenylboronic acid (156 mg, 1 mmol) in toluene (10 mL) was added Pd(dppf)Cl$_2$ (36 mg, 0.05 mmol) and potassium carbonate (138 mg, 1 mmol). The system was charged with N$_2$ 3 times and stirred at 110° C. for 72 h. The reaction mixture was diluted with water (30 mL) and extracted with ethyl acetate (50 mL×3). The combined organic phase was washed with brine (30 mL), dried over anhydrous sodium sulfate, filtered and concentrated. The residue was purified by prep-HPLC to afford the title compound (35 mg, 8.3% yield) as a white solid. $^1$H NMR (400 MHz, Acetone-d$_6$): δ 7.44-7.43 (m, 1H), 7.40-7.34 (m, 2H), 7.33-7.30 (m, 1H), 7.15 (s, 1H), 5.91 (s, 1H), 4.85 (d, J=2.0 Hz, 1H), 4.70-4.64 (m, 1H), 4.46 (dd, J$_1$=9.2 Hz, J$_2$=2.0 Hz, 1H), 4.41-4.36 (m, 1H), 4.26 (tt, J$_1$=8.4 Hz, J$_2$=2.0 Hz, 1H), 3.60-3.39 (m, 15H), 3.35-3.29 (m, 1H), 3.03 (t, J=9.2 Hz, 2H), 2.96-2.94 (m, 1H), 2.81-2.76 (m, 1H), 2.43-2.36 (m, 1H), 2.34-2.26 (m, 1H), 2.20 (s, 6H), 2.17-2.06 (m, 2H), 2.04-2.01 (m, 1H), 1.95-1.91 (m, 1H), 1.85-1.73 (m, 3H), 1.59-1.29 (m, 20H), 1.20-1.81 (m, 6H), 1.12 (d, J=6.8 Hz, 3H), 1.08-1.00 (m, 1H), 0.90-0.87 (m, 1H), 0.78 (t, J=7.2 Hz, 3H); LCMS: m/z 841.8 [M−H]$^+$.

Example 7: (2S,5bS,9S,13S,14R,16aR,16bR)-13-
{[(2R,5S,6R)-5-(dimethylamino)-6-methyloxan-2-
yl]oxy}-9-ethyl-5-(3-methoxyphenyl)-14-methyl-2-
{[(2R,3R,4R,5S,6S)-3,4,5-trimethoxy-6-methyl-
oxan-2-yl]oxy}-1H,2H,3H,3aH,5aH,5bH,6H,7H,9H,
10H,11H,12H,13H,14H,15H,16aH,16bH-as-indaceno[3,2-d]oxacyclododecane-7,15-dione

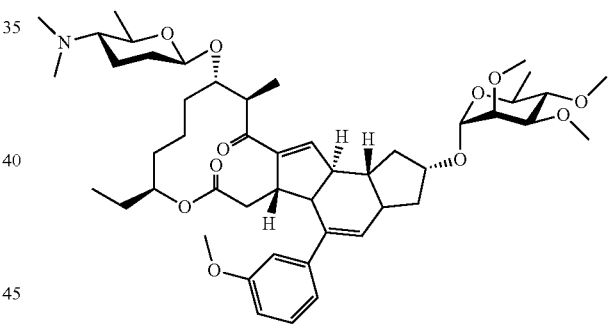

To a solution of Example 1 (383 mg, 0.5 mol) and 3-methoxyphenylboronic acid (152 mg, 1 mmol) in toluene (10 mL) was added Pd(dppf)Cl$_2$ (36 mg, 0.05 mmol) and potassium carbonate (138 mg, 1 mmol). The system was charged with N$_2$ 3 times and stirred at 110° C. for 72 h. The reaction mixture was diluted with water (30 mL) and extracted with ethyl acetate (3×50 mL). The combined organic phase was washed with brine (30 mL), dried over anhydrous sodium sulfate, filtered and concentrated. The residue was purified by prep-HPLC to afford the title compound (45 mg, 10.7% yield) as a white solid. $^1$H NMR (400 MHz, Acetone-d$_6$): δ 7.26 (t, J=7.6 Hz, 1H), 7.15 (s, 1H), 7.02-6.95 (m, 2H), 6.84 (dd, J$_1$=8.0 Hz, J$_2$=2.4 Hz, 1H), 5.86 (s, 1H), 4.85 (d, J=1.6 Hz, 1H), 4.70-4.64 (m, 1H), 4.45 (dd, J$_1$=9.2 Hz, J$_2$=1.6 Hz, 1H), 4.41-4.35 (m, 1H), 4.27 (tt, J$_1$=8.4 Hz, J$_2$=2.0 Hz, 1H), 3.80 (s, 3H), 3.57-3.30 (m, 16H), 3.06-2.98 (m, 2H), 2.96-2.94 (m, 1H), 2.79-2.72 (m, 4H), 2.42-2.36 (m, 1H), 2.32-2.24 (m, 1H), 2.20 (s, 6H), 2.14-2.07 (m, 2H), 2.02-2.00 (m, 1H), 1.95-1.72 (m, 5H), 1.60-1.29 (m, 21H), 1.20-1.18 (m, 6H), 1.12 (d, J=6.8 Hz, 3H), 1.05-1.00 (m, 2H), 0.90-0.84 (m, 3H), 0.77 (t, J=7.6 Hz, 3H); LCMS: m/z 838.3 [M+H]$^+$.

Example 8: (2S,5bS,9S,13S,14R,16aS,16bS)-13-{[(2R,5S,6R)-5-(dimethylamino)-6-methyloxan-2-yl]oxy}-9-ethyl-4-(3-methoxyphenyl)-14-methyl-2-{[(2R,3R,4R,5S,6S)-3,4,5-trimethoxy-6-methyl-oxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione

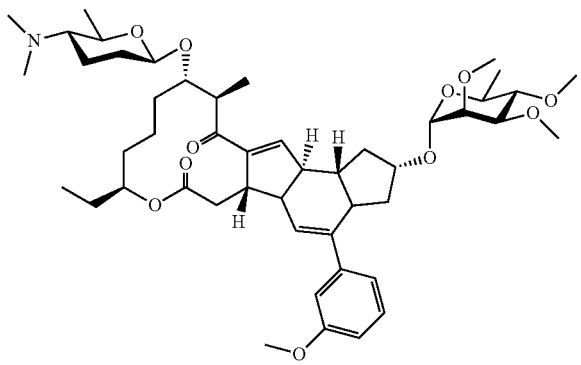

To a solution of Example 2 (383 mg, 0.5 mol) and 3-methoxyphenylboronic acid (152 mg, 1 mmol) in toluene (10 mL) was added Pd(dppf)Cl$_2$ (36 mg, 0.05 mmol) and potassium carbonate (138 mg, 1 mmol). The system was charged with N$_2$ 3 times and stirred at 110° C. for 72 h. The reaction mixture was diluted with water (30 mL) and extracted with ethyl acetate (3×50 mL). The combined organic phase was washed with brine (30 mL), dried over anhydrous sodium sulfate, filtered and concentrated. The residue was purified by prep-HPLC to afford the title compound (50 mg, 11.9% yield) as a white solid. $^1$H NMR (400 MHz, Acetone-d$_6$): δ 7.22 (t, J=7.6 Hz, 1H), 7.09 (s, 1H), 6.90-6.88 (m, 2H), 6.80 (dd, J$_1$=8.0 Hz, J$_2$=2.4 Hz, 1H), 6.02 (t, J=2.8 Hz, 1H), 4.81 (d, J=1.6 Hz, 1H), 4.70-4.65 (m, 1H), 4.48 (dd, J=9.2 Hz, J$_2$=1.6 Hz, 1H), 4.29-4.24 (m, 1H), 3.80 (s, 3H), 3.74-3.68 (m, 1H), 3.61-3.42 (m, 16H), 3.37-3.32 (m, 1H), 3.15-3.10 (m, 2H), 3.02 (t, J=6.4 Hz, 1H), 2.95-2.90 (m, 1H), 2.82-2.72 (m, 3H), 2.58-2.54 (m, 1H), 2.44-2.38 (m, 1H), 2.22 (s, 6H), 2.16-2.04 (m, 2H), 1.95 (d, J=11.6 Hz, 1H), 1.85-1.77 (m, 2H), 1.59-1.24 (m, 14H), 1.22-1.14 (m, 11H), 0.81 (t, J=7.6 Hz, 3H); LCMS: m/z 838.4 [M+H]$^+$.

Example 9: (2S,5bS,9S,13S,14R,16aS,16bS)-4-(4-chlorophenyl)-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione

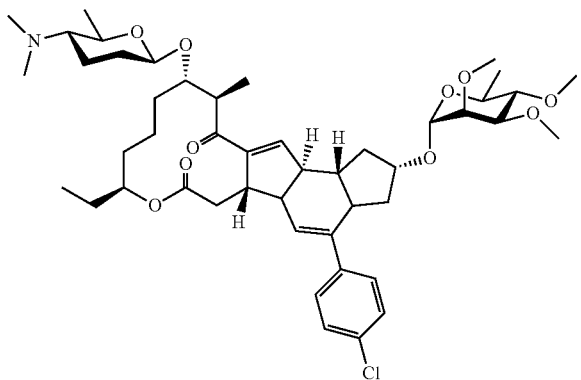

To a solution of Example 2 (383 mg, 0.5 mol) and 4-chlorophenylboronic acid (156 mg, 1 mmol) in toluene (10 mL) was added Pd(dppf)Cl$_2$ (36 mg, 0.05 mmol) and potassium carbonate (138 mg, 1 mmol). The system was charged with N$_2$ 3 times and stirred at 110° C. for 72 h. The reaction mixture was diluted with water (30 mL) and extracted with ethyl acetate (3×50 mL). The combined organic phase was washed with brine (100 mL), dried over anhydrous sodium sulfate, filtered and concentrated. The residue was purified by prep-HPLC to afford the title compound (35 mg, 8.3% yield) as a white solid. $^1$H NMR (400 MHz, Acetone-d$_6$): δ 7.37-7.31 (m, 4H), 7.10 (s, 1H), 6.75 (d, J=8.4 Hz, 2H), 6.05 (t, J=2.8 Hz, 1H), 5.35 (t, J=4.8 Hz, 1H), 4.81 (d, J=2.4 Hz, 1H), 4.70-4.54 (m, 1H), 4.48 (dd, J$_1$=9.6 Hz, J$_2$=1.6 Hz, 1H), 4.30-4.25 (m, 1H), 3.75-3.69 (m, 1H), 3.62-3.50 (m, 4H), 3.47 (s, 3H), 3.43-3.40 (m, 7H), 3.36-3.32 (m, 1H), 3.14-3.10 (m, 2H), 3.02 (t, J=9.6 Hz, 1H), 2.96-2.91 (m, 1H), 2.60-2.55 (m, 1H), 2.45-2.37 (m, 1H), 2.22 (s, 1H), 2.16-2.08 (m, 3H), 2.67-2.58 (m, 3H), 1.96-1.78 (m, 3H), 1.58-1.28 (m, 20H), 1.22-1.13 (m, 12H), 0.88 (t, J=7.6 Hz, 3H), 0.80 (t, J=7.6 Hz, 3H); LCMS: m/z 841.8 [M+H]$^+$.

Example 10: (2S,5bS,9S,13S,14R,16aR,16bR)-13-{[(2R,5S,6R)-5-(dimethylamino)-6-methyloxan-2-yl]oxy}-9-ethyl-5-(3-fluorophenyl)-14-methyl-2-{[(2R,3R,4R,5S,6S)-3,4,5-trimethoxy-6-methyl-oxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione

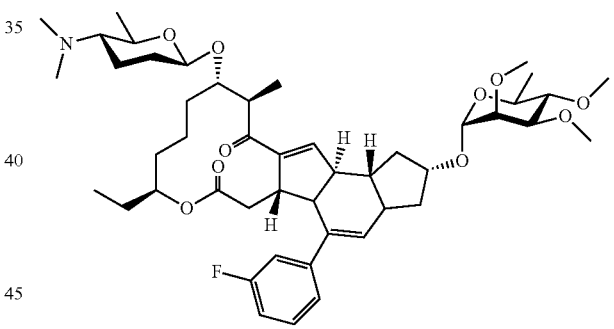

To a solution of Example 1 (383 mg, 0.5 mol) and 3-fluorophenylboronic acid (140 mg, 1 mmol) in toluene (10 mL) was added Pd(dppf)Cl$_2$ (36 mg, 0.05 mmol) and potassium carbonate (138 mg, 1 mmol). The system was charged with N$_2$ 3 times and stirred at 110° C. for 72 h. The reaction was quenched with water (30 mL) and extracted with ethyl acetate (50 mL×3). The combined organic phase was washed with brine (100 mL), dried over anhydrous sodium sulfate, filtered and concentrated. The residue was purified by prep-HPLC to afford the title compound (50 mg, 12.1% yield) as a white solid. $^1$H NMR (400 MHz, Acetone): δ 7.45-7.41 (m, 2H), 7.14 (s, 1H), 7.10 (t, J=8.8 Hz, 2H), 5.83 (s, 1H), 4.85 (d, J=1.6 Hz, 1H), 4.68-4.62 (m, 1H), 4.46-4.43 (m, 1H), 4.40-4.35 (m, 1H), 4.22 (m, 1H), 3.57-3.37 (m, 15H), 3.35-3.31 (m, 1H), 3.06-3.01 (m, 2H), 2.42-2.37 (m, 1H), 2.31-2.24 (m, 1H), 2.20 (s, 6H), 2.14-2.10 (m, 1H), 1.95-1.73 (m, 4H), 1.59-1.30 (m, 12H), 1.19 (dd, J$_1$=6.0 Hz, J$_2$=2.0 Hz, 1H), 1.12 (d, J=7.8 Hz, 3H), 1.08-0.98 (m, 1H), 0.78 (t, J=7.2 Hz, 3H); LCMS: m/z 825.8 [M+H]$^+$.

Example 11: (2S,5bS,9S,13S,14R,16aR,16bR)-5-(4-chlorophenyl)-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione

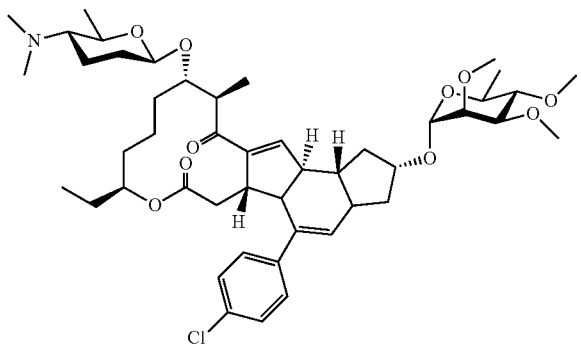

To a solution of Example 1 (383 mg, 0.5 mol) and 4-chlorobenzeneboronic acid (156 mg, 1 mmol) in toluene (10 mL) was added Pd(dppf)Cl$_2$ (36 mg, 0.05 mmol) and potassium carbonate (138 mg, 1 mmol). The system was charged with N$_2$ 3 times and stirred at 110° C. for 72 h. The reaction mixture was diluted with water (30 mL) and extracted with ethyl acetate (3×50 mL). The combined organic phase was washed with brine (100 mL), dried over anhydrous sodium sulfate, filtered and concentrated. The residue was purified by prep-HPLC to afford the title compound (30 mg, 7.1% yield) as a white solid. $^1$H NMR (400 MHz, Acetone): δ 7.42 (d, J=8.4 Hz, 2H), 7.36 (d, J=8.4 Hz, 2H), 7.15 (s, 1H), 5.87 (s, 1H), 4.35 (t, J=4.8 Hz, 1H), 4.85 (d, J=2.0 Hz, 1H), 4.69-4.62 (m, 1H), 4.44 (d, J$_1$=10.4 Hz, J$_2$=2.0 Hz, 1H), 4.40-4.35 (m, 1H), 4.23 (t, J=8.8 Hz, 1H), 3.57-3.31 (m, 16H), 3.03 (t, J=4.8 Hz, 2H), 2.96-2.92 (m, 1H), 2.82-2.74 (m, 7H), 2.43-2.36 (m, 1H), 2.20 (s, 6H), 2.16-2.12 (m, 3H), 1.95-1.91 (m, 1H), 1.84-1.76 (m, 3H), 1.60-1.30 (m, 18H), 1.19 (d, J=6.8 Hz, 6H), 1.11 (d, J=7.2 Hz, 3H), 1.06-1.00 (m, 2H), 0.86 (t, J=7.2 Hz, 3H), 0.78 (t, J=7.2 Hz, 3H); LCMS: m/z 841.8 [M+H]$^+$.

Example 12: (2S,5bS,9S,13S,14R,16aR,16bR)-13-{[(2R,5S,6R)-5-(dimethylamino)-6-methyloxan-2-yl]oxy}-9-ethyl-14-methyl-5-[4-(trifluoromethoxy)phenyl]-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione

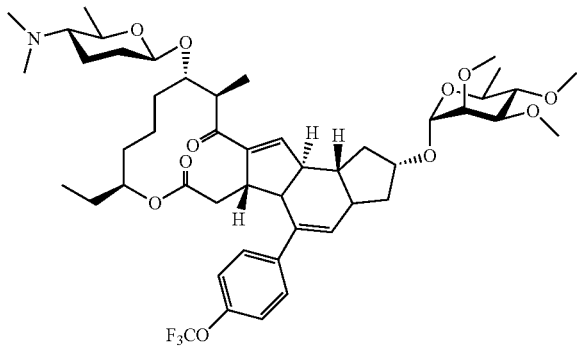

To a solution of Example 1 (383 mg, 0.5 mol) and 4-(trifluoromethoxy)phenylboronic acid (206 mg, 1 mmol) in toluene (10 mL) was added Pd(dppf)Cl$_2$ (36 mg, 0.05 mmol) and potassium carbonate (138 mg, 1 mmol). The system was charged with N$_2$ three times and stirred at 110° C. for 3 days. The reaction mixture was diluted with water (30 mL) and extracted with ethyl acetate (3×50 mL). The combined organic phase was washed with brine (100 mL), dried over anhydrous sodium sulfate, filtered and concentrated. The residue was purified by prep-HPLC to afford the title compound (80 mg, 17.9% yield) as a white solid. $^1$H NMR (400 MHz, (CD$_3$)$_2$CO): δ 7.40 (d, J=8.4 Hz, 2H), 7.17 (d, J=8.0 Hz, 2H), 7.04 (s, 1H), 5.76 (s, 1H), 4.72 (d, J=1.6 Hz, 1H), 4.54-4.48 (m, 1H), 4.31 (d, J=9.2 Hz, 1H), 4.28-4.22 (m, 1H), 4.11 (t, J=8.8 Hz, 1H), 3.45-3.16 (m, 16H), 294-2.87 (m, 2H), 2.84-2.79 (m, 1H), 2.65-2.60 (m, 1H), 2.30-2.13 (m, 2H), 2.07 (s, 6H), 2.01-1.94 (m, 1H), 1.82-1.58 (m, 4H), 1.46-1.16 (m, 16H), 1.07-1.05 (m, 6H), 0.98 (d, J=6.4 Hz, 3H), 0.94-0.89 (m, 1H), 0.64 (t, J=7.6 Hz, 3H); LCMS: m/z 892.0 [M+H]$^+$.

Example 13: (2S,5bS,9S,13S,14R,16aR,16bR)-13-{[(2R,5S,6R)-5-(dimethylamino)-6-methyloxan-2-yl]oxy}-9-ethyl-14-methyl-5-[4-(trifluoromethyl)phenyl]-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione

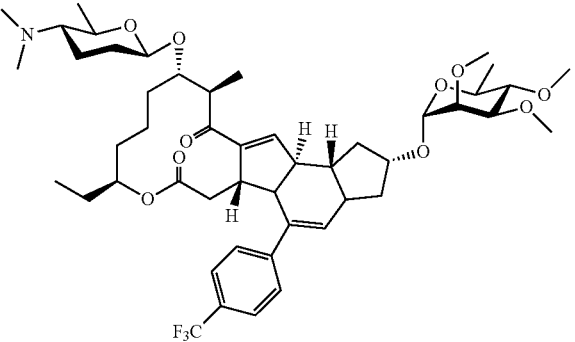

To a solution of Example 1 (383 mg, 0.5 mol) and 4-(trifluoromethyl)phenylboronic acid (190 mg, 1 mmol) in toluene (10 mL) was added Pd(dppf)Cl$_2$ (36 mg, 0.05 mmol) and potassium carbonate (138 mg, 1 mmol). The system was charged N$_2$ three times and stirred at 110° C. for 3 days. The reaction mixture was diluted with water (30 mL) and extracted with ethyl acetate (3×50 mL). The combined organic phase was washed with brine (100 mL), dried over anhydrous sodium sulfate, filtered and concentrated. The residue was purified by prep-HPLC to afford the title compound (65 mg, 14.8% yield) as a white solid. $^1$H NMR (400 MHz, Acetone): δ 7.57-7.50 (m, 4H), 7.05 (s, 1H), 5.83 (s, 1H), 4.73 (d, J=2.0 Hz, 1H), 4.54-4.49 (m, 1H), 4.31 (dd, J$_1$=9.2 Hz, J$_2$=2.0 Hz, 1H), 4.28-4.23 (m, 1H), 4.17 (tt, J$_1$=8.4 Hz, J$_2$=2.0 Hz, 1H), 3.46-3.19 (m, 16H), 2.97-2.87 (m, 2H), 2.84-2.82 (m, 1H), 2.65-2.60 (m, 1H), 2.32-2.15 (m, 2H), 2.07 (s, 6H), 1.82-1.59 (m, 4H), 1.49-1.16 (m, 11H), 1.07-1.04 (m, 6H), 0.98 (d, J=6.8 Hz, 4H), 0.64 (t, J=7.2 Hz, 3H); LCMS: m/z 876.0 [M+H]$^+$.

Example 14: (2S,5bS,9S,13S,14R,16aR,16bR)-13-{[(2R,5S,6R)-5-(dimethylamino)-6-methyloxan-2-yl]oxy}-9-ethyl-5-(4-ethylphenyl)-14-methyl-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione

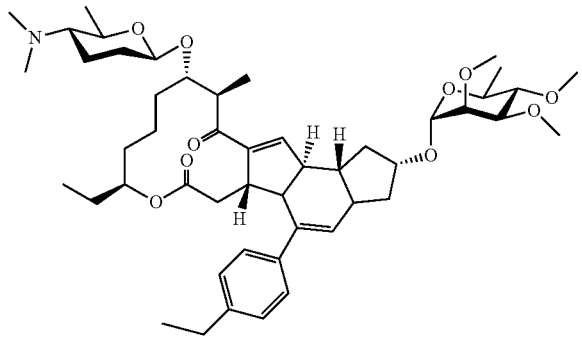

To a solution of Example 1 (383 mg, 0.5 mol) and 4-ethylphenylboronic acid (150 mg, 1 mmol) in toluene (10 mL) was added Pd(dppf)Cl$_2$ (36 mg, 0.05 mmol) and potassium carbonate (138 mg, 1 mmol). The system was charged with N$_2$ 3 times and stirred at 110° C. for 3 days. The reaction mixture was diluted with water (30 mL) and extracted with ethyl acetate (3×50 mL). The combined organic phase was washed with brine (100 mL), dried over anhydrous sodium sulfate, filtered and concentrated. The residue was purified by prep-HPLC to afford the title compound (80 mg, 19.1% yield) as a white solid. $^1$H NMR (400 MHz, Acetone): δ 7.18 (d, J=8.0 Hz, 2H), 7.05 (d, J=8.0 Hz, 2H), 7.03 (s, 1H), 7.02-6.95 (m, 2H), 5.67 (s, 1H), 4.72 (d, J=1.6 Hz, 1H), 4.54-4.49 (m, 1H), 4.31 (dd, J$_1$=9.2 Hz, J$_2$=1.6 Hz, 1H), 4.27-4.22 (m, 1H), 4.12 (tt, J=8.4 Hz, J$_2$=2.0 Hz, 1H), 3.46-3.16 (m, 17H), 2.92-2.85 (m, 2H), 2.96-2.94 (m, 2H), 2.82-2.78 (m, 1H), 2.69 (d, J=13.2 Hz, 2H), 2.58 (dd, J$_1$=11.2 Hz, J$_2$=7.2 Hz, 1H), 2.50 (q, J=7.6 Hz, 2H), 2.30-2.23 (m, 1H), 2.18-2.10 (m, 1H), 2.07 (s, 6H), 1.81-1.67 (m, 4H), 1.45-1.16 (m, 13H), 1.20-1.18 (m, 6H), 1.10-1.04 (m, 10H), 0.98 (d, J=7.2 Hz, 2H), 0.90-0.84 (m, 1H), 0.65 (t, J=7.6 Hz, 3H); LCMS: m/z 836.2 [M+H]$^+$.

Example 15: methyl 4-[(2S,5bS,9S,13S,14R,16aR,16bR)-13-{I[(2R,5S,6R)-5-(dimethylamino)-6-methyloxan-2-yl]oxy}-9-ethyl-14-methyl-7,15-dioxo-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecan-5-yl]benzoate

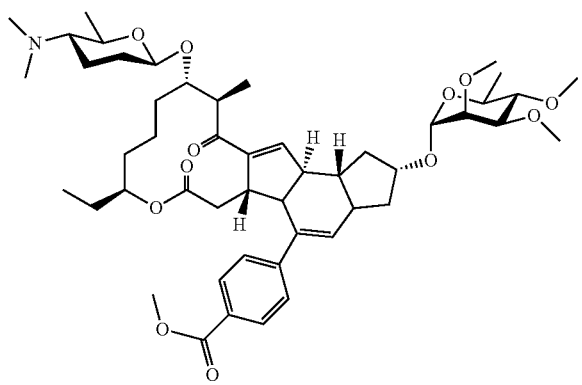

To a solution of Example 1 (383 mg, 0.5 mol) and 4-(methoxycarbonyl)phenylboronic acid (180 mg, 1 mmol) in toluene (10 mL) was added Pd(dppf)Cl$_2$ (36 mg, 0.05 mmol) and potassium carbonate (138 mg, 1 mmol). The system was charged with N$_2$ 3 times and stirred at 110° C. for 3 days. The reaction mixture was diluted with water (30 mL) and extracted with ethyl acetate (3×50 mL). The combined organic phase was washed with brine (100 mL), dried over anhydrous sodium sulfate, filtered and concentrated. The residue was purified by prep-HPLC to afford the title compound (75 mg, 17.3% yield) as a white solid. $^1$H NMR (400 MHz, Acetone): δ 7.85 (d, J=8.4 Hz, 2H), 7.42 (d, J=8.4 Hz, 2H), 7.04 (s, 1H), 5.81 (s, 1H), 4.73 (d, J=2.0 Hz, 1H), 4.55-4.49 (m, 1H), 4.31 (dd, J$_1$=9.2 Hz, J$_2$=1.6 Hz, 1H), 4.28-4.23 (m, 1H), 4.16 (tt, J$_1$=8.4 Hz, J$_2$=2.0 Hz, 1H), 3.75 (s, 3H), 3.44-3.18 (m, 16H), 3.61-3.42 (m, 16H), 2.96-2.87 (m, 2H), 2.83-2.79 (m, 1H), 2.69-2.60 (m, 2H), 2.31-2.14 (m, 2H), 2.07 (s, 6H), 1.81-1.61 (m, 4H), 1.46-1.21 (m, 12H), 1.07-1.04 (m, 7H), 0.98 (d, J=8.4 Hz, 4H), 0.64 (t, J=7.6 Hz, 3H); LCMS: m/z 866.2 [M+H]$^+$.

Representative Procedure for Synthesis of Triazoles Via Hydroxyazide Intermediates:

Intermediate 3: (2S,3aR,5aR,5bS,9S,13S,14R,16aR,16bS)-13-{[(2R,5S,6R)-5-(dimethylamino)-6-methyloxan-2-yl]oxy}-9-ethyl-4-[4-(4-fluorophenyl)-1H-1,2,3-triazol-1-yl]-5-hydroxy-14-methyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H10H,11H,12H,13H,14H,15H,16aH,16bH-as-indaceno[3,2-d]oxacyclododecane-7,15-dione

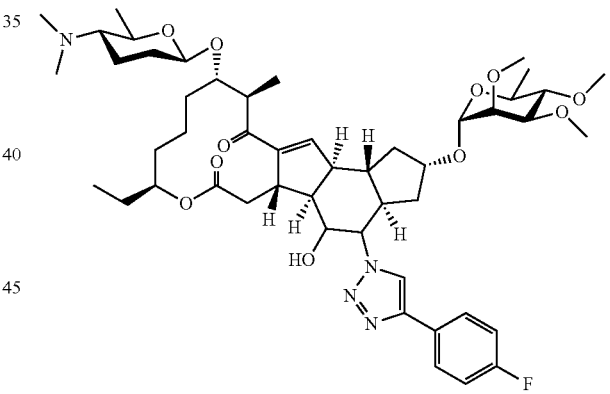

A mixture of Intermediate 2 (300 mg, 0.38 mmol), 1-ethynyl-4-fluoro-benzene (228 mg, 1.9 mmol), copper sulfate (12 mg, 0.076 mmol) and sodium ascorbate (15 mg, 0.076 mmol) in t-BuOH/water (3 mL/1.5 mL) was stirred at 100° C. for 17 h in a sealed tube. The reaction mixture was filtered through kieselguhr and the filtrate was concentrated. The residue was purified by prep-HPLC to afford the title compound (80 mg, 14% yield) as a white solid. Partial $^1$H NMR (CDCl$_3$, 400 MHz): δ 7.99 (s, 1H), 7.82-7.78 (m, 2H), 7.14-7.10 (m, 2H), 6.87 (s, 1H), 4.71 (s, 1H), 4.70-4.63 (m, 1H), 4.50 (dd, J=2.4, 11.2 Hz, 1H), 4.43 (d, J=6.8 Hz, 1H), 4.36 (s, 1H), 4.28-4.21 (m, 1H), 3.66-3.60 (m, 1H), 3.52-3.43 (m, 16H), 3.35 (s, 1H), 3.28-3.22 (m, 3H), 3.14-3.07 (m, 2H), 3.00-2.95 (m, 1H), 2.77-2.68 (m, 1H), 2.38-2.32 (m, 2H), 2.24 (s, 1H), 2.01-1.97 (m, 1H), 1.88-1.79 (m, 6H), 1.53-1.06 (m, 28H), 0.81 (t, J=7.6 Hz, 3H), LCMS: m/z 912.4 [M+H]$^+$.

Example 16: (2S,3aR,5aR,5bS,9S,13S,14R,16aS, 16bS)-13-{[(2R,5S,6R)-5-(dimethylamino)-6-methyloxan-2-yl]oxy}-9-ethyl-4-[4-(4-fluorophenyl)-1H-1,2,3-triazol-1-yl]-14-methyl-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione

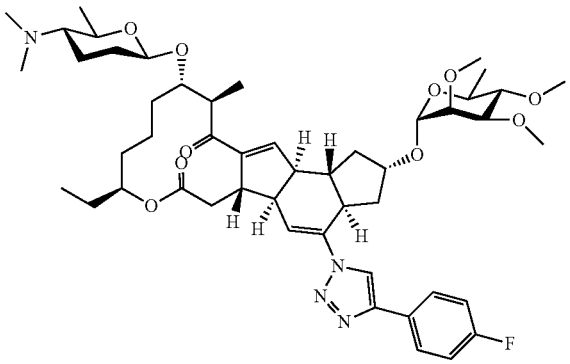

To a solution of Intermediate 3 (150 mg, 0.16 mmol) in dichloromethane (10 mL) was added DAST (53.1 mg, 0.33 mmol) at −78° C. under N$_2$. After stirring at −78° C. for 30 min, the mixture was warmed to room temperature and quenched with aqueous sodium bicarbonate (10 mL). After stirring for 15 min, the mixture was extracted with dichloromethane (10 mL×3). The combined organic layer was washed with brine, dried over sodium sulfate, filtered and concentrated. The residue was purified by prep-HPLC to afford the title compound (20 mg, yield 25%). Partial $^1$H NMR (CDCl$_3$, 400 MHz): δ7.85 (s, 1H), 7.84-7.81 (m, 2H), 7.16-7.11 (m, 2H), 6.79 (s, 1H), 6.17 (t, J=2.8 Hz, 1H), 4.81 (s, 1H), 4.72-4.69 (m, 1H), 4.72-4.69 (m, 1H), 4.43 (d, J=7.8 Hz 1H), 4.37-4.32 (m, 1H), 3.91-3.87 (m, 1H), 3.66-3.44 (m, 15H), 3.32-2.90 (m, 6H), 2.46-2.21 (m, 10H), 0.82 (t, J=7.2 Hz, 3H). LCMS: m/z 894.1 [M+H]$^+$.

Example 17: (2S,3aR,5aR,5bS,9S,13S,14R,16aS, 16bS)-13-{[(2R,5S,6R)-5-(dimethylamino)-6-methyloxan-2-yl]oxy}-9-ethyl-4-[4-(4-methoxyphenyl)-1H-1,2,3-triazol-1-yl]-14-methyl-2-{[(2R,3R,4R,5S, 6S)-3,4,5-trimethoxy-6-methyloxan-2-yl]oxy}-1H, 2H,3H,3aH,5aH,5bH,6H,7H,9H,10H,11H,12H,13H, 14H,15H,16aH,16bH-as-indaceno[3,2-d]oxacyclododecane-7,15-dione

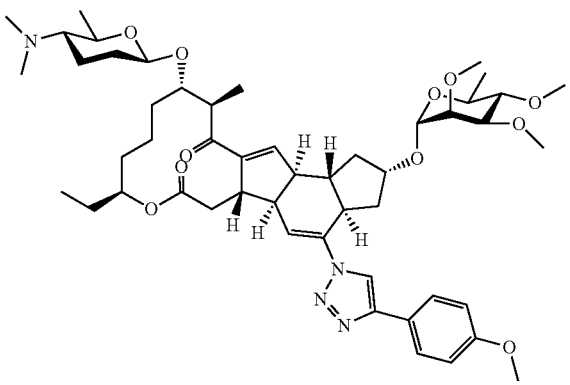

The hydroxytriazole intermediate was prepared using the representative procedure using 1-ethynyl-4-methoxybenzene. To a solution of the hydroxytriazole intermediate (80 mg, 0.08 mmol) in dichloromethane (5 mL) was added DAST (70 mg, 0.43 mmol) at −78° C. under N$_2$. After stirring at −78° C. for 30 min, the mixture was warmed to room temperature and quenched with aqueous sodium bicarbonate (10 mL). After stirring for 15 min, the mixture was extracted with dichloromethane (10 mL×2). The combined organic layer was washed with brine, dried over sodium sulfate, filtered and concentrated. The residue was purified by prep-HPLC to afford the title compound (30 mg, yield 11%). Partial $^1$H NMR (CDCl$_3$, 400 MHz): δ7.81 (s, 1H), 7.78 (d, J=8.8 Hz, 2H), 7.34 (t, J=8.8 Hz, 2H), 6.79 (s, 1H), 6.16-6.15 (m, 1H) 4.81 (s, 1H), 4.73-4.67 (m, 1H), 4.44 (d, J=7.6 Hz, 1H) 4.36-4.32 (m, 1H), 3.89-3.85 (m, 4H), 3.32-2.91 (m, 6H), 0.81 (t, J=7.6 Hz, 3H). LCMS: m/z 905.1 [M+H]$^+$.

Example 18: (2S,3aR,5aR,5bS,9S,13S,14R,16aS, 16bS)-13-{[(2R,5S,6R)-5-(dimethylamino)-6-methyloxan-2-yl]oxy}-9-ethyl-14-methyl-4-(4-phenyl-1H-1,2,3-triazol-1-yl)-2-{[(2R,3R,4R,5S,6S)-3,4,5-trimethoxy-6-methyloxan-2-yl]oxy}-1H,2H,3H,3aH, 5aH,5bH,6H,7H,9H,10H,11H,12H,13H,14H,15H, 16aH,16bH-as-indaceno[3,2-d]oxacyclododecane-7, 15-dione

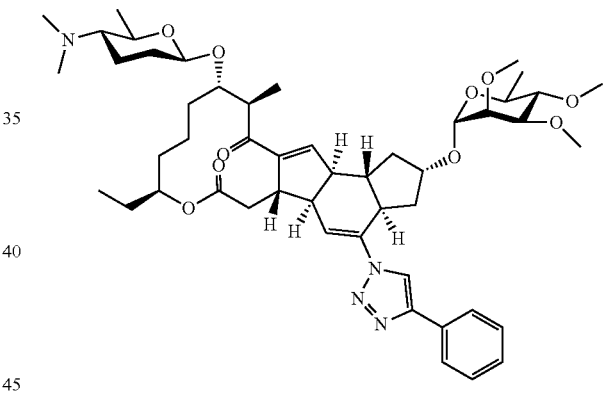

The hydroxytriazole intermediate was prepared using the representative procedure for. A mixture of Intermediate 2 (300 mg, 0.38 mmol), phenylacetylene (220 mg, 1.9 mmol), copper sulfate (12 mg, 0.07 mmol) and sodium ascorbate (15 mg, 0.07 mmol) in t-BuOH/water (3 mL/1.5 mL) was stirred at 100° C. for 17 h in a sealed tube. The reaction mixture was filtered through kieselguhr, and the filtrate was concentrated. The residue was purified by prep-HPLC to afford the hydroxytriazole intermediate (80 mg, 23% yield) as a white solid. Partial $^1$H NMR (CDCl$_3$, 400 MHz): δ 8.02 (s, 1H), 7.86 (d, J=8.0 Hz, 2H), 7.45 (t, J=7.6 Hz, 2H), 7.36-7.33 (m, 2H), 6.87 (s, 1H), 4.71-4.63 (m, 2H), 4.51-4.41 (m, 1H), 4.38 (s, 1H), 4.28-4.23 (m, 1H), 3.64-3.41 (m, 15H), 3.29-2.96 (m, 6H), 2.76-2.71 (m, 1H), 2.38-2.21 (m, 9H), 2.00-1.05 (m, 34H), 0.81 (t, J=7.6 Hz, 3H), LCMS: m/z 893.1 [M+H]$^+$.

To a solution of the above intermediate (900 mg, 1.0 mmol) in dichloromethane (5 mL) was added DAST (812 mg, 5.0 mmol) at −78° C. under N$_2$. After stirring at −78° C. for 30 min, the mixture was warmed to room temperature and quenched with aqueous sodium bicarbonate (10 mL).

After stirring for 15 min, the mixture was extracted with dichloromethane (10 mL×2). The combined organic layer was washed with brine, dried over sodium sulfate, filtered and concentrated. The residue was purified by prep-HPLC to afford the title compound (200 mg, yield 22%) as a white solid. Partial $^1$H NMR (CDCl$_3$, 400 MHz): δ7.87-7.85 (m, 2H), 7.82 (s, 1H), 7.45 (t, J=7.2 Hz, 2H), 7.36 (t, J=7.6 Hz, 1H), 6.81 (s, 1H), 5.32-2.16 (m, 1H), 4.78-4.72 (m, 2H), 0.82 (t, J=7.2 Hz, 3H). LCMS: m/z 876.1 [M+H]$^+$.

Example 19: (2S,3aR,5aR,5bS,9S,13S,14R,16aS, 16bS)-13-{[(2R,5S,6R)-5-(dimethylamino)-6-methyloxan-2-yl]oxy}-9-ethyl-14-methyl-4-[4-(3-methylphenyl)-1H-1,2,3-triazol-1-yl]-2-{[(2R,3R,4R,5S, 6S)-3,4,5-trimethoxy-6-methyloxan-2-yl]oxy}-1H, 2H,3H,3aH,5aH,5bH,6H,7H,9H,10H,11H,12H,13H, 14H,15H,16aH,16bH-as-indaceno[3,2-d] oxacyclododecane-7,15-dione

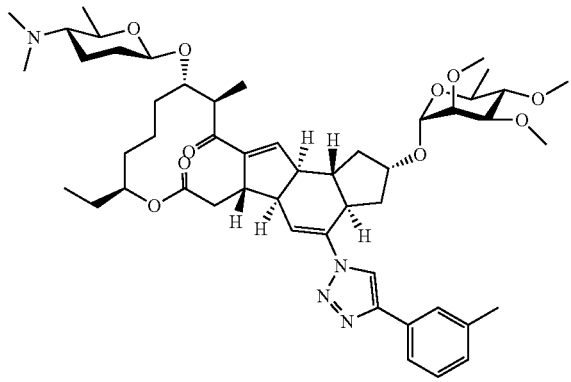

The hydroxyl triazole intermediate was prepared according to the representative procedure. The intermediate (950 mg, 1.05 mmol) in dichloromethane (10 mL) was cooled at −78° C. under N$_2$. Then DAST (844 mg, 5.2 mmol) was added dropwise. The mixture was stirred at −78° C. for 30 mins, then the mixture was allowed to warm up to room temperature. To the mixture was added sodium bicarbonate (aq 10 mL), and the reaction was extracted with dichloromethane (10 mL×3). The combined organic phase was washed with brine, dried over anhydrous sodium sulfate, filtered and concentrated. The crude product was further purified by prep-HPLC to afford the title compound (100 mg, yield 10%) as a white solid. Partial $^1$H NMR (CDCl$_3$, 400 MHz): δ7.81 (s, 1H), 7.70 (s, 1H), 7.63 (d, J=7.6 Hz, 1H), 7.35-7.32 (m, 1H), 7.16 (d, J=7.6 Hz 1H) 6.81 (s, 1H), 5.30-5.16 (m, 1H), 4.94-4.82 (m, 2H), 4.44-3.75 (m, 4H), 3.66-3.40 (m, 20H), 3.33-3.09 (m, 5H), 2.63-2.22 (m, 16H), 0.82 (t, J=7.2 Hz, 3H). LCMS: m/z 909.2 [M+H]$^+$.

Example 20: (2S,3aR,5aR,5bS,9S,13S,14R,16aS, 16bS)-9-ethyl-14-methyl-13-{[(2R,5S,6R)-6-methyl-5-(methylamino)oxan-2-yl]oxy}-4-[4-(3-methylphenyl)-1H-1,2,3-triazol-1-yl]-2-{[(2R,3R,4R,5S,6S)-3, 4,5-trimethoxy-6-methyloxan-2-yl]oxy}-1H,2H,3H, 3aH,5aH,5bH,6H,7H,9H,10H,11H,12H,13H,14H, 15H,16aH,16bH-as-indaceno[3,2-d] oxacyclododecane-7,15-dione

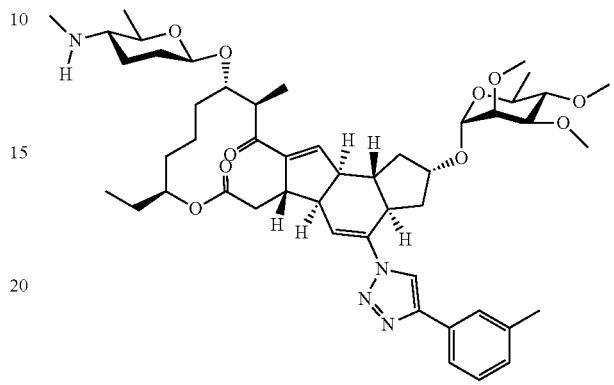

A mixture of Example 19 (150 mg, 0.16 mmol) and sodium acetate (69 mg, 0.84 mmol) in methanol/water (10 mL/2 mL) was heated to 47° C. At this point I$_2$ (64 mg, 0.25 mmol) was added in one portion, and the pH was adjusted between 8-9 by 1 N NaOH. After stirring for 2.5 h, the reaction was complete as monitored by LCMS. The reaction was cooled to r.t., quenched with saturated ammonium chloride solution (30 mL) and extracted with ethyl acetate (3×20 mL). The combined organic phase was washed with brine (50 mL), dried over anhydrous sodium sulfate, filtered and concentrated. The residue was purified by prep-HPLC to afford the title compound (30 mg, 17% yield) as a white solid. Partial $^1$H NMR (400 MHz, CDCl$_3$): 7.88 (s, 1H), 7.71 (s, 1H), 7.63 (d, J=8.0 Hz, 1H), 7.34 (d, J=7.2 Hz, 1H), 7.17 (d, J=7.6 Hz, 1H), 6.79 (s, 1H), 6.16 (m, 1H), 4.81 (s, 1H), 4.73-4.67 (m, 1H), 4.47 (d, J=8.4 Hz, 1H), 4.37-4.31 (m, 1H), 3.91-3.87 (m, 1H), 3.68-3.63 (m, 1H), 3.32-3.09 (m, 5H), 3.01-2.91 (m, 2H), 2.48-2.10 (m, 9H), 1.94 (d, J=12.8 Hz, 1H), 0.83 (t, J=7.2 Hz, 3H); LCMS: m/z 876.2 [M+H]$^+$.

Example 21: (2S,3aR,5aR,5bS,9S,13S,14R,16aS, 16bS)-9-ethyl-4-[4-(4-methoxyphenyl)-1H-1,2,3-triazol-1-yl]-14-methyl-13-{[(2R,5S,6R)-6-methyl-5-(methylamino)oxan-2-yl]oxy}-2-{[(2R,3R,4R,5S, 6S)-3,4,5-trimethoxy-6-methyloxan-2-yl]oxy}-1H, 2H,3H,3aH,5aH,5bH,6H,7H,9H,10H,11H,12H,13H, 14H,15H,16aH,16bH-as-indaceno[3,2-d] oxacyclododecane-7,15-dione

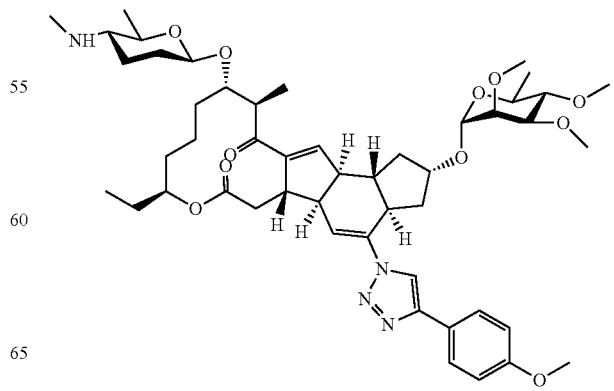

A mixture of Example 17 (300 mg, 0.33 mmol) and sodium acetate (136 mg, 1.66 mmol) in methanol/water (20 mL/5 mL) was heated to 47° C. At this point I$_2$ (126 mg, 0.5 mmol) was added in one portion, and the pH was adjusted between 8-9 using IN NaOH. After stirring for 2.5 h, the reaction was complete as monitored by LCMS. The reaction was cooled to r.t., quenched with saturated ammonium chloride solution (30 mL) and extracted with ethyl acetate (3×20 mL). The combined organic phase was washed with brine (50 mL), dried over anhydrous sodium sulfate, filtered and concentrated. The residue was purified by prep-HPLC to afford the title compound (270 mg, 91% yield) as a white solid. Partial $^1$H NMR (400 MHz, CDCl$_3$): 7.81 (s, 1H), 7.78 (d, J=8.8 Hz, 2H), 6.97 (d, J=8.8 Hz, 2H), 6.79 (s, 1H), 6.16 (m, 1H), 4.82 (s, 1H), 4.73-4.67 (m, 1H), 4.47 (d, J=8.4 Hz, 1H), 4.37-4.31 (m, 1H), 3.90-3.83 (m, 4H), 3.68-3.63 (m, 1H), 3.34-3.09 (m, 6H), 3.01-2.91 (m, 2H), 2.48-2.10 (m, 9H), 1.94 (d, J=12.8 Hz, 1H), 0.83 (t, J=7.2 Hz, 3H); LCMS: m/z 891.7 [M+H]$^+$.

Examples 22: (2S,3aR,5aR,5bS,9S,13S,14R,16aS, 16bS)-4-(4-{[1,1'-biphenyl]-4-yl}-1H-1,2,3-triazol-1-yl)-13-{[(2R,5S,6R)-5-(dimethylamino)-6-methyl-oxan-2-yl]oxy}-9-ethyl-14-methyl-2-{[(2R,3R,4R, 5S,6S)-3,4,5-trimethoxy-6-methyloxan-2-yl]oxy}-1H,2H,3H,3aH,5aH,5bH,6H,7H,9H,10H,11H,12H, 13H,14H,15H,16aH,16bH-as-indaceno[3,2-d] oxacyclododecane-7,15-dione

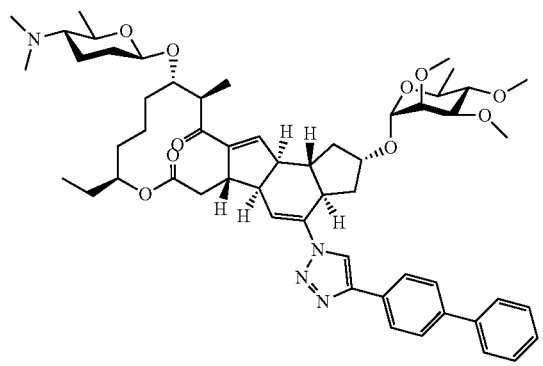

The hydroxytriazole intermediate was prepared using the representative procedure and 4-ethynylbiphenyl. To a solution of the intermediate (290 mg, 0.3 mmol) in dichloromethane (20 mL) was added DAST (3 mL) at −78° C. under N$_2$. After stirring at −78° C. for 30 min, the mixture was warmed to room temperature and quenched with aqueous sodium bicarbonate (50 mL). After stirring for 15 min, the mixture was extracted with dichloromethane (20 mL×3). The combined organic layer was washed with brine, dried over sodium sulfate, filtered and concentrated. The residue was purified by prep-HPLC to afford the title compound (30 mg, yield 10%) as a white solid. Partial $^1$H NMR (CDCl$_3$, 400 MHz): δ 7.93 (d, J=6.8 Hz, 2H), 7.86 (s, 1H), 7.68-7.62 (m, 4H), 7.45 (t, J=7.2 Hz, 2H), 7.36 (t, J=7.2 Hz, 1H), 6.81 (s, 1H), 5.31-5.16 (m, 1H), 4.72 (s, 2H), 4.46-4.30 (m, 3H), 3.84-3.74 (m, 1H), 3.66-3.60 (m, 1H), 3.32-3.25 (m, 1H), 3.32-3.25 (m, 1H), 3.12-3.00 (m, 3H), 2.64-2.37 (m, 3H), 2.28-2.19 (m, 8H), 0.81 (t, J=7.6 Hz, 3H), LCMS: m/z 971.2 [M+H]$^+$.

Example 23: (2S,3aR,5aR,5bS,9S,13S,14R,16aS, 16bS)-4-[4-(3-aminophenyl)-1H-1,2,3-triazol-1-yl]-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H, 3H,3aH,5aH,5bH,6H,7H,9H,10H,11H,12H,13H, 14H,15H,16aH,16bH-as-indaceno[3,2-d] oxacyclododecane-7,15-dione

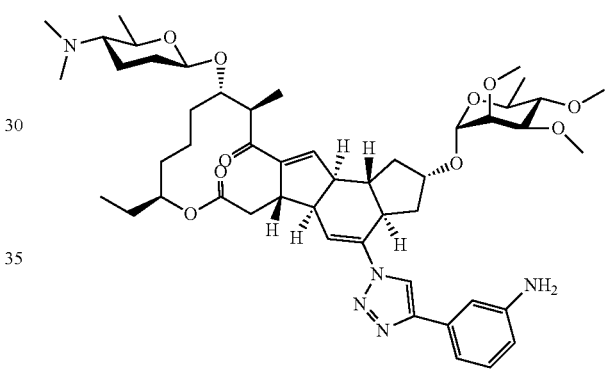

The hydroxytriazole intermediate was prepared from Intermediate 2 using the representative procedure using 3-ethynylaniline. To a solution of the intermediate (150 mg, 0.16 mmol) in dichloromethane (20 mL) was added DAST (2 mL) at −78° C. under N$_2$. After stirring at −78° C. for 30 min, the mixture was warmed to room temperature and quenched with aqueous sodium bicarbonate (30 mL). After stirring for 15 min, the mixture was extracted with dichloromethane (20 mL×3). The combined organic layer was washed with brine, dried over sodium sulfate, filtered and concentrated. The residue was purified by prep-HPLC to afford the title compound (50 mg, yield 34%) as a white solid. Partial $^1$H NMR (CDCl$_3$, 400 MHz): δ 7.84 (s, 1H), 7.28 (s, 1H), 7.23-7.14 (m, 2H), 6.79 (s, 1H), 6.68-6.66 (m, 1H), 6.16 (s, 1H), 4.81 (s, 1H), 4.73-4.61 (m, 1H), 4.43 (d, J=7.6 Hz, 1H), 4.36-4.30 (m, 1H), 3.91-3.85 (m, 1H), 3.76-3.62 (m, 3H), 3.34-3.05 (m, 4H), 3.01-2.89 (m, 2H), 2.46-2.32 (m, 2H), 2.26-2.19 (m, 9H), 0.84 (t, J=7.6 Hz, 3H), LCMS: m/z 890.1 [M+H]$^+$.

Example 24: (2S,3aR,5aR,5bS,9S,13S,14R,16aS, 16bS)-4-[4-(4-aminophenyl)-1H-1,2,3-triazol-1-yl]-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione

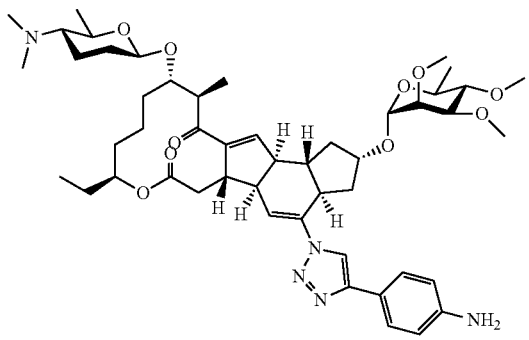

The hydroxytriazole intermediate was prepared from Intermediate 2 using the representative procedure using 4-ethynylaniline. To a solution of the intermediate (150 mg, 0.16 mmol) in dichloromethane (20 mL) was added DAST (2 mL) at −78° C. under $N_2$. After stirring at −78° C. for 30 min, the mixture was warmed to room temperature and quenched with aqueous sodium bicarbonate (30 mL). After stirring for 15 min, the mixture was extracted with dichloromethane (20 mL×3). The combined organic layer was washed with brine, dried over sodium sulfate, filtered and concentrated. The residue was purified by prep-HPLC to afford the title compound (30 mg, yield 20%) as a white solid. Partial $^1$H NMR (CDCl$_3$, 400 MHz): δ 7.75 (s, 1H), 7.64 (d, J=8.4 Hz, 1H), 6.79 (s, 1H), 6.74 (d, J=8.4 Hz, 2H), 6.14 (s, 1H), 5.34 (s, 1H), 4.81 (s, 1H), 4.71 (s, 1H), 4.43 (d, J=8.4 Hz, 1H), 3.31-2.89 (m, 7H), 2.46-2.16 (m, 13H), 0.84 (t, J=7.2 Hz, 3H), LCMS: m/z 890.1 [M+H]$^+$.

Example 25: (2S,5bS,9S,13S,14R,16aR,16bR)-13-{[(2R,5S,6R)-5-(dimethylamino)-6-methyloxan-2-yl]oxy}-9-ethyl-14-methyl-5-phenyl-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione

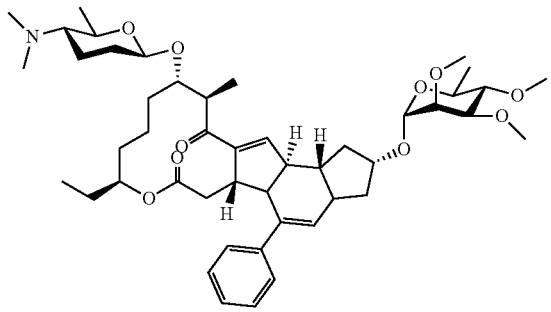

To a solution of Intermediate 1 (383 mg, 0.5 mol) and phenylboronic acid (122 mg, 1 mmol) in toluene (10 mL) was added Pd(dppf)Cl$_2$ (36 mg, 0.05 mmol) and potassium carbonate (138 mg, 1 mmol). The system was charged with $N_2$ 3 times and stirred at 110° C. for 72 h. The reaction mixture was diluted with water (30 mL) and extracted with ethyl acetate (3×50 mL). The combined organic phase was washed with brine (30 mL), dried over anhydrous sodium sulfate, filtered and concentrated. The residue was purified by prep-HPLC to afford the title compound (30 mg, 7.4% yield) as a white solid. $^1$H NMR (400 MHz, Acetone): δ 7.28-7.26 (m, 2H), 7.17-7.13 (m, 1H), 7.02 (s, 1H), 5.70 (s, 1H), 4.73 (d, J=2.0 Hz, 1H), 4.56-4.49 (m, 1H), 4.33-4.30 (m, 1H), 4.28-4.23 (m, 1H), 4.14 (tt, J$_1$=8.4 Hz, J$_2$=2.4 Hz, 1H), 4.09 (t, J=8.4 Hz, 1H), 3.46-3.37 (m, 4H), 3.35-3.26 (m, 10H), 3.24-3.16 (m, 1H), 2.93-2.87 (m, 2H), 2.82-2.80 (m, 1H), 2.68-2.64 (m, 1H), 2.58 (dd, J$_1$=13.6 Hz, J$_2$=4.8 Hz, 1H), 2.31-2.24 (m, 1H), 2.17-2.12 (m, 1H), 2.07 (s, 6H), 2.01-1.95 (m, 2H), 1.90-1.88 (m, 1H), 1.82-1.76 (m, 1H), 1.72-1.62 (m, 3H), 1.47-1.16 (m, 12H), 1.07-1.05 (m, 6H), 0.99 (d, J=6.8 Hz, 3H), 0.95-0.85 (m, 2H), 0.64 (t, J=7.2 Hz, 3H); LCMS: m/z 807.9 [M−H]$^+$.

Example 26: (2S,3aR,5aR,5bS,9S,13S,14R,16aS,16bS)-4-[4-(3-chlorophenyl)-1H-1,2,3-triazol-1-yl]-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione

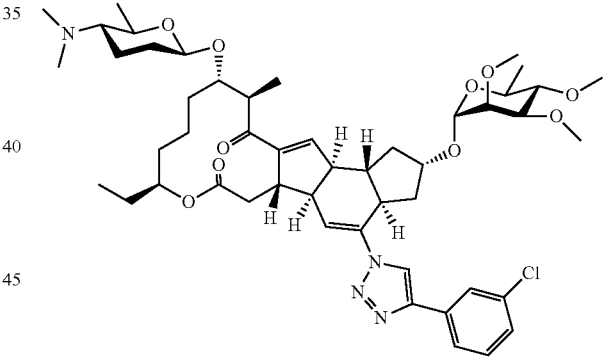

The hydroxytriazole intermediate was prepared according to the representative procedure for hydroxy triazole synthesis using Intermediate 2 (300 mg, 0.38 mmol), 1-Chloro-3-ethynyl-benzene (180 mg, 1.9 mmol), copper sulfate (12 mg, 0.07 mmol), and sodium ascorbate (15 mg, 0.07 mmol) to provide the hydroxytriazole intermediate as a white solid. Partial $^1$H NMR (CDCl$_3$, 400 MHz): δ 8.06 (s, 1H), 7.83 (s, 1H), 7.76 (d, J=7.6 Hz, 1H), 7.38 (t, J=8.0 Hz, 1H), 7.32-7.27 (m, 1H), 6.87 (s, 1H), 4.70-4.63 (m, 2H), 4.54-4.50 (m, 1H), 4.44 (d, J=1.2 Hz, 1H), 4.36 (s, 1H), 4.28-4.22 (m, 1H), 3.30-2.96 (m, 8H), 2.74-2.70 (m, 1H), 2.40-2.20 (m, 12H), 0.82 (t, J=7.2 Hz, 3H), LCMS: m/z 926.2 [M+H]$^+$.

To a solution of the above intermediate (150 mg, 0.16 mmol) in dichloromethane (10 mL) was added DAST (3 mL) at −78° C. under nitrogen. After stirring at −78° C. for 30 min, the mixture was warmed to room temperature and quenched with aqueous sodium bicarbonate (30 mL). After stirring for 15 min, the mixture was extracted with dichloromethane (20 mL×3). The combined organic layer was washed with brine, dried over Sodium sulfate, filtered and concentrated. The residue was purified by prep-HPLC to afford the title compound (30 mg, yield 20%) as a white solid.

Partial $^1$H NMR (CDCl$_3$, 400 MHz): δ 7.85-7.84 (m, 2H), 7.75 (d, J=7.2 Hz, 1H), 7.40-7.31 (m, 2H), 6.81 (s, 1H), 6.29-6.14 (m, 1H), 4.72 (s, 1H), 4.43-4.31 (m, 3H), 4.37-4.32 (m, 1H), 3.84-3.758 (m, 1H), 3.66-3.62 (m, 1H), 3.29-2.99 (m, 4H), 2.63-2.24 (m, 10H), 0.82 (t, J=7.2 Hz, 3H), LCMS: m/z 931.1 [M+H]$^+$.

Intermediate 4: (2S,3aR,5aR,5bS,9S,13S,14R,16aR,16bS)-4-bromo-13-{[(2R,5S,6R)-5-(dimethyl-amino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,-11H,12H,13H,14H,15H,16aH,16bH-as-indaceno[3,2-d]oxacyclododecane-5,7,15-trione

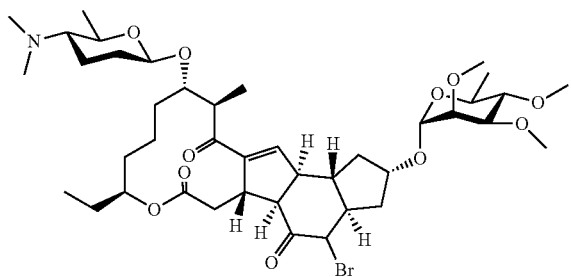

To a solution of Spinosyn A (5.0 g, 6.8 mmol) in dimethyl sulfoxide (DMSO, 50 mL) was added dropwise 10 mL of water and concentrated sulfuric acid (670 mg, 6.8 mmol). The mixture was then cooled to 0° C. and N-bromosuccinimide (NBS; 1.2 g, 6.8 mmol) was added. After stirring for 30 minutes at 0° C., ethyl acetate (200 mL) and saturated aqueous sodium bicarbonate (150 mL) were added. The organic layer was washed with water and brine, dried over sodium sulfate, filtered and concentrated in vacuo to give the bromo alcohol intermediate as a white solid (5.5 g, 97.1%) which was used in the next chemical step without further purification. To a solution of this white solid (5.5 g, 6.6 mmol) in dichloromethane (100 mL) at 0° C. was added Dess-Martin periodinane (3.1 g, 7.3 mmol). The mixture was stirred at room temperature overnight. The mixture was then washed with saturated sodium bicarbonate (30 mL), saturated Na$_2$SO$_3$ (20 mL), and brine. The organic layer was dried over sodium sulfate, filtered, and concentrated in vacuo to give an oil which was purified by silica gel column chromatography (using a dichloromethane to methanol gradient of from 50/1 to 15/1) to afford the title compound (2.1 g, 38.6%) as a white solid.

Intermediate 5: (2S,3aR,4S,9S,13S,14R,16aR,16bS)-13-{[(2R,5S,6R)-5-(dimethylamino)-6-methyloxan-2-yl]oxy}-9-ethyl-14-methyl-4-(4-phenyl-1H-1,2,3-triazol-1-yl)-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-5,7,15-trione

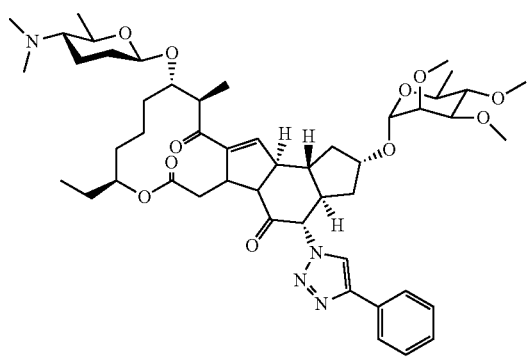

To a solution of Intermediate 4 (11.0 g, 13.3 mmol) in DMF (20 mL) was added sodium azide (5.2 g, 79.9 mmol) at room temperature. The resulting mixture was stirred at 60° C. for 2 h. The mixture was treated with sat. sodium bicarbonate and extracted with ethyl acetate (3×100 mL). The combined organic phase was washed with brine (30 mL), dried over anhydrous sodium sulfate, filtered and concentrated. The residue was purified by silica gel column chromatography (ethyl acetate to ethyl acetate:methanol=10:1) to afford the title compound (5.4 g, 51% yield) as a yellow solid. LC-MS: m/z 789 [M+H]$^+$.

Example 27: (2S,3aR,9S,13S,14R,16aR,16bS)-13-{[(2R,5S,6R)-5-(dimethylamino)-6-methyloxan-2-yl]oxy}-9-ethyl-5-fluoro-14-methyl-4-(4-phenyl-1H-1,2,3-triazol-1-yl)-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione

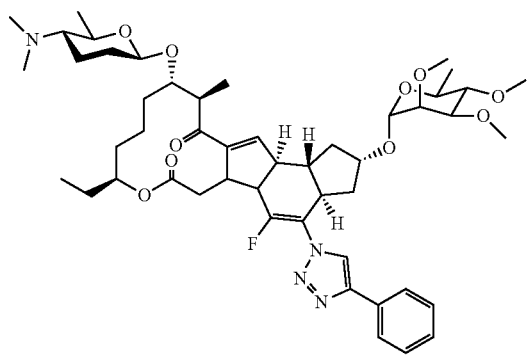

To a solution of Intermediate 5 (1.50 g, 1.90 mmol) and phenylacetylene (1.05 mL, 9.50 mmol) in t-butanol (6 mL) and water (3 mL) was added copper sulfate (60 mg, 0.38 mmol) and sodium ascorbate (75 mg, 0.38 mmol) in a sealed tube at room temperature. The resulting mixture was stirred vigorously at 100° C. overnight. The mixture was cooled to room temperature, then treated with water and extracted with ethyl acetate (3×50 mL). The combined organic phase was washed with brine (30 mL), dried over anhydrous sodium sulfate, filtered and concentrated. The residue was purified by column chromatography over silica gel (dichloromethane:methanol=20:1), followed by Prep-HPLC to afford the ketotriazole intermediate (620 mg, 37% yield) as a white solid. LC-MS: m/z 891 [M+H]$^+$.

To a solution of the above intermediate (620 mg, 0.697 mmol) in dichloromethane (20 mL) was added DAST (1.20 mL, 9.09 mmol) at 0° C. under nitrogen. The resulting mixture was stirred vigorously at r.t. overnight. The mixture was poured into saturated sodium bicarbonate and the mixture was extracted with dichloromethane (3×50 mL). The combined organic phase was washed with brine (30 mL), dried over anhydrous sodium sulfate, filtered and concentrated. The residue was purified by prep-HPLC to afford the title compound (90 mg, 14% yield) as a white solid. Partial $^1$H NMR (CDCl$_3$, 400 MHz): δ8.03 (d, J=2.4 Hz, 1H), 7.88-7.86 (m, 2H), 7.47-7.43 (m, 2H), 7.37-7.34 (m, 1H), 6.77 (s, 1H), 4.80 (d, J=1.6 Hz, 1H), 4.76-4.71 (m, 1H), 4.44-4.41 (m, 1H), 4.39-4.34 (m, 1H), 4.27-4.22 (m, 1H), 3.56 (s, 3H), 3.50 (s, 3H), 3.49 (s, 3H), 2.60 (dd, J=14.0 Hz, 3.2 Hz, 1H), 2.25 (s, 6H), 0.83 (t, J=7.2 Hz, 3H); LC-MS: m/z 894 [M+H]$^+$.

Example 28: Testing Compounds for Insecticide, Miticide, and Nematicide Utility

The compounds produced by the methods described above are tested for activity against a number of insects, mites, and nematodes. Successful compounds are useful for reducing populations of insects, mites, and/or nematodes, and are used in a method of inhibiting an insect, mite, and/or nematode population after application to a locus of the pest an effective insect-, mite-, or nematode-inactivating amount of a compound.

Activity Against *Spodoptera* Species:
Cotton leaf discs are placed on agar in 24-well microtiter plates and sprayed with serial dilutions of aqueous test solutions prepared from DMSO stock solutions, with a highest dose of 200 ppm. After drying, the leaf discs are infested with L1 larvae and samples are assessed for mortality after 4 to 8 days.

Activity Against *Plutella* Species:
Artificial diet optimized for Lepidopteran species is aliquoted into 24-well microtiter plates and treated with aqueous test solutions prepared from DMSO stock solutions by pipetting, with a highest dose of 200 ppm. After drying, the plates are infested with L2 larvae and mortality is assessed after 4 to 8 days.

Activity Against *Diabrotica* Species:
Artificial diet optimized for Coleopteran species is aliquoted into 24-well microtiter plates and treated with aqueous test solutions prepared from DMSO stock solutions by pipetting, with a highest dose of 200 ppm. After drying, the plates are infested with L2 larvae and mortality is assessed after 4 to 8 days.

Activity Against *Myzus* Species:
Sunflower leaf discs are placed on agar in a 24-well microtiter plate and sprayed with serial dilutions of aqueous test solutions prepared from DMSO stock solutions, with a highest dose of 200 ppm. After drying, the leaf discs are infested with a mixed age aphid population and samples are assessed for mortality after 4 to 8 days.

Activity Against *Thrips* Species:
Sunflower leaf discs are placed on agar in a 24-well microtiter plate and sprayed with serial dilutions of aqueous test solutions prepared from DMSO stock solutions, with a highest dose of 200 ppm. After drying, the leaf discs are infested with a mixed age thrips population and samples are assessed for mortality after 4 to 8 days.

Activity Against *Euschistus* Species:
Sunflower leaf discs are placed on agar in a 24-well microtiter plate and sprayed with serial dilutions of aqueous test solutions prepared from DMSO stock solutions, with a highest dose of 200 ppm. After drying, the leaf discs are infested N2 nymphs and samples are assessed for mortality after 4 to 8 days.

Activity Against *Tetranychus* Species:
Bean leaf discs are placed on agar in a 24-well microtiter plate and sprayed with serial dilutions of aqueous test solutions prepared from DMSO stock solutions, with a highest dose of 200 ppm. After drying, the leaf discs are infested with mixed mobile populations and samples are assessed for mortality after 4 to 8 days.

Activity Against *Meloidogyne* Species:
Untreated cucumber seeds are placed into the bottom of a clear cup to which clean white sand is added. The cups are sprayed with aqueous test solution while rotating on a pedestal allowing the test solution to be deposited on the sand. To each cup is dispensed water containing nematodes. After 10 to 14 days the nematode populations are assessed for mortality.

Activity Against *Blattella* Species:
Green insect diet material is dispensed into a diet cup onto which aqueous test solution is sprayed. Treated cups are air dried and infested with late third or early fourth instar cockroaches. After 10 to 14 days the cockroach populations are assessed for mortality.

Activity Against *Aedes* Species:
L2 *Aedes* larvae in a nutrition mixture are placed in 96-well microtiter plates. Aqueous test solutions are pipetted into the wells. After 1 to 3 days the mosquito populations are assessed for mortality.

All examples described above were active at test solution concentrations of 200 ppm or below against at least one of the above test organisms.

It is understood that the terminology used herein is for the purpose of describing particular embodiments only, and the terminology is not intended to be limiting. The scope of the invention will be limited only by the appended claims. Unless defined otherwise, all technical and scientific terms used herein have the same meaning as commonly understood by one of ordinary skill in the art to which this invention belongs. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number.

All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the invention described herein is not entitled to antedate such publication by virtue of prior invention. Further, the dates of publication provided might be different from the actual publication dates, which may need to be independently confirmed.

It is noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of skill in the art upon reading this disclosure, each of the individual embodiments described and illustrated herein has discrete components and features which may be readily separated from or combined with the features of any of the other several embodiments without departing from the scope or spirit of the invention. Any recited method may be carried out in the order of events recited or in any other order that is logically possible. Although any methods and materials similar or equivalent to those described herein may also be used in the practice or testing of the invention, representative illustrative methods and materials are now described.

The invention claimed is:
1. A spinosyn compound of the following formula:

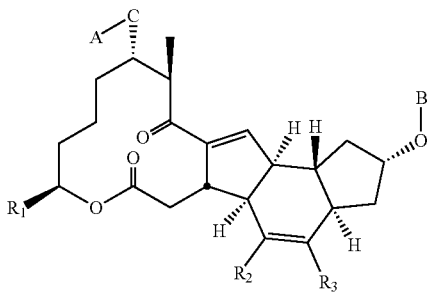

or a salt thereof, wherein:
A is selected from the group consisting of substituted or unsubstituted carbonyl, substituted or unsubstituted cycloalkyl, substituted or unsubstituted heterocycloalkyl, substituted or unsubstituted aryl, and substituted or unsubstituted heteroaryl;
B is selected from the group consisting of substituted or unsubstituted cycloalkyl, substituted or unsubstituted heterocycloalkyl, substituted or unsubstituted aryl, and substituted or unsubstituted heteroaryl;
C is O or NH;
$R^1$ is selected from the group consisting of substituted or unsubstituted alkyl, substituted or unsubstituted aryl; and
$R^2$ and $R^3$ are each independently selected from the group consisting of hydrogen, halogen, substituted or unsubstituted amino, substituted or unsubstituted alkoxy, substituted or unsubstituted aryloxy, substituted or unsubstituted alkyl, substituted or unsubstituted cycloalkyl, substituted or unsubstituted heterocycloalkyl, substituted or unsubstituted aryl, and substituted or unsubstituted heteroaryl, wherein at least one of $R^2$ and $R^3$ comprises a phenyl, substituted phenyl, triazole, or substituted triazole.

2. The spinosyn compound of claim 1, wherein A comprises forosamine or [(2R,5S,6R)-6-methyl-5-(methylamino)oxan-2-yl]; and wherein B comprises rhamnose; 3,4,5-trimethoxyrhamnose; or 4-ethoxy-3,5-dimethoxyrhamnose.

3. The spinosyn compound of claim 1, wherein:
A comprises forosamine or [(2R,5S,6R)-6-methyl-5-(methylamino)oxan-2-yl];
B comprises rhamnose; 3,4,5-trimethoxyrhamnose; or 4-ethoxy-3,5-dimethoxyrhamnose;
C comprises oxygen;
$R^1$ comprises ethyl; and
wherein one of $R^2$ and $R^3$ comprises a phenyl, substituted phenyl, triazole, or substituted triazole and one of $R^2$ and $R^3$ is hydrogen.

4. The spinosyn compound of claim 1, wherein at least one of $R^2$ and $R^3$ comprises a phenyl or a substituted phenyl, and wherein the substituted phenyl comprises chlorophenyl, fluorophenyl, methylphenyl, ethylphenyl, trifluoromethylphenyl, methoxyphenyl, ethoxyphenyl, trifluoromethoxy phenyl, or methylbenzoate.

5. The spinosyn compound of claim 1, wherein at least one of $R^2$ and $R^3$ comprises a substituted triazole, and wherein the substitution on the substituted triazole comprises a phenyl, methylphenyl, methoxyphenyl, biphenyl, aminophenyl, chlorophenyl or fluorophenyl moiety.

6. The spinosyn compound of claim 1, wherein the spinosyn compound is (2S,5bS,9S,13S,14R,16aS,16bS)-13-{[(2R,5S,6R)-5-(dimethylamino)-6-methyloxan-2-yl]oxy}-9-ethyl-14-methyl-4-phenyl-2-{[(2R,3R,4R,5S,6S)-3,4,5-trimethoxy-6-methyloxan-2-yl]oxy}-1H,2H,3H,3aH,5aH, 5bH,6H,7H,9H,10H,11H,12H,13H,14H,15H,16aH,16bH-as-indaceno[3,2-d]oxacyclododecane-7,15-dione.

7. The spinosyn compound of claim 1, wherein the spinosyn compound is (2S,5bS,9S,13S,14R,16aS,16bS)-13-{[(2R,5S,6R)-5-(dimethylamino)-6-methyloxan-2-yl]oxy}-9-ethyl-4-(4-methoxyphenyl)-14-methyl-2-{[(2R,3R,4R, 5S,6S)-3,4,5-trimethoxy-6-methyloxan-2-yl]oxy}-1H,2H, 3H,3aH,5aH,5bH,6H,7H,9H,10H,11H,12H,13H,14H,15H, 16aH,16bH-as-indaceno[3,2-d]oxacyclododecane-7,15-dione.

8. The spinosyn compound of claim 1, wherein the spinosyn compound is (2S,3aR,5aR,5bS,9S,13S,14R,16aS, 16bS)-13-{[(2R,5S,6R)-5-(dimethylamino)-6methyloxan-2-yl]oxy}-9-ethyl-14-methyl-4-(4-phenyl-1H-1,2,3-triazol-1-yl)-2-{[(2R,3R,4R,5S,6S)-3,4,5-trimethoxy-6-methyloxan-2-yl]oxy}-1H,2H,3H,3aH,5aH,5bH,6H,7H,9H, 10H,11H,12H,13H,14H,15H,16aH,16bH-as-indaceno[3,2-d]oxacyclododecane-7,15-dione.

9. The spinosyn compound of claim 1, wherein the spinosyn compound is (2S,3aR,5aR,5bS,9S,13S,14R,16aS, 16bS)-9-ethyl-4-[4-(4-methoxyphenyl)-1H-1,2,3-triazol-1-yl]-14-methyl-13-{[(2R,5S,6R)-6-methyl-5-(methylamino) oxan-2-yl]oxy}-2-{[2R,3R,4R,5S,6S)-3,4,5-trimethoxy-6- methyloxan-2-yl]oxy}-1H,2H,3H,3aH,5aH,5bH,6H,7H,9H,
10H,11H,12H,13H,14H,15H,16aH,16bH-as-indaceno[3,2-
d]oxacyclododecane-7,15-dione.

10. The spinosyn compound of claim 1, wherein the spinosyn compound is (2S,5bS,9S,13S,14R,16aS,16bS)-13-{[(2R,5S,6R)-5-(dimethylamino)-6-methyloxan-2-yl]oxy}-2-{[(2R,3R,4R,5S,6S)-4-ethoxy-3,5-dimethoxy-6-methyloxan-2-yl]oxy}-9-ethyl-14-methyl-4-phenyl-1H,2H,3H,3aH,5aH,5bH,6H,7H,9H,10H,11H,12H,13H,14H,15H,16aH,16bH-as-indaceno[3,2-d]oxacyclododecane-7,15-dione.

11. The spinosyn compound of claim 1, wherein the spinosyn compound is (2S,5bS,9S,13S,14R,16aS,16bS)-13-{[(2R,5S,6R)-5-(dimethylamino)-6-methyloxan-2-yl]oxy}-2-{[(2R,3R,4R,5S,6S)-4-ethoxy-3,5-dimethoxy-6-methyloxan-2-yl]oxy}-9-ethyl-14-methyl-4-(4-phenyl-1H-1,2,3-triazol-1-yl)-1H,2H,3H,3aH,5aH,5bH,6H,7H,9H,10H,11H,12H,13H,14H,15H,16aH,16bH-as-indaceno[3,2-d]oxacyclododecane-7,15-dione.

12. A formulation, comprising the spinosyn compound of claim 1 and an acceptable carrier.

13. The formulation of claim 12, further comprising at least one additional active ingredient.

14. The formulation of claim 13, wherein the additional active ingredient is a contact-acting insecticide.

15. The formulation of claim 13, wherein the additional active ingredient is a contact-acting miticide.

16. A method for controlling pests, comprising contacting a pest with an effective amount of a spinosyn compound of claim 1.

17. The method of claim 16, wherein the pest is an insect.

18. The method of claim 16, wherein the pest is an arachnid.

19. The method of claim 16, wherein the pest is a nematode.

* * * * *